United States Patent
Nikolov et al.

(10) Patent No.: US 12,378,321 B2
(45) Date of Patent: Aug. 5, 2025

(54) ADAM17 BINDING MOLECULES AND USES THEREOF

(71) Applicants: MEMORIAL SLOAN KETTERING CANCER CENTER, New York, NY (US); The U.S.A, as represented by the Secretary, Department of Health and Human Services, Bethesda, MD (US); Tri-Institutional Therapeutics Discovery Institute, Inc., New York, NY (US)

(72) Inventors: Dimitar Nikolov, New York, NY (US); Nayanendu Saha, New York, NY (US); Zhongyu Zhu, Frederick, MD (US); Dimiter Stanchev Dimitrov, Frederick, MD (US); Dorothea Robev, New York, NY (US); Thomas Edgeworth White, Norwalk, CT (US)

(*) Notice: Subject to any disclaimer, the term of this patent is extended or adjusted under 35 U.S.C. 154(b) by 778 days.

(21) Appl. No.: 17/437,065

(22) PCT Filed: Mar. 7, 2020

(86) PCT No.: PCT/US2020/021603
§ 371 (c)(1),
(2) Date: Sep. 8, 2021

(87) PCT Pub. No.: WO2020/185635
PCT Pub. Date: Sep. 17, 2020

(65) Prior Publication Data
US 2023/0159653 A1  May 25, 2023

Related U.S. Application Data

(60) Provisional application No. 62/815,471, filed on Mar. 8, 2019.

(51) Int. Cl.
*C07K 16/28* (2006.01)
*A61K 39/00* (2006.01)
*A61P 35/00* (2006.01)

(52) U.S. Cl.
CPC .......... *C07K 16/2896* (2013.01); *A61P 35/00* (2018.01); *A61K 39/00* (2013.01); *A61K 2039/505* (2013.01)

(58) Field of Classification Search
None
See application file for complete search history.

(56) References Cited

U.S. PATENT DOCUMENTS

| | | |
|---|---|---|
| 7,960,513 B2 | 6/2011 | Lackmann et al. |
| 2007/0004910 A1 | 1/2007 | Sexton et al. |
| 2016/0326257 A1 | 11/2016 | Lowe |

FOREIGN PATENT DOCUMENTS

| | | |
|---|---|---|
| WO | 2005/034733 A2 | 4/2005 |
| WO | 2006063415 A1 | 8/2015 |
| WO | 2015117199 A1 | 8/2015 |

OTHER PUBLICATIONS

Saha et al., Translational Oncology 15 (2022) 101265 (Year: 2022).*
Atapattu et al., 2012. Antibodies binding the ADAM10 substrate recognition pocket inhibit Eph function. J Cell Sci. 125:6084-93. 2012. PMCID: PMC 3585520.
Atapattu et al., 2016. An activated form of ADAM10 is tumor selective and regulates cancer stem-like cells and tumor growth. J Exp Med. Aug. 22; 213(9): 1741-57. PMCID: PMC 4995075.
Janes et al., 2005. Adam Meets Eph: An ADAM Substrate Recognition Module Acts as a Molecular Switch for Ephrin Cleavage in trans. Cell. 123, 291-30. PMID: 16239146.
North et al., A new clustering of antibody CDR loop conformations; J Mol Biol. Feb. 18, 2011; 406(2): 228-256.
Saha et al., 2007. Cell-cell signaling via Eph receptors and ephrins. Curr Opin Cell Biol. Oct. 19 (5): 534-42. PMCID: PMC 3327877.
Wieduwilt et al., The epidermal growth factor receptor family: Biology driving targeted therapeutics. Cell Mol Life Sci. May 2008 ; 65(10): 1566-1584.
Zhu et al. Construction of a Large Naïve Human Phage-Displayed Fab Library Through One-Step Cloning, Methods Mol Biol. 2009 ; 525: 129-xv. Doi. 10.1007/978-1-59745-554-1_6.
International Search Report & Written Opinion for PCT/US20/21603, Jul. 24, 2020.
Peng et al: "Molecular basis for the mechanism of action of an anti-TACE antibody", mAbs, vol. 8, No. 8, Sep. 9, 2016 (Sep. 9, 2016), pp. 1598-1605, XP093007747, US ISSN: 1942-0862, DOI: 10.1080/19420862.2016.1226716.
Saha et al: "ADAM proteases: Emerging role and targeting of the non-catalytic domains", Cancer Letters, New York, NY, US, vol. 467, Oct. 5, 2019 (Oct. 5, 2019), pp. 50-57, XP085882774, ISSN: 0304-3835, DOI: https://doi.org/10.1016/j.canlet.2019.10.003.

* cited by examiner

*Primary Examiner* — Christina M Borgeest
(74) *Attorney, Agent, or Firm* — Grimes & Yvon LLP

(57) ABSTRACT

The present invention provides various ADAM17 binding molecules (including antibodies and fragments thereof), compositions comprising such ADAM17 binding molecules, and methods of using such ADAM17 binding molecules and compositions, for example in inhibiting binding of ADAM17 to ADAM17 substrates (such as ErbB ligands), in inhibiting the proliferation of cancer cells, and in treating cancer.

20 Claims, 13 Drawing Sheets
Specification includes a Sequence Listing.

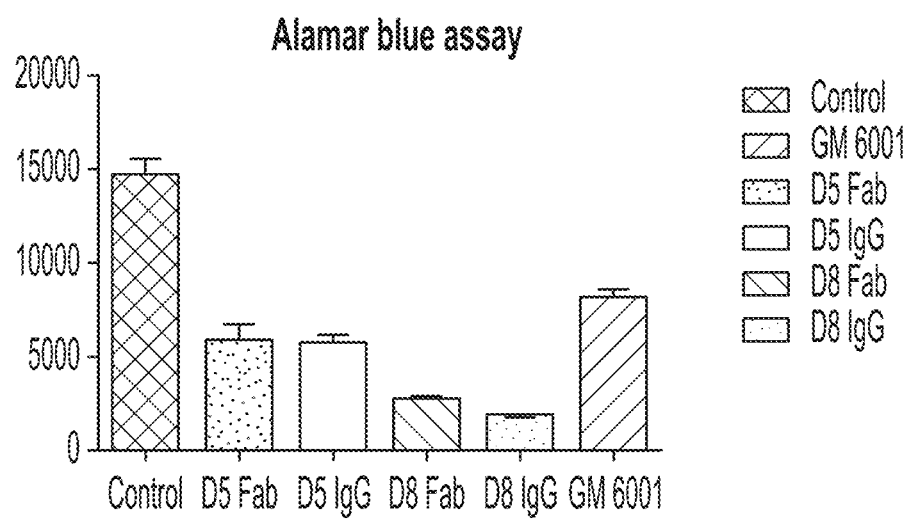
FIG. 2A
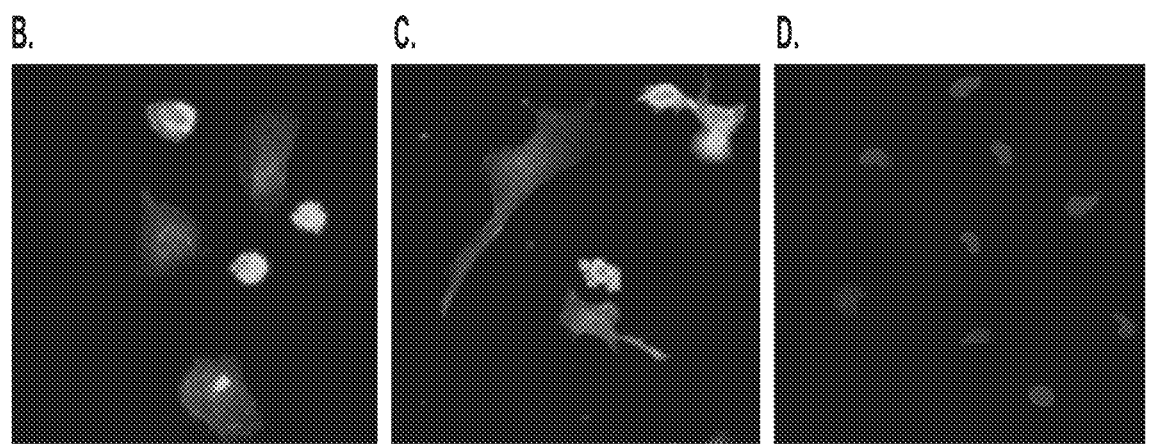
FIG. 2B-D

SEQUENCE LISTING

```
<160> NUMBER OF SEQ ID NOS: 53

<210> SEQ ID NO 1
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Gln Gln Ser Gly
                20                  25                  30

Ala Glu Val Lys Lys Pro Gly Ala Ser Val Lys Val Ser Cys Lys Ala
            35                  40                  45

Ser Gly Tyr Thr Phe Thr Gly Tyr Tyr Met His Trp Val Arg Gln Ala
        50                  55                  60

Pro Gly Gln Gly Leu Glu Trp Met Gly Trp Ile Asn Gly Lys Ser Gly
65                  70                  75                  80

Gly Thr Asn Tyr Ala Gln Lys Phe Gln Gly Arg Val Thr Met Thr Arg
                85                  90                  95

Asp Thr Ser Ile Ser Thr Ala Tyr Met Glu Leu Ser Arg Leu Lys Ser
            100                 105                 110

Asp Asp Thr Ala Val Tyr Tyr Cys Ala Arg Leu Asp Arg Arg Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285
```

Ser His Glu Asp Pro Glu Val Lys Phe Asn Trp Tyr Val Asp Gly Val
    290                 295                 300

Glu Val His Asn Ala Lys Thr Lys Pro Arg Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly
465

<210> SEQ ID NO 2
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ser Val Pro Thr Gln Val Leu Gly Leu Leu Leu Leu Trp Leu Thr
1               5                   10                  15

Asp Ala Arg Cys Gln Ser Val Val Thr Gln Pro Pro Ser Val Ser Gly
            20                  25                  30

Ala Pro Gly Gln Arg Val Thr Ile Ser Cys Ser Gly Ser Ser Ser Asn
        35                  40                  45

Val Gly Arg Asn Leu Val Tyr Trp Tyr Gln Gln Leu Pro Gly Ala Ala
    50                  55                  60

Pro Arg Leu Leu Ile Tyr Arg Asn Asn Gln Arg Pro Ser Gly Val Pro
65                  70                  75                  80

Asp Arg Phe Ser Gly Ser Lys Ser Gly Thr Ser Ala Ser Leu Ala Ile
            85                  90                  95

Ser Gly Leu Arg Ser Glu Asp Glu Ala Asp Tyr Tyr Cys Ala Ala Trp
            100                 105                 110

Asp Asp Ser Leu Ser Gly Val Val Phe Gly Gly Gly Thr Lys Leu Thr
            115                 120                 125

Val Leu Gly Gln Pro Lys Ala Ala Pro Ser Val Thr Leu Phe Pro Pro
            130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser

```
                165                 170                 175
Ser Pro Val Lys Ala Gly Val Glu Thr Thr Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235

<210> SEQ ID NO 3
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Gln Gln Ser Gly
            20                  25                  30

Ala Glu Val Lys Lys Pro Gly Ala Ser Val Lys Val Ser Cys Lys Ala
        35                  40                  45

Ser Gly Tyr Thr Phe Thr Gly Tyr Tyr Met His Trp Val Arg Gln Ala
    50                  55                  60

Pro Gly Gln Gly Leu Glu Trp Met Gly Trp Ile Asn Gly Asn Ser Gly
65                  70                  75                  80

Gly Thr Asn Tyr Ala Gln Lys Phe Gln Gly Arg Val Thr Met Thr Arg
                85                  90                  95

Asp Thr Ser Ile Ser Thr Ala Tyr Met Glu Leu Ser Arg Leu Lys Ser
            100                 105                 110

Asp Asn Thr Ala Val Tyr Tyr Cys Ala Ser Leu Asp Asn Leu Asp Val
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285
```

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly
465

<210> SEQ ID NO 4
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ser Val Pro Thr Gln Val Leu Gly Leu Leu Leu Leu Trp Leu Thr
1               5                   10                  15

Asp Ala Arg Cys Gln Ser Val Val Thr Gln Pro Pro Ser Val Ser Gly
            20                  25                  30

Ala Pro Gly Gln Arg Val Thr Ile Ser Cys Ser Gly Ser Ser Ser Asn
            35                  40                  45

Val Gly Arg Asn Leu Val Tyr Trp Tyr Gln Gln Leu Pro Gly Ala Ala
    50                  55                  60

Pro Arg Leu Leu Ile Tyr Arg Asn Asn Gln Arg Pro Ser Gly Val Pro
65                  70                  75                  80

Asp Arg Phe Ser Gly Ser Lys Ser Gly Thr Ser Ala Ser Leu Ala Ile
            85                  90                  95

Ser Gly Leu Arg Ser Glu Asp Glu Ala Asp Tyr Tyr Cys Ala Val Trp
            100                 105                 110

Asp Asp Lys Leu Ser Ala Val Val Phe Gly Gly Gly Thr Lys Leu Thr
            115                 120                 125

Val Leu Gly Gln Pro Lys Ala Ala Pro Ser Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
            165                 170                 175

```
Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
            195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225             230                 235

<210> SEQ ID NO 5
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Gln Gln Ser Gly
            20                  25                  30

Ala Glu Val Lys Lys Pro Gly Ala Ser Val Lys Val Ser Cys Lys Ala
        35                  40                  45

Ser Gly Tyr Thr Phe Thr Gly Tyr Tyr Met His Trp Val Arg Gln Ala
    50                  55                  60

Pro Gly Gln Gly Leu Glu Trp Met Gly Trp Ile Asn Gly Asn Ser Gly
65                  70                  75                  80

Gly Thr Asn Tyr Ala Gln Lys Phe Gln Gly Arg Val Thr Met Thr Arg
                85                  90                  95

Asp Thr Ser Ile Ser Thr Ala Tyr Met Glu Leu Ser Arg Leu Lys Ser
            100                 105                 110

Asp Asn Thr Ala Val Tyr Tyr Cys Ala Ser Ser Gly Ser Met Asp Val
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
```

```
            290                 295                 300
Glu Val His Asn Ala Lys Thr Lys Pro Arg Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 6
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ser Val Pro Thr Gln Val Leu Gly Leu Leu Leu Leu Trp Leu Thr
1               5                   10                  15

Asp Ala Arg Cys Gln Ser Val Val Thr Gln Pro Pro Ser Val Ser Gly
            20                  25                  30

Ala Pro Gly Gln Arg Val Thr Ile Ser Cys Ser Gly Ser Ser Ser Asn
        35                  40                  45

Val Gly Arg Asn Leu Val Tyr Trp Tyr Gln Gln Leu Pro Gly Ala Ala
    50                  55                  60

Pro Arg Leu Leu Ile Tyr Arg Asn Asn Gln Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Ala Ala Trp
            100                 105                 110

Asp Asp Ser Leu Ser Gly Val Val Phe Gly Gly Gly Thr Lys Leu Thr
        115                 120                 125

Val Leu Gly Gln Pro Lys Ala Ala Pro Ser Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175
```

```
Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
            195                 200                 205

Trp Lys Ser His Arg Ser Tyr Ser Cys Gln Val Thr His Glu Gly Ser
            210                 215                 220

Thr Val Glu Lys Thr Val Ala Pro Thr Glu Cys Ser
225                 230                 235

<210> SEQ ID NO 7
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

Ala Glu Val Lys Lys Pro Gly Ala Ser Val Lys Val Ser Cys Lys Ala
            35                  40                  45

Ser Gly Tyr Thr Phe Thr Gly Tyr Tyr Met His Trp Val Arg Gln Ala
50                  55                  60

Pro Gly Gln Gly Leu Glu Trp Met Gly Trp Ile Asn Pro Asn Ser Gly
65                  70                  75                  80

Gly Thr Asn Tyr Ala Gln Lys Phe Gln Gly Arg Val Thr Met Thr Arg
                85                  90                  95

Asp Thr Ser Ile Ser Thr Ala Tyr Met Glu Leu Ser Arg Leu Arg Ser
            100                 105                 110

Asp Asp Thr Ala Val Tyr Tyr Cys Ser Ser Gly Gly Ser Met Asp Val
            115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
            210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300
```

Glu Val His Asn Ala Lys Thr Lys Pro Arg Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
        340                 345                 350

Pro Ile Glu Lys Thr Ile Ser Lys Ala Lys Gly Gln Pro Arg Glu Pro
    355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
        420                 425                 430

Thr Val Asp Lys Ser Arg Trp Gln Gln Gly Asn Val Phe Ser Cys Ser
    435                 440                 445

Val Met His Glu Ala Leu His Asn His Tyr Thr Gln Lys Ser Leu Ser
450                 455                 460

Leu Ser Pro Gly
465

<210> SEQ ID NO 8
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ser Val Pro Thr Gln Val Leu Gly Leu Leu Leu Leu Trp Leu Thr
1               5                   10                  15

Asp Ala Arg Cys Gln Ser Val Leu Thr Gln Pro Pro Ser Ala Ser Gly
            20                  25                  30

Thr Pro Gly Gln Arg Val Thr Ile Ser Cys Ser Gly Ser Ser Ser Asn
        35                  40                  45

Ile Gly Ser Asn Tyr Val Tyr Trp Tyr Gln Gln Leu Pro Gly Thr Ala
    50                  55                  60

Pro Lys Leu Leu Ile Tyr Arg Asn Asn Gln Arg Pro Ser Gly Val Pro
65                  70                  75                  80

Asp Arg Phe Ser Gly Ser Lys Ser Gly Thr Ser Ala Ser Leu Ala Ile
            85                  90                  95

Ser Gly Leu Arg Pro Glu Asp Glu Ala Asp Tyr Tyr Cys Ala Val Trp
        100                 105                 110

Asp Asp Arg Leu Ser Gly Val Val Phe Gly Gly Gly Thr Lys Leu Thr
    115                 120                 125

Val Leu Gly Gln Pro Lys Ala Ala Pro Ser Val Thr Leu Phe Pro Pro
130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
            165                 170                 175

Ser Pro Val Lys Ala Gly Val Glu Thr Thr Thr Pro Ser Lys Gln Ser

```
                    180                 185                 190
Asn Asn Lys Tyr Ala Ala Ser Ser Tyr Leu Ser Leu Thr Pro Glu Gln
            195                 200                 205

Trp Lys Ser His Arg Ser Tyr Ser Cys Gln Val Thr His Glu Gly Ser
        210                 215                 220

Thr Val Glu Lys Thr Val Ala Pro Thr Glu Cys Ser
225                 230                 235

<210> SEQ ID NO 9
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Asp Pro Lys Gly Ser Leu Ser Trp Arg Ile Leu Leu Phe Leu Ser
1               5                   10                  15

Leu Ala Phe Glu Leu Ser Tyr Gly Gln Val Gln Leu Val Gln Ser Gly
            20                  25                  30

Ala Glu Val Lys Lys Pro Gly Ala Ser Val Lys Val Ser Cys Lys Ala
        35                  40                  45

Ser Gly Tyr Thr Phe Thr Gly Tyr Tyr Met His Trp Val Arg Gln Ala
    50                  55                  60

Pro Gly Gln Gly Leu Glu Trp Met Gly Trp Ile Asn Pro Asn Ser Gly
65                  70                  75                  80

Gly Thr Asn Tyr Ala Gln Lys Phe Gln Gly Arg Val Thr Met Thr Arg
                85                  90                  95

Asp Thr Ser Ile Ser Thr Ala Tyr Met Glu Leu Ser Arg Leu Arg Ser
            100                 105                 110

Asp Asp Thr Ala Val Tyr Tyr Cys Thr Ser Gly Gly Ser Phe Asp Val
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300
```

```
Glu Val His Asn Ala Lys Thr Lys Pro Arg Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
        340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
        420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly
465

<210> SEQ ID NO 10
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ser Val Pro Thr Gln Val Leu Gly Leu Leu Leu Leu Trp Leu Thr
1               5                   10                  15

Asp Ala Arg Cys Gln Ser Val Leu Thr Gln Pro Pro Ser Ala Ser Gly
            20                  25                  30

Thr Pro Gly Gln Arg Val Thr Ile Ser Cys Ser Gly Ser Ser Ser Asn
        35                  40                  45

Ile Gly Ser Asn Tyr Val Tyr Trp Tyr Gln Gln Leu Pro Gly Thr Ala
    50                  55                  60

Pro Lys Leu Leu Ile Tyr Arg Asn Asn Gln Arg Pro Ser Gly Val Pro
65                  70                  75                  80

Asp Arg Phe Ser Gly Ser Lys Ser Gly Thr Ser Ala Ser Leu Ala Ile
            85                  90                  95

Ser Gly Leu Arg Ser Glu Asp Glu Ala Asp Tyr Tyr Cys Ala Ala Trp
        100                 105                 110

Asp Asp Arg Leu Ser Gly Ala Val Phe Gly Gly Gly Thr Lys Leu Thr
    115                 120                 125

Val Leu Gly Gln Pro Lys Ala Ala Pro Ser Val Thr Leu Phe Pro Pro
130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
            165                 170                 175

Ser Pro Val Lys Ala Gly Val Glu Thr Thr Thr Pro Ser Lys Gln Ser
        180                 185                 190
```

```
Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
        210                 215                 220

Thr Val Glu Lys Thr Val Ala Pro Thr Glu Cys Ser
225                 230                 235

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Thr Phe Thr Gly Tyr
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Gly Asn Ser Gly Gly Thr Asn
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Leu Asp Arg Arg Asp Tyr
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asn Val Gly Arg Asn Leu
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Asn Asn Gln Arg Pro Ser
1               5
```

```
<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Trp Asp Asp Ser Leu Ser Gly
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Thr Phe Thr Gly Tyr
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asn Gly Lys Ser Gly Gly Thr Asn
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Leu Asp Arg Arg Asp Tyr
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asn Val Gly Arg Asn Leu
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 21

Arg Asn Asn Gln Arg Pro Ser
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Trp Asp Asp Ser Leu Ser Gly
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Thr Phe Thr Gly Tyr
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asn Gly Asn Ser Gly Gly Thr Asn
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Leu Asp Asn Leu Asp Val
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asn Val Gly Arg Asn Leu
1               5

<210> SEQ ID NO 27
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Asn Asn Gln Arg Pro Ser
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val Trp Asp Asp Lys Leu Ser Ala
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Thr Phe Thr Gly Tyr
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asn Gly Asn Ser Gly Gly Thr Asn
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Ser Gly Ser Met Asp Val
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asn Val Gly Arg Asn Leu
```

```
<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Asn Asn Gln Arg Pro Ser
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Trp Asp Asp Ser Leu Ser Gly
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Tyr Thr Phe Thr Gly Tyr Tyr Met
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asn Pro Asn Ser Gly Gly Thr Asn
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Ser Gly Gly Gly Met Asp
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 38

Ser Ser Asn Ile Gly Ser Asn Tyr
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Asn Asn Gln Arg Pro Ser
1               5

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Trp Asp Asp Ser Leu Ser Gly Val Val
1               5                   10

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Tyr Thr Phe Thr Gly Tyr Tyr Met
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asn Pro Asn Ser Gly Gly Thr Asn
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Ser Gly Gly Ser Met Asp
1               5

<210> SEQ ID NO 44

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Ser Asn Ile Gly Ser Asn Tyr
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Asn Asn Gln Arg Pro Ser
1               5

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Val Trp Asp Asp Arg Leu Ser Gly Val Val
1               5                   10

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Tyr Thr Phe Thr Gly Tyr Tyr Met
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asn Pro Asn Ser Gly Gly Thr Asn
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49
```

```
<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Ser Asn Ile Gly Ser Asn Tyr
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Asn Asn Gln Arg Pro Ser
1               5

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Trp Asp Asp Arg Leu Ser Gly Ala Val
1               5                   10

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 53

His His His His His His
1               5
```

Preceding sequence (top of page):

```
Thr Ser Gly Gly Ser Phe Asp
1               5
```

ADAM17 BINDING MOLECULES AND USES THEREOF

CROSS-REFERENCE TO RELATED APPLICATIONS

This application claims the benefit of priority of U.S. Provisional Patent Application No. 62/815,471 filed on Mar. 8, 2019, the content of which is hereby incorporated by reference in its entirety.

STATEMENT OF GOVERNMENT SUPPORT

This invention was made with government support under grant number CA185930 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 4, 2020, is named MSKCC_029_WO1_SL.txt and is 41,093 bytes in size.

INCORPORATION BY REFERENCE

For the purposes of only those jurisdictions that permit incorporation by reference, all of the references cited in this disclosure are hereby incorporated by reference in their entireties (numbers in parentheses or in superscript following text in this patent disclosure refer to the numbered references provided in the "Reference List" section of this patent specification). In addition, any manufacturers' instructions or catalogues for any products cited or mentioned herein are incorporated by reference. Documents incorporated by reference into this text, or any teachings therein, can be used in the practice of the present invention.

BACKGROUND

ADAM proteases consist of an N-terminal pro-sequence followed by metalloprotease (M), disintegrin (D), cysteine-rich (C), transmembrane, and cytoplasmic domains (5). The substrate specificity of ADAM proteases is not imparted by a typical substrate cleavage signature but relies on noncatalytic interactions between the substrate and the ADAM D+C domains (1, 6-9). Signaling by the ErbB family regulates proliferation, survival, differentiation and motility during normal and oncogenic development (10). The four major ErbB family members are Her1 (also known as EGFR or ErbB1), Her2 (also referred to as Neu or ErbB2), Her3 (also referred to as ErbB3), and Her4. ErbB family ligands are initially cell-surface tethered, and proteolytic release of their precursors by ADAM proteases (11) is a key regulatory switch to trigger ErbB family signaling (9), underlying the downstream autocrine signaling that drives tumor progression (12-14). The ErbBs display de-regulated signaling in many human cancers due to overexpression and/or mutations, including in some of the most intractable and common cancers, with EGFR and ErbB2 prominent in breast, colon, glioma and lung cancer amongst others (10). ADAM17-dependent EGFR transactivation provides the autocrine activation loop that underlies the growth factor independence of many tumors (15,16). In addition, ADAM17-mediated cleavage of ErbB2/ErbB4 in tumors is associated with constitutive receptor activity and poor prognosis, and undermines receptor-targeted therapies (17,18).

To date, inhibitors of the catalytic active site of ADAM17 have not been successful in clinical trials due to lack of specificity (for example due to the similarity of the ADAM17 catalytic site with those of matrix metalloproteinases.), lack of efficacy, and dose-limiting toxicity (19-21). As such, there is a need in the art for new and improved strategies for ADAM17 inhibition. The present invention addresses this need.

SUMMARY OF THE INVENTION

Recent studies have shown that the ADAM17 substrate recognition domain is located outside of the catalytic domain (1-4) raising the possibility that this substrate recognition domain could provide a novel target for development of inhibitors—potentially avoiding adverse side effects associated with targeting the ADAM17 catalytic domain. The present invention provides novel ADAM17 antibodies that bind to this substrate recognition domain. Such antibodies may be useful in the treatment of a variety of different solid tumors.

As described further in the Examples section of the patent specification, a large human phage display "Fab" library was screened to identify Fabs that bind to the ADAM substrate-binding domain. Two highly specific anti-ADAM17 Fabs were identified—termed D5 and D8. The Fabs were selected by ELISA-based screening and their specificities to the ADAM substrate-binding domain were confirmed. Cross-reactivity of these Fabs with the substrate-binding domains of closely related ADAMs, such as ADAM10 and ADAM19, was evaluated and it was found that these two Fabs specifically recognized the ADAM17 substrate-binding domain. These two Fabs were reformatted to a human IgG1 framework and the resulting monoclonal antibodies (mAbs) were tested for their effects on triple-negative human breast cancer cells. It was found that both mAbs significantly inhibited proliferation of these human breast cancer cells via inhibition of ADAM17-dependent ErbB/EGFR signaling. Affinity-maturation libraries of D8 and D5 were constructed by targeted mutagenesis. After 3 rounds of selection a panel of 17 affinity matured clones derived from D5 and D8 were selected based on sequencing results, and based on their $EC_{50}$ and $K_d$ values. These affinity-matured Fabs were also reformatted to a human IgG1 framework and tested in functional assays. Five of the affinity-matured clones were found to inhibit proliferation of triple negative breast cancer cells with $IC_{50}$ values 5 to 10-fold lower than those of the parental D5 and D8 clones—making them ideal candidates for therapeutic applications. These novel anti-ADAM17 antibodies and Fab fragments, as well as a variety of other ADAM17 binding molecules containing binding determinants (e.g. complementarity determining regions or CDRs) and/or variable domains derived from those present in these antibodies and Fabs, are further described herein. Uses of such ADAM17 binding molecules are also described herein.

Accordingly, in certain embodiments the present invention provides the affinity matured anti-ADAM17 antibodies referred to herein as "D5. Pl. A4," "D5. P2. A11," "D5. P2. B3," "D8. Pl. C1," and "D8. P2. C6," as well as various antigen binding fragments of these antibodies.

For example, in one embodiment, the present invention provides an isolated ADAM17 binding molecule comprising a heavy chain variable region comprising: a CDR H1 domain comprising SEQ ID NO. 17, a CDR H2 domain comprising SEQ ID NO. 18, and a CDR H3 domain comprising SEQ ID NO. 19, and a light chain variable region comprising: a CDR L1 domain comprising SEQ ID NO. 20, a CDR L2 domain comprising SEQ ID NO. 21, a CDR L3 domain comprising SEQ ID NO. 22—i.e. the CDRs of D5.P1.A4. (Each of these sequences, and all other sequences referred to herein using a sequence identification number (i.e. a "SEQ ID NO.") is provided in Table 1 and/or Table 2 of the "Detailed Description" section of this patent disclosure.)

In another embodiment, the present invention provides an isolated ADAM17 binding molecule comprising a heavy chain variable region comprising: a CDR H1 domain comprising SEQ ID NO. 23, a CDR H2 domain comprising SEQ ID NO. 24, and a CDR H3 domain comprising SEQ ID NO. 25, and a light chain variable region comprising: a CDR L1 domain comprising SEQ ID NO. 26, a CDR L2 domain comprising SEQ ID NO. 27, a CDR L3 domain comprising SEQ ID NO. 28—i.e. the CDRs of D5.P2.A11.

In another embodiment, the present invention provides an isolated ADAM17 binding molecule comprising a heavy chain variable region comprising: a CDR H1 domain comprising SEQ ID NO. 29, a CDR H2 domain comprising SEQ ID NO. 30, and a CDR H3 domain comprising SEQ ID NO. 31, and a light chain variable region comprising: a CDR L1 domain comprising SEQ ID NO. 32, a CDR L2 domain comprising SEQ ID NO. 33, a CDR L3 domain comprising SEQ ID NO. 34—i.e. the CDRs of D5.P2.B3.

In another embodiment, the present invention provides an isolated ADAM17 binding molecule comprising a heavy chain variable region comprising: a CDR H1 domain comprising SEQ ID NO. 41, a CDR H2 domain comprising SEQ ID NO. 42, and a CDR H3 domain comprising SEQ ID NO. 43, and a light chain variable region comprising: a CDR L1 domain comprising SEQ ID NO. 44, a CDR L2 domain comprising SEQ ID NO. 45, a CDR L3 domain comprising SEQ ID NO. 46—i.e. the CDRs of D8.P1.C1.

In another embodiment, the present invention provides an isolated ADAM17 binding molecule comprising a heavy chain variable region comprising: a CDR H1 domain comprising SEQ ID NO. 47, a CDR H2 domain comprising SEQ ID NO. 48, and a CDR H3 domain comprising SEQ ID NO. 49, and a light chain variable region comprising: a CDR L1 domain comprising SEQ ID NO. 50, a CDR L2 domain comprising SEQ ID NO. 51, a CDR L3 domain comprising SEQ ID NO. 52—i.e. the CDRs of D8.P2.C6.

In another embodiment, the present invention provides an isolated ADAM17 binding molecule comprising a heavy chain variable region comprising amino acids 25-139 of SEQ ID NO. 1, and a light chain variable region comprising amino acids 21-136 of SEQ ID NO. 2—i.e. the variable regions of D5.P1. A4.

In another embodiment, the present invention provides an isolated ADAM17 binding molecule comprising a heavy chain variable region comprising amino acids 25-139 of SEQ ID NO. 3, and a light chain variable region comprising amino acids 21-136 of SEQ ID NO. 4—i.e. the variable regions of D5.P2.A11.

In another embodiment, the present invention provides an isolated ADAM17 binding molecule comprising a heavy chain variable region comprising amino acids 25-139 of SEQ ID NO. 5, and a light chain variable region comprising amino acids 21-136 of SEQ ID NO. 6—i.e. the variable regions of D5.P2.B3.

In another embodiment, the present invention provides an isolated ADAM17 binding molecule comprising a heavy chain variable region comprising amino acids 25-139 of SEQ ID NO. 7, and a light chain variable region comprising amino acids 21-136 of SEQ ID NO. 8—i.e. the variable regions of D8.P1.C1.

In another embodiment, the present invention provides an isolated ADAM17 binding molecule comprising a heavy chain variable region comprising amino acids 25-139 of SEQ ID NO. 9, and a light chain variable region comprising amino acids 21-136 of SEQ ID NO. 10—i.e. the variable regions of D8.P2.C6.

In another embodiment, the present invention provides an isolated ADAM17 binding molecule comprising a heavy chain comprising SEQ ID NO. 1 and a light chain comprising SEQ ID NO. 2—i.e. the full length IgG of D5.P1. A4.

In another embodiment, the present invention provides an isolated ADAM17 binding molecule comprising a heavy chain comprising SEQ ID NO. 3 and a light chain comprising SEQ ID NO. 4—i.e. the full length IgG of D5.P2.A11.

In another embodiment, the present invention provides an isolated ADAM17 binding molecule comprising a heavy chain comprising SEQ ID NO. 5 and a light chain comprising SEQ ID NO. 6—i.e. the full length IgG of D5.P2.B3.

In another embodiment, the present invention provides an isolated ADAM17 binding molecule comprising a heavy chain comprising SEQ ID NO. 7 and a light chain comprising SEQ ID NO. 8—i.e. the full length IgG of D8.P1.C1.

In another embodiment, the present invention provides an isolated ADAM17 binding molecule comprising a heavy chain comprising SEQ ID NO. 9 and a light chain comprising SEQ ID NO. 10—i.e. the full length IgG of D8.P2.C6.

In other embodiments, the present invention also provides isolated ADAM17 binding molecules that are able to specifically bind to the same epitope on human ADAM17 as any one of the ADAM17 binding molecules described above. Similarly, in some embodiments the present invention provides isolated ADAM17 binding molecules that are able to compete with any one of the ADAM17 binding molecules described above for binding to human ADAM17.

In some embodiments, the ADAM17 binding molecules of the invention (such as those described above) are antibodies. For example, in some embodiments an ADAM17 binding molecule of the invention may be a humanized antibody, a fully human antibody, a murine antibody, a chimeric antibody, a monoclonal antibody, a polyclonal antibody, a bi-specific antibody, or a multi-specific antibody.

In some embodiments, the ADAM17 binding molecules of the invention (such as those described above) are, or comprise, antibody fragments. For example, in some embodiments an ADAM17 binding molecule of the invention may be a Fv, a Fab, a F(ab')2, a Fab', a dsFv fragment, a single chain Fv (scFV), an sc(Fv)2, a disulfide-linked (dsFv), a diabody, a triabody, a tetrabody, a minibody, or a single chain antibody.

In those embodiments where an ADAM 17 binding molecule of the invention comprises a heavy chain constant region, or a portion thereof, the heavy-chain constant region may be an alpha, delta, epsilon, gamma, or mu heavy chain constant region. Similarly, in some embodiments, the ADAM17 binding molecules of the invention (such as those described above) may be, or may comprise, an IgA, IgD, IgE, IgG or IgM class immunoglobulin molecule.

In those embodiments where an ADAM 17 binding molecule of the invention comprises a light chain constant region, or a portion thereof, the light-chain constant region may a lambda light chain constant region or a kappa light chain constant region.

In addition to the various ADAM17 binding molecules described above, in some embodiments the present invention also provides composition comprising such ADAM17 binding molecules, for example pharmaceutical compositions.

In further embodiments the present invention also provides host cells that produce an ADAM17 binding molecule as described herein, such as mammalian cells (including human and murine cells).

In yet further embodiments the present invention also provides nucleotide sequences that encode an ADAM17 binding molecule as described above, as well as vectors and host cells (including human and murine host cells) comprising such nucleotide sequences.

The present invention also provides various different methods of use of the ADAM17 binding molecules described herein.

For example, in some embodiments the present invention provides methods for inhibiting the proliferation of, and/or killing, tumor cells. Such methods involve delivering an effective amount of an ADAM17 binding molecule or composition (such as pharmaceutical composition), as described herein, to tumor cells. In other embodiments, the present invention provides methods for inhibiting an ADAM17 biological activity in cells or in a tissue. Such biological activities include, but are not limited to, (a) binding of ADAM17 to an ADAM17 substrate, (b) proteolytic cleavage of an ADAM17 substrate by ADAM17, (c) activation of an ADAM17 substrate, and (d), signaling by an ADAM17 substrate. Such methods involve delivering an effective amount of an ADAM17 binding molecule to cells or a tissue that expresses or contains ADAM17.

In each of the above methods the tumor cells may be breast cancer cells, colon cancer cells, lung cancer cells, non-small cell lung cancer cells, brain cancer cells, glioma cells, glioblastoma cells, neuroblastoma cells, stomach cancer cells, pancreatic cancer cells, ovarian cancer cells, prostate cancer cells, and kidney cancer cells. In some of such methods the tumor cells are triple-negative breast cancer cells. In some of such methods the tumor cells overexpress, or exhibit over-activity of, an ErbB family member or a ligand of an ErbB family member (such as Her1 (EGFR/Her1/ErbB1), Her2 (Neu, ErbB2), Her3 (ErbB3), or Her4 (ErbB4). In some of such methods the tumor cells are in vitro, while in other methods the tumor cells are in vivo. In those methods relating to an ADAM17 substrate, the ADAM17 substrate may be a ligand of an ErbB family member, such as Her1 (EGFR/Her1/ErbB1), Her2 (Neu, ErbB2), Her3 (ErbB3), or Her4 (ErbB4).

The present invention also provides various methods of treating cancer in living subjects, such as mammalian subjects—including humans. Such methods involve administering an effective amount of an ADAM17 binding molecule as described herein, or a composition (such as a pharmaceutical composition) containing such an ADAM17 binding molecule, to a subject that has cancer. In some of such methods the subject has breast cancer, colon cancer, lung cancer, non-small cell lung cancer, brain cancer, a glioma, a glioblastoma, a neuroblastoma, stomach cancer, pancreatic cancer, ovarian cancer, prostate cancer, or kidney cancer. In some embodiments the subject has triple-negative breast cancer. In some embodiments the subject has a cancer/tumor containing tumor cells that overexpress, or exhibit over-activity of, an ErbB family member or an ErbB family member ligand. Such ErbB family members include Her1 (EGFR/Her1/ErbB1), Her2 (Neu, ErbB2), Her3 (ErbB3), and Her4. Some of such treatment methods also involve administering an additional active agent to the subject—i.e. in addition to the ADAM17 binding molecule. Such additional active agents include chemotherapeutic agents, antibodies, and antibody fragments. Exemplary additional agents include, but are not limited to, afatinib, actinomycin, azacitidine, azathioprine, bevacizumab, bleomycin, bortezomib, carboplatin, capecitabine, cetuximab, cisplatin, chlorambucil, cyclophosphamide, cytarabine, daunorubicin, docetaxel, doxifluridine, doxorubicin, epirubicin, epothilone, erlotinib, etoposide, fluorouracil, gefitinib, gemcitabine, hydroxyurea, idarubicin, imatinib, irinotecan, mechlorethamine, mercaptopurine, methotrexate, mitoxantrone, olaparib, oxaliplatin, paclitaxel, panitumab, pazopanib, pemetrexed, poly(ADP-ribose) polymerase (PARP) inhibitors, tamoxifen, teniposide, tioguanine, topotecan, trastuzumab, tretinoin, valrubicin, vinblastine, vincristine, vindesine, vinorelbine, and vintafolide.

The present invention also provides methods for detecting ADAM17 in a sample—such as a cell or tissue sample. Such tissue samples may be obtained from a living subject (e.g. biopsy samples). Such methods typically involve contacting the sample with an ADAM17 binding molecule according as described herein, and detecting binding of the ADAM17 binding molecule to ADAM17.

The present invention also provides methods for method of determining whether a subject with a tumor is a candidate for treatment with an ADAM17 binding molecule. Some of such methods involve contacting a tumor sample from a subject (or cells therefrom) with an ADAM17 binding molecule as described herein, and performing an assay to determine whether the ADAM17 binding molecule binds to ADAM17 in the sample, whereby if the ADAM17 binding molecule binds to ADAM17 in the sample the subject may be a candidate for treatment with one of the ADAM17 binding molecules described herein. Other such methods involve contacting a tumor sample from a subject (or cells therefrom) with an ADAM17 binding molecule as described herein, and performing an assay to determine whether the ADAM17 binding molecule inhibits proteolytic cleavage of an ADAM17 substrate in the sample, or inhibits activation of or signaling of an ADAM17 substrate in the sample, whereby if the ADAM17 binding molecule inhibits one of such activities, the subject may be a candidate for treatment with an ADAM17 binding molecule as described herein. In each of such methods, if the subject is determined to be a candidate for therapy, the subject may subsequently be treated by administering an effective amount of an ADAM17 binding molecule as described herein.

In each of the above methods the tumor cells may be breast cancer cells, colon cancer cells, lung cancer cells, non-small cell lung cancer cells, brain cancer cells, glioma cells, glioblastoma cells, neuroblastoma cells, stomach cancer cells, pancreatic cancer cells, ovarian cancer cells, prostate cancer cells, and kidney cancer cells. In some of such methods the tumor cells are triple-negative breast cancer cells. In some of such methods the tumor cells overexpress, or exhibit over-activity of, an ErbB family member or a ligand of an ErbB family member (such as Her1 (EGFR/Her1/ErbB1), Her2 (Neu, ErbB2), Her3 (ErbB3), or Her4 (ErbB4). In some of such methods the tumor cells are in vitro, while in other methods the tumor cells are in vivo. In those methods relating to an ADAM17 substrate, the ADAM17 substrate may be a ligand of an ErbB family member, such as Her1 (EGFR/Her1/ErbB1), Her2 (Neu, ErbB2), Her3 (ErbB3), or Her4 (ErbB4).

These and other embodiments of the invention are further described in the "Brief Description of the Figures," "Detailed Description," "Examples," "Figures," and "Claims" sections of this patent disclosure, each of which sections is intended to be read in conjunction with, and in the context of, all other sections of the present patent disclosure. Furthermore, one of skill in the art will recognize that the various embodiments of the present invention described herein can be combined in various different ways, and that such combinations are within the scope of the present invention.

BRIEF DESCRIPTION OF THE FIGURES

FIG. 2A-D. Results of experiments performed using the human breast cancer cell line MDA-MB-231. FIG. 2A shows the results of experiments in which the effects of various anti-ADAM17 antibodies or antibody fragments on viability of MDA-MB-231 breast cancer cells were tested using an ALAMARBLUE cell viability assay. The effects of D5 IgG, D5 Fab, D8 IgG, and D8 Fab were tested. The control was an IgG1 control. GM6001 is a matrix metalloprotease inhibitor. FIG. 2A provides the results of these experiments in a bar graph. FIGS. 2B-D provide the results of experiments in which cultured MDA-MB-231 cells were stained with the anti-ADAM17 antibodies D5 and D8 and an alexa568-labelled anti-human IgG secondary antibody (green). As a control cells were stained with the secondary antibody only. Nuclei were stained with Hoechst (blue) before imaging by confocal microscopy. Microscopy images of the D5 (FIG. 2B), D8 (FIG. 2C), and control (FIG. 2D) stained MDA-MB-231 cells are shown, respectively.

Figure 13A:
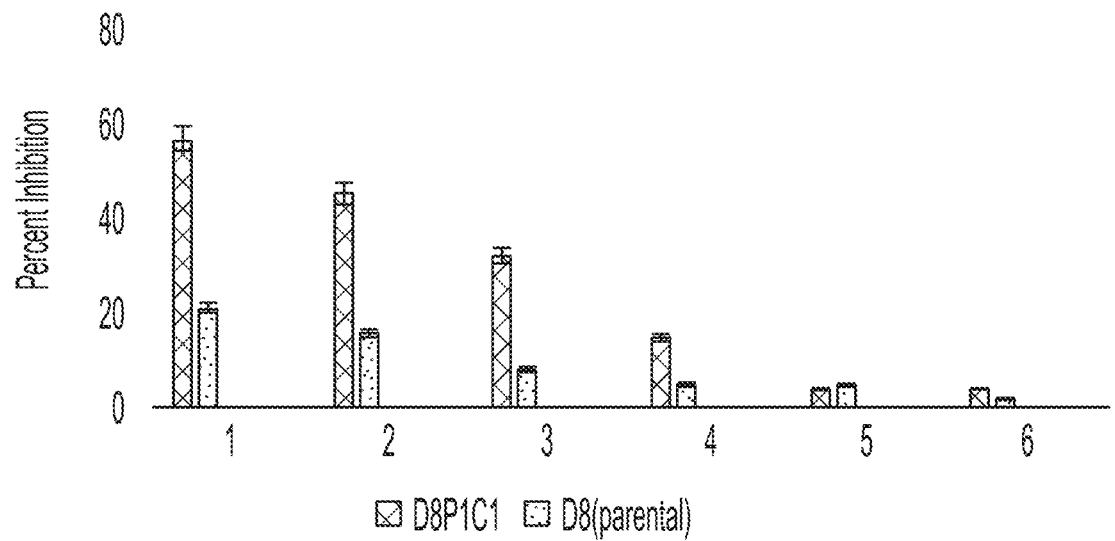
FIG. 13A-B. Proliferation inhibition of the glioblastoma cell line U87 MG by the anti-ADAM17 mAbs, D8 (FIG.
Figure 13B:
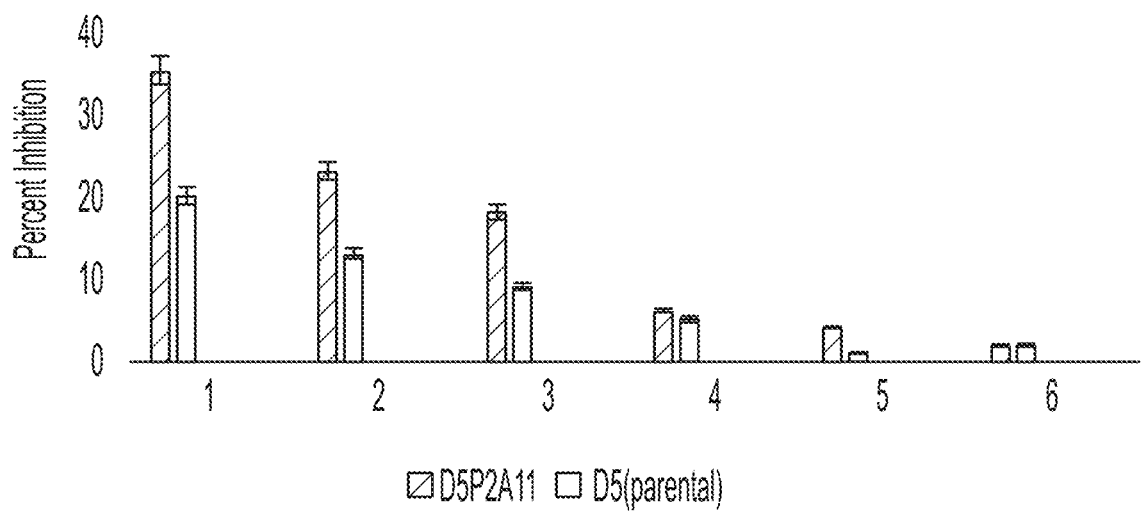

13A), D5 (FIG. 13B) and their affinity-matured versions D8P1C1 (FIG. 13A), D5P2A11 (FIG. 13B). Data sets 1-6 were generated using different concentrations of the specified mAbs, as follows: 1: 20 µg/ml; 2:10 µg/ml; 3: 5 µg/ml; 4: 2.5 µg/ml; 5: 1.25 µg/ml; 6: 0.625 µg/ml.

Figure 14:
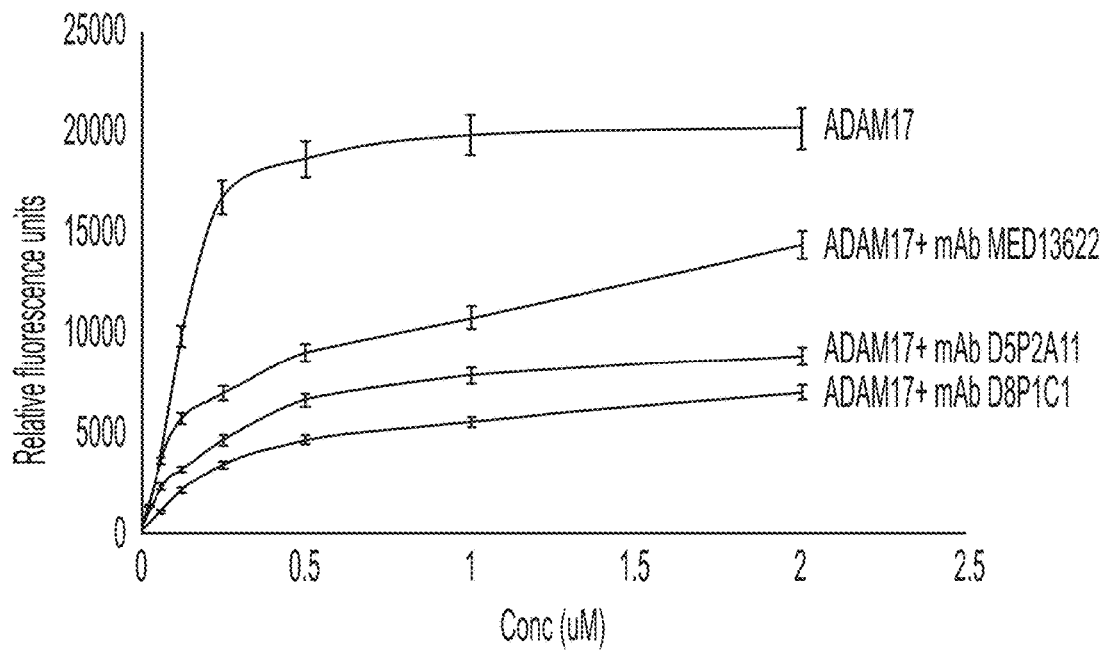

FIG. 14. Data from FRET based peptide cleavage assays. A peptide substrate of ADAM17 derived from TNF-alpha was used. The excitation wavelength was 320 nm and the emission wavelength was 405 nm. The buffer contained 20 mM Tris pH 8.8, Zinc chloride 2 µM, and the peptide substrate at 50 µM. The data in the graph is the mean of triplicate determinations. The maximum dispersion was within 10% of the mean value.

Figure 15:
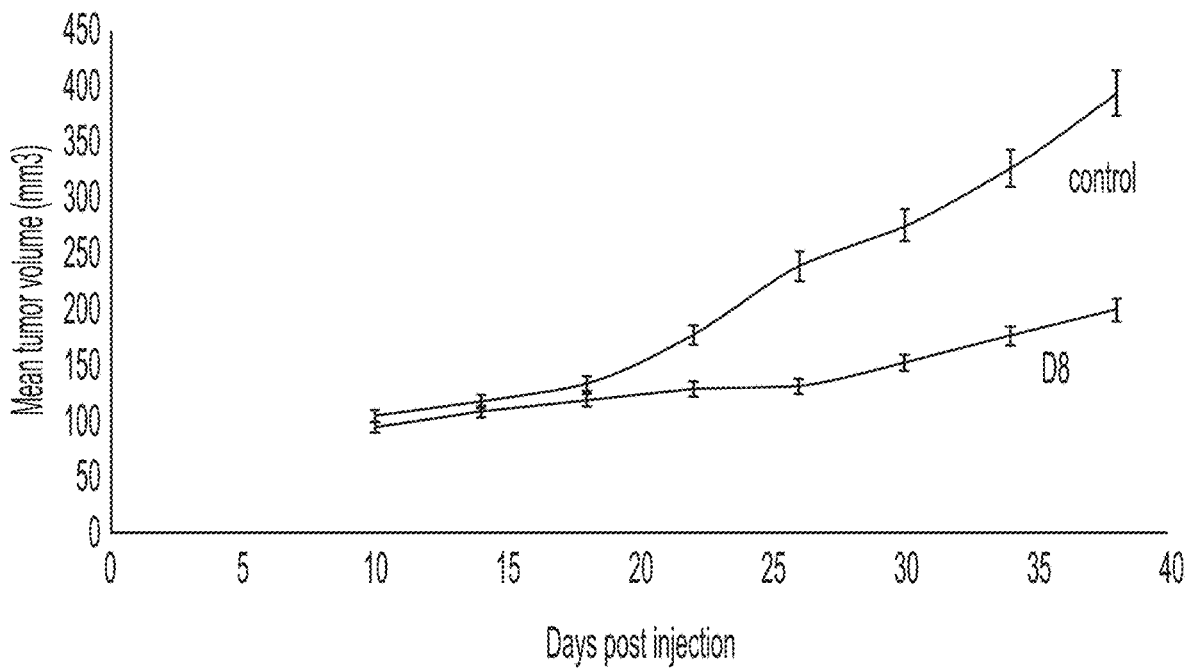

FIG. 15. Data showing anti-tumor effect of the mAb D8P1C1 in triple-negative breast cancer xenograft assay. 6-8 weeks old athymic nude mouse (n=5) were each injected with 10 million MDA-MB-231 cells per mouse. In the treatment group ("D8" on the graph) each mouse was injected with D8P1C1 (i.p.) at a dose of 15 mg/kg, biweekly for 4 weeks. In the control group PBS was used as the vehicle control ("control" on the graph). Mean tumor volume was measured for the control and treatment groups. The graph shows mean tumor volume ($mm^3$) plotted against days post-injection. The percent (%) inhibition of tumor growth by D8P1C1 on the final day of the study was 76.8 percent (calculated as 100×[1−[(TreatedFinal day−TreatedDay 1)/(ControlFinal day−ControlDay 1)]]).

Figure 16:
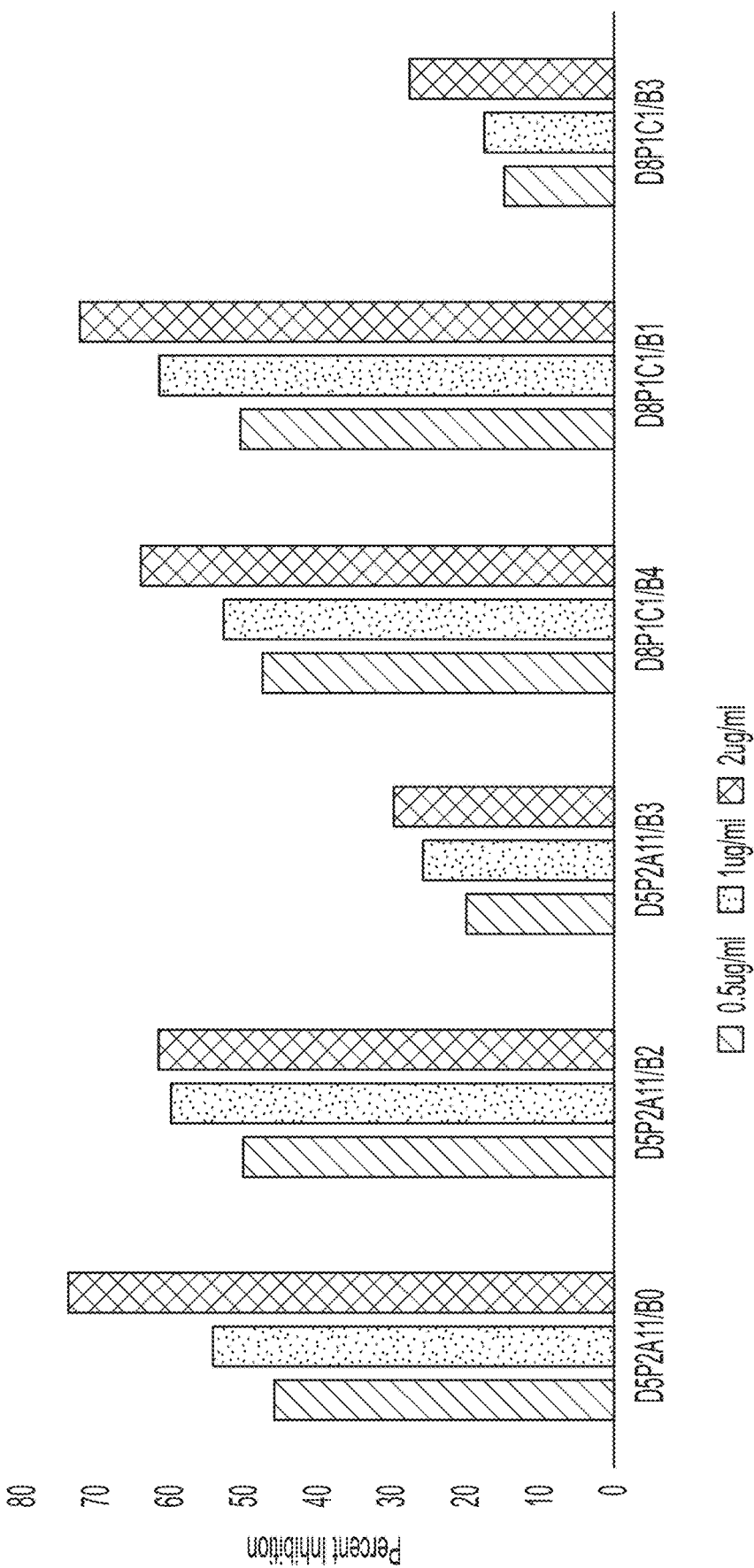

FIG. 16. Formulation & Buffer Optimization. Affinity matured antibodies were prepared in one of 5 buffer formulations denoted B0, B1, B2, B3, and B4 (see Example 5 for details of each buffer). The effect of each antibody formulation on inhibition of proliferation of MDA-MB-231 cells was then tested using the same methodology as was used to generate the data presented in FIG. 4. The results of these experiments are shown herein with % inhibition of MDA-MB-231 cell proliferation shown for various antibody/buffer combinations (as denoted in the figure). Each antibody/buffer combination was tested at 0.5 µg/ml (left-hand bars from), 1.0 µg/ml (middle bars) and 2.0 µg/ml (right-hand bars).

DETAILED DESCRIPTION

Some of the main embodiments of the present invention are described in the "Summary of the Invention," "Examples," "Brief Description of the Figures," and "Figures" sections of this patent disclosure. This Detailed Description section provides certain additional description and details and is intended to be read in conjunction with all other sections of the present patent disclosure.

The present invention provides molecules that bind to ADAM17—referred to herein as "ADAM17 binding molecules". Such ADAM17 binding molecules are antibodies, or antigen-binding fragments thereof, which specifically bind to ADAM17.

Polynucleotides that encode the ADAM17 binding molecules described herein, as well as compositions comprising the ADAM17 binding molecules, and methods of making the ADAM17 binding molecules, are also provided.

Methods of using the novel ADAM17 binding molecules described herein are also provided, such as methods of treating cancer and/or inhibiting proliferation of cancer cells.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, e.g., Ausubel et al. eds. (2015) *Current Protocols in Molecular Biology* (John Wiley and Sons); Greenfield, ed. (2013) *Antibodies: A Laboratory Manual* (2nd ed., Cold Spring Harbor Press); Green and Sambrook, eds. (2012), *Molecular Cloning: A Laboratory Manual* (4th ed., Cold Spring Harbor Laboratory Press); Krebs et al., eds. (2012) *Lewin's Genes XI* (11th ed., Jones & Bartlett Learning); Freshney (2010) *Culture Of Animal Cells* (6th ed., Wiley); Weir and Blackwell, eds., (1996) *Handbook Of Experimental Immunology*, Volumes I-IV (5th ed., Wiley-Blackwell); Borrebaeck, ed. (1995) *Antibody Engineering* (2nd ed., Oxford Univ. Press); Glover and Hames, eds., (1995) *DNA Cloning: A Practical Approach, Volumes I and II* (2nd ed., IRL Press); Rees et al., eds. (1993) *Protein Engineering: A Practical Approach* (1st ed., IRL Press); Mayer and Walker, eds. (1987) *Immunochemical Methods In Cell And Molecular Biology* (Academic Press, London); Nisonoff (1984)*Introduction to Molecular Immunology* (2nd ed., Sinauer Associates, Inc.); and Steward (1984) *Antibodies: Their Structure and Function* (1st ed., Springer Netherlands).

In order that the present invention can be more readily understood, certain terms are first defined. Additional definitions are set forth throughout the disclosure. Unless defined otherwise, all technical and scientific terms used herein have the same meaning as commonly understood by one of ordinary skill in the art to which this invention is related. For example, *The Dictionary of Cell and Molecular Biology* (5th ed. J. M. Lackie ed., 2013), the *Oxford Dictionary of Biochemistry and Molecular Biology* (2d ed. R. Cammack et al. eds., 2008), and *The Concise Dictionary of Biomedicine and Molecular Biology* (2d ed. P-S. Juo, 2002) can provide one of skill with general definitions of some terms used herein.

I. Definitions & Abbreviations

As used in this specification and the appended claims, the singular forms "a," "an," and "the" include plural referents, unless the context clearly dictates otherwise. The terms "a" (or "an") as well as the terms "one or more" and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Units, prefixes, and symbols are denoted in their Système International de Unites (SI) accepted form. Numeric ranges provided herein are inclusive of the numbers defining the range.

Where a numeric term is preceded by "about" or "approximately," the term includes the stated number and values±10% of the stated number.

Numbers in parentheses or superscript following text in this patent disclosure refer to the numbered references provided in the "Reference List" section at the end of this patent disclosure.

Wherever embodiments are described with the language "comprising," otherwise analogous embodiments described in terms of "consisting of" and/or "consisting essentially of" are included.

Amino acids are referred to herein by their commonly known three-letter symbols or by the one-letter symbols recommended by the IUPAC-IUB Biochemical Nomenclature Commission. Nucleotides, likewise, are referred to by their commonly accepted single-letter codes.

The term "antibody" refers to an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. The terms "antibody" or "immunoglobulin" are used interchangeably herein.

A typical antibody comprises at least two heavy (H) chains and two light (L) chains interconnected by disulfide bonds. Each heavy chain is comprised of a heavy chain variable region (abbreviated herein as VH) and a heavy chain constant region. The heavy chain constant region is comprised of three domains, CH1, CH2, and CH3. Each light chain is comprised of a light chain variable region (abbreviated herein as VL) and a light chain constant region (CL). The light chain constant region is comprised of one domain, Cl. The variable regions of the heavy and light chains contain a binding domain that interacts with an antigen. The constant regions of the antibodies can mediate the binding of the immunoglobulin to host tissues or factors, including various cells of the immune system (e.g. effector cells) and the first component (C1q) of the classical complement system.

Antibodies can be of any the five major classes of immunoglobulins: IgA, IgD, IgE, IgG and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu respectively. The different classes of immunoglobulins have different and well-known subunit structures and three-dimensional configurations. There are two classes of mammalian light chains, lambda and kappa. I The VH and VL regions can be further subdivided into regions of hypervariability, termed complementarity-determining regions (CDRs), interspersed with regions that are more conserved, termed framework (FW) regions. The CDRs in each chain are held together in close proximity by the FW regions and, with the CDRs from the other chain, contribute to the formation of the antigen-binding site of antibodies. Each VH and VL is composed of three CDRs and four FW regions, arranged from amino-terminus to carboxy-terminus in the following order: FW1, CDR1, FW2, CDR2, FW3, CDR3, FW4.

There are at least two techniques for determining CDRs: (1) an approach based on cross-species sequence variability (Kabat et al., Sequences of Proteins of Immunological Interest, 5th Ed. Public Health Service, National Institutes of Health, Bethesda, Md. (1991)); and (2) an approach based on crystallographic studies of antigen-antibody complexes (Al-lazikani et al., J. Molec. Biol. 273:927-948 (1997)). In addition, combinations of these two approaches are sometimes used in the art to determine CDRs.

The amino acid position numbering as in Kabat, refers to the numbering system used for heavy chain variable domains or light chain variable domains (approximately residues 1-107 of the light chain and residues 1-113 of the heavy chain). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a, according to Kabat) after residue 52 of H2 and inserted residues (e.g., residues 82a, 82b, and 82c, etc., according to Kabat) after heavy chain FW residue 82.

The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. See Table 1.

IMGT (ImMunoGeneTics) also provides a numbering system for the immunoglobulin variable regions, including the CDRs. See, e.g., Lefranc, M. P. et al., Dev. Comp. Immunol. 27: 55-77 (2003). The IMGT numbering system was based on an alignment of more than 5,000 sequences, structural data, and characterization of hypervariable loops and allows for easy comparison of the variable and CDR regions for all species. According to the IMGT numbering schema VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

As used throughout the specification, the CDRs sequences described herein are numbered using the Kabat numbering system.

As used herein, the term "antibody" encompasses polyclonal antibodies; monoclonal antibodies; multispecific antibodies, such as bispecific antibodies generated from at least two intact antibodies; humanized antibodies; human antibodies; chimeric antibodies; fusion proteins comprising an antigen-determination portion of an antibody; and any other modified immunoglobulin molecule comprising an antigen recognition site, so long as the antibodies exhibit the desired biological activity.

A "monoclonal antibody" (mAb) refers to a homogeneous antibody population that is involved in the highly specific recognition and binding of a single antigenic determinant, or epitope. This is in contrast to polyclonal antibodies, which typically include different antibodies directed against different antigenic determinants. The term "monoclonal" can apply to both intact and full-length monoclonal antibodies, as well as to antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals.

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, or hamster) that have the desired specificity, affinity, and capability (Jones et al., 1986, Nature, 321:522-525; Riechmann et al., 1988, Nature, 332:323-327; Verhoeyen et al., 1988, Science, 239:1534-1536). In some instances, the Fv framework region (FW) residues of a human immunoglobulin are replaced with the corresponding residues in an antibody from a non-human species that has the desired specificity, affinity, and capability.

Humanized antibodies can be further modified by the substitution of additional residues either in the Fv framework region and/or within the replaced non-human residues to refine and optimize antibody specificity, affinity, and/or capability. In general, humanized antibodies will comprise substantially all of at least one, and typically two or three, variable domains containing all or substantially all of the CDR regions that correspond to the non-human immunoglobulin whereas all or substantially all of the FR regions are those of a human immunoglobulin consensus sequence. Humanized antibody can also comprise at least a portion of an immunoglobulin constant region or domain (Fc), typically that of a human immunoglobulin. Examples of methods used to generate humanized antibodies are described in U.S. Pat. Nos. 5,225,539 and 5,639,641.

The term "human antibody" means an antibody produced by a human or an antibody having an amino acid sequence corresponding to an antibody produced by a human made using any technique known in the art. The definition of a human antibody includes intact or full-length antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

The term "antigen-binding fragment" refers to a portion of an intact antibody comprising the complementarity determining variable regions of the antibody. Examples of antibody fragments that can constitute an "antigen-binding fragment" include, but are not limited to, Fab, Fab', F(ab')2, and Fv fragments, linear antibodies, single chain antibodies (e.g., ScFvs), and multi-specific antibodies formed from antibody fragments.

A "blocking" antibody or an "antagonist" antibody is one that inhibits or reduces biological activity of the antigen it binds, such as ADAM17. In certain aspects, blocking antibodies or antagonist antibodies substantially or completely inhibit the biological activity of the antigen. Desirably, the biological activity is reduced by 10%, 20%, 30%, 50%, 70%, 80%, 90%, 95%, or even 100%.

The term "germlining" means that amino acids at specific positions in an antibody are mutated back to those in the germ line.

The "IgG1 triple mutant" or "IgG1-TM" antibody format is a human IgG1 isotype containing three single amino acid substitutions, L234F/L235E/P331S, within the lower hinge and CH2 domain (Oganesyan et al., Acta Crystallogr. D Biol. Crystallogr. 64:700-704, 2008). The TM causes a profound decrease in binding to human FcγRI, FcγRII, FcγRIII, and C1q, resulting in a human isotype with very low effector function.

The terms "YTE" or "YTE mutant" or "YTE mutation" refer to a mutation in IgG1 Fc that results in an increase in the binding to human FcRn and improves the serum half-life of the antibody having the mutation. A YTE mutant comprises a combination of three mutations, M252Y/S254T/T256E (EU numbering Kabat et al. (1991) Sequences of Proteins of Immunological Interest, U.S. Public Health Service, National Institutes of Health, Washington, D.C.), introduced into the heavy chain of an IgG1. See U.S. Pat. No. 7,658,921, which is incorporated by reference herein. The YTE mutant has been shown to increase the serum half-life of antibodies approximately four-times as compared to wild-type versions of the same antibody (Dall'Acqua et al., J. Immunol. 169:5171-5180 (2002); Dall'Acqua et al., J. Biol. Chem. 281:23514-24 (2006); Robbie et al., Antimicrob. Agents Chemother. 57, 6147-6153 (2013)). See also U.S. Pat. No. 7,083,784, which is hereby incorporated by reference in its entirety.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (KD). Affinity can be measured by common methods known in the art, including those described herein. Low-affinity antibodies generally bind antigen slowly and tend to dissociate readily, whereas high-affinity antibodies generally bind antigen faster and tend to remain bound longer.

The affinity or avidity of an antibody for an antigen can be determined experimentally using any suitable method known in the art, e.g., flow cytometry, enzyme-linked immunosorbent assay (ELISA), or radioimmunoassay (RIA), or kinetics (e.g., KINEXA® or BIACORE™ or OCTET® analysis). Direct binding assays as well as competitive binding assay formats can be readily employed. (See, e.g., Berzofsky et al., "Antibody-Antigen Interactions," In Fundamental Immunology, Paul, W. E., ed., Raven Press: New York, N.Y. (1984); Kuby, Immunology, W. H. Freeman and Company: New York, N.Y. (1992)). The measured affinity of a particular antibody-antigen interaction can vary if measured under different conditions (e.g., salt concentration, pH, temperature). Thus, measurements of affinity and other antigen-binding parameters (e.g., KD or Kd, Kon, Koff) are made with standardized solutions of antibody and antigen, and a standardized buffer, as known in the art.

"Potency" is normally expressed as an $IC_{50}$ (or $EC_{50}$) value, in nM or pM, unless otherwise stated. $IC_{50}$ is the median inhibitory concentration of an antibody molecule. In functional assays, $IC_{50}$ is the concentration that reduces a biological response by 50% of its maximum. In ligand-binding studies, $IC_{50}$ is the concentration that reduces receptor binding by 50% of maximal specific binding level. $IC_{50}$ can be calculated by any number of means known in the art.

The fold improvement in potency for the antibodies or polypeptides of the invention as compared to a reference antibody can be at least about 2-fold, at least about 4-fold, at least about 6-fold, at least about 8-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 110-fold, at least about 120-fold, at least about 130-fold, at least about 140-fold, at least about 150-fold, at least about 160-fold, at least about 170-fold, or at least about 180-fold or more.

The terms "inhibit," "block," and "suppress" are used interchangeably and refer to any statistically significant decrease in a given biological activity, including full blocking of the activity. For example, "inhibition" can refer to a decrease of about 10%, 20%, 30%, 40%, 50%, 60%, 70%, 80%, 90% or 100% in biological activity. Accordingly, when the terms "inhibition" or "suppression" are applied to describe, e.g., an effect of an ADAM17 binding molecule, the terms may refer to the ability of an ADAM17 binding molecule to statistically significantly decrease: (a) binding of ADAM17 to an ADAM 17 substrate (such as an EGFR/erbB/HER ligand), or (b) proteolytic cleavage of an ADAM17 substrate by ADAM17, or (c) activation of, or signaling by, an ADAM17 substrate, or (d) proliferation or survival of a tumor cell whose proliferation or survival is driven, in part, by an ADAM17 substrate, and the like. Inhibition may be determined relative to an untreated control—for example a control not treated with the ADAM17 binding molecule. In some embodiments, an ADAM17 binding molecule can inhibit an activity of ADAM17 (such as those listed above) by at least 10%, or at least 20%, or at least 30%, or at least 40%, or at least 50%, or at least 60%, or at least 70%, or at least 80%, or at least 90% or about 100%, as determined, for example, by flow cytometry, Western blotting, ELISA, proliferation assays, or other assays known to those of skill in the art.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, sports animals, and zoo animals including, e.g., humans, non-human primates, dogs, cats, guinea pigs, rabbits, rats, mice, horses, cattle, bears, and so on.

The term "pharmaceutical composition" refers to a preparation that is in such form as to permit the biological activity of the active ingredient to be effective and which contains no additional components that are unacceptably toxic to a subject to which the composition would be administered. Such composition can be sterile and can comprise a pharmaceutically acceptable carrier, such as physiological saline. Suitable pharmaceutical compositions can comprise one or more of a buffer (e.g. acetate, phosphate or citrate buffer), a surfactant (e.g. polysorbate), a stabilizing agent (e.g. human albumin), a preservative (e.g. benzyl alcohol), an absorption promoter to enhance bioavailability and/or other conventional solubilizing or dispersing agents.

An "effective amount" of a binding molecule as disclosed herein is an amount sufficient to carry out a specifically stated purpose. An "effective amount" can be determined empirically and in a routine manner, in relation to the stated purpose.

The ADAM17 binding molecules of the invention can be naked or conjugated to other molecules such as toxins, labels, etc. The term "label" when used herein refers to a detectable compound or composition that is conjugated directly or indirectly to a binding molecule, so as to generate a "labeled" binding molecule. The label can be detectable by itself (e.g., radioisotope labels or fluorescent labels) or, as in the case of, e.g., an enzymatic label, can catalyze chemical alteration of a substrate compound or composition that is detectable.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already with the disorder. In certain embodiments, a subject is successfully "treated" for a disease or disorder according to the methods provided herein if the patient shows, e.g., total, partial, or transient alleviation or elimination of symptoms associated with the disease or disorder.

"Prevent" or "prevention" refer to prophylactic or preventative measures that prevent and/or slow the development or recurrence of a targeted pathologic condition or disorder. Thus, those in need of prevention include those prone to have or susceptible to the disorder, including those who have had the disorder and are susceptible to recurrence. In certain embodiments, a disease or disorder is successfully prevented according to the methods provided herein if the patient develops, transiently or permanently, e.g., fewer or less severe symptoms or pathology associated with the disease or disorder, or a later onset of symptoms or pathology associated with the disease or disorder, than a patient who has not been subject to the methods of the invention. In some embodiments, recurrence of cancer is prevented for at least about 3, 6, 9, 12, 18, or 24 months after the start of treatment with an ADAM17 binding molecule of the invention.

The terms "polypeptide," "peptide," and "protein" are used interchangeably herein to refer to polymers of amino acids of any length. The polymer can be linear or branched, it can comprise modified amino acids and non-amino acids can interrupt it. The terms also encompass an amino acid polymer that has been modified naturally or by intervention; for example, disulfide bond formation, glycosylation, lipidation, acetylation, phosphorylation or any other manipulation or modification such as conjugation with a labeling component. Also included within the definition are, for example, polypeptides containing one or more analogs of an amino acid (including, for example, unnatural amino acids, etc.), as well as other modifications known in the art. In certain embodiments, the polypeptides can occur as single chains or associated chains.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the amino acid sequences of the binding molecules of the invention do not abrogate the binding of the binding molecule to the antigen(s), i.e., ADAM17, to which the binding molecule binds. Methods of identifying conservative nucleotide and amino acid substitutions which do not eliminate antigen-binding are well-known in the art (see, e.g., Brummell et al., Biochem. 32: 1180-1187 (1993); Kobayashi et al., Protein Eng. 12(10): 879-884 (1999); and Burks et al., Proc. Natl. Acad. Sci. U.S.A. 94:412-417 (1997)).

A "polynucleotide," as used herein can include one or more "nucleic acids," "nucleic acid molecules," or "nucleic acid sequences," and refers to a polymer of nucleotides of any length, and includes DNA and RNA. The polynucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. The preceding description applies to all polynucleotides referred to herein, including RNA and DNA.

The term "vector" means a construct, which is capable of delivering and, in some embodiments, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

An "isolated" polypeptide, antibody, binding molecule, polynucleotide, vector, or cell is in a form not found in nature. Isolated polypeptides, antibodies, binding molecules, polynucleotides, vectors, or cells include those which have been purified to a degree that they are no longer in a form in which they are found in nature. In some embodiments, a polypeptide, antibody, binding molecule, polynucleotide, vector, or cell that is isolated is substantially pure. When used herein, the term "substantially pure" refers to purity of greater than 75%, preferably greater than 80% or 90%, and most preferably greater than 95%.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences.

One such non-limiting example of a sequence alignment algorithm is the algorithm described in Karlin et al., Proc. Natl. Acad. Sci., 87:2264-2268 (1990), as modified in Karlin et al., Proc. Natl. Acad. Sci., 90:5873-5877 (1993), and incorporated into the NBLAST and XBLAST programs (Altschul et al., Nucleic Acids Res., 25:3389-3402 (1991)). In certain embodiments, Gapped BLAST can be used as described in Altschul et al., Nucleic Acids Res. 25:3389-3402 (1997). BLAST-2, WU-BLAST-2 (Altschul et al., Methods in Enzymology, 266:460-480 (1996)), ALIGN, ALIGN-2 (Genentech, South San Francisco, California) or Megalign (DNASTAR) are additional publicly available software programs that can be used to align sequences. In certain embodiments, the percent identity between two nucleotide sequences is determined using the GAP program in the GCG software package (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (J. Mol. Biol. (48):444-453 (1970)), can be used to determine the percent identity between two amino acid sequences (e.g., using either a BLOSUM 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS 4:11-17 (1989)). For example, the percent identity can be determined using the ALIGN program (version 2.0) and using a PAM120 with residue table, a gap length penalty of 12 and a gap penalty of 4. One skilled in the art can determine appropriate parameters for maximal alignment by particular alignment software. In certain embodiments, the default parameters of the alignment software are used.

In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

The term "ALAMARBLUE" as used herein refers to the cell viability reagent that is commercially available from ThermoFischer Scientific (catalog no. DAL 1100) and that is described in "A new Alamar Blue viability assay to rapidly quantify oligodendrocyte death;" Neurosci. Methods. (1999); September 15; Vol. 91(1-2); pages 47-54.

Other terms are defined elsewhere in this patent disclosure, or else are used in accordance with their usual meaning in the art.

II. ADAM17 Binding Molecules

The acronym "ADAM" refers to "a disintegrin and metalloproteinase" enzyme. ADAMs are $Zn^{2+}$-dependent, modular cell surface proteins that belong to the adamalysin protein family. ADAM17 is also referred to using synonyms: CD156b, cSVP, MGC71942, and TACE). The ADAM17 protein, and the nucleotide sequences that encode it are well known in the art. For example, the human ADAM17 mRNA sequence has GenBank/NCBI accession number NM_003183, and both the nucleotide and amino acid sequences of ADAM17s from several different species (including humans and mice) are publicly available, for example in the GenBank/NCBI database. ADAM-17 is a multi-domain protein starting with a signal sequence (1-17 aa), followed by a prodomain (18-214 aa), a metalloenzyme or catalytic domain (215-473 aa), a disintegrin domain (474-572 aa), a cysteine-rich domain (603-671 aa), followed by a transmembrane domain (672-694 aa) and a cytoplasmic tail (695-824 aa). ADAM-17 cleaves the ectodomains of various transmembrane proteins, including ErbB/EGFR ligands, proinflammatory cytokines like TNFα and its receptor, adhesion molecules, and the amyloid precursor protein—all of which are ADAM17 substrates.

The present invention provides ADAM17 binding molecules, e.g., anti-ADAM17 antibodies, and antigen-binding fragments thereof, which specifically bind ADAM17.

The terms "ADAM17 binding molecule" or "binding molecule that binds to ADAM17" or "anti-ADAM17" refer to a binding molecule that is capable of binding ADAM17 with sufficient affinity such that the binding molecule is useful for one of the applications described herein, including, but not limited to, in inhibiting binding of ADAM17 to ADAM17 substrates (such as EGFR/ErbB/Her ligands, inhibiting ADAM17-dependent proteolytic cleavage of ADAM17 substrates (such as EGFR/erbB/Her ligands), inhibiting activation of ADAM17 substrates (such as EGFR/erbB/HER ligands), or inhibiting tumor cell proliferation in vitro or in vivo, for example in therapeutic applications. Typically, a binding molecule that "specifically binds" to ADAM17 binds to an unrelated, non-ADAM17 protein to an extent of less than about 10% of the binding of the binding molecule to ADAM17, as measured, e.g., by a radioimmunoassay (RIA), BIACORE™ (e.g. using recombinant ADAM17 as the analyte and binding molecule as the ligand, or vice versa), KINEXA®, OCTET®, or other binding assays known in the art. In certain embodiments, binding molecule that binds to ADAM17 has a dissociation constant ($K_D$) of ≤1 μM, ≤100 nM, 10 nM, ≤1 nM, ≤0.1 nM, ≤10 pM, ≤1 pM, or ≤0.1 pM.

Exemplary ADAM17 binding molecules of the present invention include the five "lead" antibody clones referred to herein as "D5. Pl. A4," "D5. P2. A11," "D5. P2. B3," "D8. Pl. C1," and "D8. P2. C6," and antigen binding fragments thereof, such as antigen binding fragments that comprise the CDRs of these lead antibody clones. The amino acid sequences of these antibodies, and their CDR regions, are provided in the below tables, which also provides SEQ ID NOs for each amino acid sequence.

TABLE 1

ADAM17 Antibody Heavy & Light Chain Sequences

| Clone | SEQ ID NO. | Amino Acid ASequence |
|---|---|---|
| D5.P1.A4. Heavy chain full sequence | SEQ ID NO. 1 | MDPKGSLSWRILLFLSLAFELSYGQVQLQQSGAEVKKPGASVKVSCKASG YTFTGYYMHWVRQAPGQGLEWMGWINGKSGGTNYAQKFQGRVTMTR DTSISTAYMELSRLKSDDTAVYYCARLDRRDYWGQGTLVTVSSASTKGPS VFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIE KTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYT QKSLSLSPG (SEQ ID NO. 1 (aas 25-139 shown in bold are the variable domain-$V_H$) |
| D5.P1.A4. Light chain full sequence | SEQ ID NO. 2 | MSVPTQVLGLLLLWLTDARCQSVVTQPPSVSGAPGQRVTISCSGSSSNVGR NLVYWYQQLPGAAPRLLIYRNNQRPSGVPDRFSGSKSGTSASLAISGLRS EDEADYYCAAWDDSLSGVVFGGGTKLTVLGQPKAAPSVTLFPPSSEELQA NKATLVCLISDFYPGAVTVAWKADSSPVKAGVETTTPSKQSNNKYAASSYLS LTPEQWKSHRSYSCQVTHEGSTVEKTVAPTECS (SEQ ID NO. 2) (aas 21-136 shown in bold are the variable domain-$V_L$) |
| D5.P2.A11. Heavy chain full sequence | SEQ ID NO. 3 | MDPKGSLSWRILLFLSLAFELSYGQVQLQQSGAEVKKPGASVKVSCKASG YTFTGYYMHWVRQAPGQGLEWMGWINGNSGGTNYAQKFQGRVTMTR DTSISTAYMELSRLKSDNTAVYYCASLDNLDVWGQGTLVTVSSASTKGPS VFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIE KTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYT QKSLSLSPG (SEQ ID NO. 3-aas 25-139 shown in bold are the variable domain-$V_H$) |
| D5 P2.A11. Light chain full sequence | SEQ ID NO. 4 | MSVPTQVLGLLLLWLTDARCQSVVTQPPSVSGAPGQRVTISCSGSSSNVGR NLVYWYQQLPGAAPRLLIYRNNQRPSGVPDRFSGSKSGTSASLAISGLRS EDEADYYCAVWDDKLSAWFGGGTKLTVLGQPKAAPSVTLFPPSSEELQA NKATLVCLISDFYPGAVTVAWKADSSPVKAGVETTTPSKQSNNKYAASSYLS LTPEQWKSHRSYSCQVTHEGSTVEKTVAPTECS (SEQ ID NO. 4) (aas 21-136 shown in bold are the variable domain-$V_L$) |
| D5.P2.B3. Heavy chain full sequence | SEQ ID NO. 5 | MDPKGSLSWRILLFLSLAFELSYGQVQLQQSGAEVKKPGASVKVSCKASG YTFTGYYMHWVRQAPGQGLEWMGWINGNSGGTNYAQKFQGRVTMTR DTSISTAYMELSRLKSDNTAVYYCASSGSMDVWGQGTLVTVSSASTKGPS VFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIE KTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYT QKSLSLSPG (SEQ ID NO. 5-aas shown in bold 25-139 are the variable domain-$V_H$) |
| D5.P2.B3. Light chain full sequence | SEQ ID NO. 6 | MSVPTQVLGLLLLWLTDARCQSVVTQPPSVSGAPGQRVTISCSGSSSNVGR NLVYWYQQLPGAAPRLLIYRNNQRPSGVPDRFSGSKSGTSASLAISGLRS EDEADYYCAAWDDSLSGVVFGGGTKLTVLGQPKAAPSVTLFPPSSEELQA NKATLVCLISDFYPGAVTVAWKADSSPVKAGVETTTPSKQSNNKYAASSYLS LTPEQWKSHRSYSCQVTHEGSTVEKTVAPTECS (SEQ ID NO. 6) (aas 21-136 shown in bold are he variable domain-$V_L$) |

TABLE 1-continued

ADAM17 Antibody Heavy & Light Chain Sequences

| Clone | SEQ ID NO. | Amino Acid ASequence |
|---|---|---|
| D8.P1.C1. Heavy chain full sequence | SEQ ID NO. 7 | MDPKGSLSWRILLFLSLAFELSYGQVQLVQSGAEVKKPGASVKVSCKASG YTFTGYYMHWVRQAPGQGLEWMGWINPNSGGTNYAQKFQGRVTMTR DTSISTAYMELSRLRSDDTAVYYC<u>SSGGSMD</u>VWGQGTLVTVSSASTKGPS VFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIE KTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYT QKSLSLSPG (SEQ ID NO. 7-aas 25-139 shown in bold are the variable domain-V_H) |
| D8.P1.C1. Light chain full sequence | SEQ ID NO. 8 | MSVPTQVLGLLLLWLTDARCQSVLTQPPSASGTPGQRVTISCSGSSSNIGSN YVYWYQQLPGTAPKLLIY<u>RNNQRPS</u>GVPDRFSGSKSGTSASLAISGLRPE DEADYYCAVWDDRLSGVVFGGGTKLTVLGQPKAAPSVTLFPPSSEELQAN KATLVCLI<u>SDFYPGAVT</u>VAWKADSSPVKAGVETTTPSKQSNNKYAASSYLSL TPEQWKSHRSYSCQVTHEGSTVEKTVAPTECS (SEQ ID NO. 8) (aas 21-136 shown in bold are the variable domain-V_L) |
| D8.P2.C6. Heavy chain full sequence | SEQ ID NO. 9 | MDPKGSLSWRILLFLSLAFELSYGQVQLVQSGAEVKKPGASVKVSCKASG YTFTGYYMHWVRQAPGQGLEWMGWINPNSGGTNYAQKFQGRVTMTR DTSISTAYMELSRLRSDDTAVYYCTSGGSFDVWGQGTLVTVSSASTKGPS VFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIE KTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYT QKSLSLSPG (SEQ ID NO. 9-aas 25-139 shown in bold are the variable domain-V_H) |
| D8.P2.C6. Light chain full sequence | SEQ ID NO. 10 | MSVPTQVLGLLLLWLTDARCQSVLTQPPSASGTPGQRVTISCSGSSSNIGSN YVYWYQQLPGTAPKLLIY<u>RNNQRPS</u>GVPDRFSGSKSGTSASLAISGLRSE DEADYYCAAWDDRLSGAVFGGGTKLTVLGQPKAAPSVTLFPPSSEELQAN KATLVCLI<u>SDFYPGAVT</u>VAWKADSSPVKAGVETTTPSKQSNNKYAASSYLSL TPEQWKSHRSYSCQVTHEGSTVEKTVAPTECS (SEQ ID NO. 10) (aas 21-136 shown in bold are the variable domain-V_L) |

In Table 1, the amino acids that comprise the variable ($V_H$ or $V_L$ for heavy and light chains, respectively) domains are represented in bold, and the CDR regions are shown with underlined text. Each of these amino acid sequences is in an IgG format. However, one of skill in the art will recognize, as described elsewhere herein, that these sequences can be engineered to different immunoglobulin formats, and/or to produce antigen binding fragments, and/or otherwise engineered (for example by humanization), while retaining the key determinants for ADAM17—i.e. the CDRs.

TABLE 2

ADAM17 Antibody CDR Sequences

| Clone | CDR H1 | CDRH2 | CDRH3 | CDR L1 | CDR L2 | CDR L3 |
|---|---|---|---|---|---|---|
| D5 Parent | YTFT GY SEQ ID NO. 11 | NGNS GGTN SEQ ID NO. 12 | RLDR RDY SEQ ID NO. 13 | NVGR NL SEQ ID NO. 14 | RNNQ RPS SEQ ID NO. 15 | AWDD SLSG SEQ ID NO. 16 |
| D5.P1. A4 | YTFT GY SEQ ID NO. 17 | NGK<u>S</u> GGTN SEQ ID NO. 18 | RLDR RDY SEQ ID NO. 19 | NVGR NL SEQ ID NO. 20 | RNNQ RPS SEQ ID NO. 21 | AWDD SLSG SEQ ID NO. 22 |
| D5.P2. A11 | YTFT GY SEQ ID NO. 23 | NGNS GGTN SEQ ID NO. 24 | <u>SLDN LDV</u> SEQ ID NO. 25 | NVGR NL SEQ ID NO. 26 | RNNQ RPS SEQ ID NO. 27 | VWDD <u>KLSA</u> SEQ ID NO. 28 |
| D5.P2. B3 | YTFT GY SEQ ID NO. 29 | NGNS GGTN SEQ ID NO. 30 | <u>SSGS MDV</u> SEQ ID NO. 31 | NVGR NL SEQ ID NO. 32 | RNNQ RPS SEQ ID NO. 33 | AWDD SLSG SEQ ID NO. 34 |
| D8 Parent | YTFT GYYM SEQ ID NO. 35 | NPNS GGTN SEQ ID NO. 36 | ASGG GMD SEQ ID NO. 37 | SSNI GSNY SEQ ID NO. 38 | RNNQ RPS SEQ ID NO. 39 | AWDDS LSGVV SEQ ID NO. 40 |
| D8.P1. C1 | YTFT GYYM SEQ ID NO. 41 | NPNS GGTN SEQ ID NO. 42 | SSGG <u>SMD</u> SEQ ID NO. 43 | SSNI GSNY SEQ ID NO. 44 | RNNQ RPS SEQ ID NO. 45 | <u>V</u>WDD<u>R</u> LSGVV SEQ ID NO. 46 |

TABLE 2-continued

ADAM17 Antibody CDR Sequences

| Clone | CDR H1 | CDRH2 | CDRH3 | CDR L1 | CDR L2 | CDR L3 |
|---|---|---|---|---|---|---|
| D8.P2. C6 | YTFT GYYM SEQ ID NO. 47 | NPNS GGTN SEQ ID NO. 48 | TSGG S̲F̲D̲ SEQ ID NO. 49 | SSNI GSNY SEQ ID NO. 50 | RNNQ RPS SEQ ID NO. 51 | AWDDR LSGAV̲ SEQ ID NO. 52 |

The underlined aa residues in Table 2 are mutations introduced during affinity maturation (as compared to, and as can be seen by comparison with, the sequences of the corresponding parental clones.

TABLE 3

ADAM17 Antibody Sequence Summary

| Clone | Sequence summary | SEQ ID NO. |
|---|---|---|
| D5.P1.A4 | Heavy chain full sequence | SEQ ID NO. 1 |
| D5.P1.A4 | Light Chain full sequence | SEQ ID NO. 2 |
| D5.P1.A4 | CDR H1 sequence | SEQ ID NO. 17 |
| D5.P1.A4 | CDR H2 sequence | SEQ ID NO. 18 |
| D5.P1.A4 | CDR H3 sequence | SEQ ID NO. 19 |
| D5.P1.A4 | CDR L1 sequence | SEQ ID NO. 20 |
| D5.P1.A4 | CDR L2 sequence | SEQ ID NO. 21 |
| D5.P1.A4 | CDR L3 sequence | SEQ ID NO. 22 |
| D5.P2.A11 | Heavy chain full sequence | SEQ ID NO. 3 |
| D5.P2.A11 | Light Chain full sequence | SEQ ID NO. 4 |
| D5.P2.A11 | CDR H1 sequence | SEQ ID NO. 23 |
| D5.P2.A11 | CDR H2 sequence | SEQ ID NO. 24 |
| D5.P2.A11 | CDR H3 sequence | SEQ ID NO. 25 |
| D5.P2.A11 | CDR L1 sequence | SEQ ID NO. 26 |
| D5.P2.A11 | CDR L2 sequence | SEQ ID NO. 27 |
| D5.P2.A11 | CDR L3 sequence | SEQ ID NO. 28 |
| D5.P2.B3 | Heavy chain full sequence | SEQ ID NO. 5 |
| D5.P2.B3 | Light Chain full sequence | SEQ ID NO. 6 |
| D5.P2.B3 | CDR H1 sequence | SEQ ID NO. 29 |
| D5.P2.B3 | CDR H2 sequence | SEQ ID NO. 30 |
| D5.P2.B3 | CDR H3 sequence | SEQ ID NO. 31 |
| D5.P2.B3 | CDR L1 sequence | SEQ ID NO. 32 |
| D5.P2.B3 | CDR L2 sequence | SEQ ID NO. 33 |
| D5.P2.B3 | CDR L3 sequence | SEQ ID NO. 34 |
| D8.P1.C1 | Heavy chain full sequence | SEQ ID NO. 7 |
| D8.P1.C1 | Light Chain full sequence | SEQ ID NO. 8 |
| D8.P1.C1 | CDR H1 sequence | SEQ ID NO. 41 |
| D8.P1.C1 | CDR H2 sequence | SEQ ID NO. 42 |
| D8.P1.C1 | CDR H3 sequence | SEQ ID NO. 43 |
| D8.P1.C1 | CDR L1 sequence | SEQ ID NO. 44 |
| D8.P1.C1 | CDR L2 sequence | SEQ ID NO. 45 |
| D8.P1.C1 | CDR L3 sequence | SEQ ID NO. 46 |
| D8.P2.C6 | Heavy chain full sequence | SEQ ID NO. 9 |
| D8.P2.C6 | Light Chain full sequence | SEQ ID NO. 10 |
| D8.P2.C6 | CDR H1 sequence | SEQ ID NO. 47 |
| D8.P2.C6 | CDR H2 sequence | SEQ ID NO. 48 |
| D8.P2.C6 | CDR H3 sequence | SEQ ID NO. 49 |
| D8.P2.C6 | CDR L1 sequence | SEQ ID NO. 50 |
| D8.P2.C6 | CDR L2 sequence | SEQ ID NO. 51 |
| D8.P2.C6 | CDR L3 sequence | SEQ ID NO. 52 |

In addition to providing the specific ADAM17 antibodies, and fragments thereof, whose sequences are provided in Tables 1 and 2 above, the present invention also encompasses variants and equivalents of these ADAM17 antibodies and antibody fragments. For example, such variants include humanized, chimeric, optimized, germlined, and/or other versions of any of the anti-ADAM17 antibodies, or fragments thereof, disclosed herein. Likewise, in some embodiments variants of the specific sequences disclosed herein that comprise one or more substitutions, additions, deletions, or other mutations may be used. A VH and/or VL amino acid sequence or portion thereof, including a CDR sequence, can be, e.g., 85%, 90%, 95%, 96%, 97%, 98% or 99% similar to a sequence set forth herein, and/or comprise 1, 2, 3, 4, 5 or more substitutions, e.g., conservative substitutions, relative to a sequence set forth herein, such as a sequence from any of "D5. Pl. A4," "D5. P2. A11," "D5. P2. B3," "D8. Pl. C1," and/or "D8. P2. C6." In some embodiments an ADAM17 binding molecule according to the present invention comprises a VH and/or VL amino acid sequence, or portion thereof, that is 85%, 90%, 95%, 96%, 97%, 98% or 99% similar to that present in one of the specific sequences provided herein (e.g. one of SEQ ID NO. 1 to SEQ ID NO. 10) sequence set forth herein, and/or comprise 1, 2, 3, 4, 5 or more substitutions, e.g., conservative substitutions, relative to that sequence, but comprises the specific CDR sequences found within such VH and/or VL domains—i.e. any mutations (such as substitutions, additions, deletions, etc.) are outside of the CDRs. Such ADAM17 binding molecules, i.e. having VH and VL regions with a certain percent similarity to a VH region or VL region, or having one or more substitutions, e.g., conservative substitutions, can be obtained by mutagenesis (e.g., site-directed or PCR-mediated mutagenesis) of nucleic acid molecules encoding VH and/or VL regions described herein, followed by testing of the encoded altered binding molecule for binding to ADAM17, and optionally testing for retained function, such as: (a) inhibition of binding of ADAM17 to ADAM17 substrates (such as EGFR/erbB/Her ligands), (b) inhibition of ADAM17-dependent proteolytic cleavage of ADAM17 substrates (such as EGFR/erbB/Her ligands), (c) inhibition of activation (e.g. transactivation) of ADAM17 substrates (such as EGFR/erbB/HER ligands), (d) inhibition of signaling by ADAM17 substrates, and/or (e) inhibition of proliferation of tumor cells in vitro or in vivo, for example using the functional assays described herein.

Subsequent sections of this patent disclosure provide further details regarding different variants of the specific ADAM17 binding molecules described herein that are within the scope of the present invention, and how to make and use such variants.

In some embodiments, the ADAM17 binding molecule is a murine antibody, a human antibody, a humanized antibody, a chimeric antibody, a monoclonal antibody, a polyclonal antibody, a recombinant antibody, a bi-specific antibody, a multispecific antibody, or any combination thereof. In some embodiments, ADAM17 binding molecules comprise a Fab, a Fab', a F(ab')$_2$, a Fd, a Fv, a scFv, a disulfide linked Fv, a V-NAR domain, an IgNar, an intrabody, an IgGΔCH2, a minibody, a F(ab')$_3$ a tetrabody, a triabody, a diabody, a single-domain antibody, DVD-Ig, Fcab, mAb$^2$, a (scFv)$_2$, or a scFv-Fc.

An ADAM17 binding molecule provided herein can include, in addition to a VH and a VL, a heavy chain constant region or fragment thereof. In certain aspects the heavy chain constant region is a human heavy chain constant region, e.g., a human IgG constant region, e.g., a human IgG1 constant region.

In certain embodiments, binding molecules of the invention are produced to comprise an altered Fc region, in which one or more alterations have been made in the Fc region in order to change functional and/or pharmacokinetic properties of the binding molecule. Such alterations may result in altered effector function, reduced immunogenicity, and/or an increased serum half-life. The Fc region interacts with a number of ligands, including Fc receptors, the complement protein C1q, and other molecules, such as proteins A and G. These interactions are essential for a variety of effector functions and downstream signaling events including antibody dependent cell-mediated cytotoxicity (ADCC) and complement dependent cytotoxicity (CDC). Accordingly, in certain embodiments the ADAM17 binding molecules of the invention have reduced or ablated affinity for an Fc ligand responsible for facilitating effector function, compared to an ADAM17 binding molecule not comprising the modification in the Fc region. In particular embodiments, the ADAM17 binding molecule has no ADCC activity and/or no CDC activity. In certain aspects, the ADAM17 binding molecule does not bind to an Fc receptor and/or complement factors. In certain aspects, the ADAM17 binding molecule has no effector function. Selecting particular constant domains to optimize desired effector functions is within the ordinary skill in the art. In some embodiments, the binding molecule is of the IgG1 subtype, and optionally comprises the TM format (L234F/L235E/P331S), as disclosed above in the Definitions section.

In certain aspects, a heavy chain constant region or fragment thereof can include one or more amino acid substitutions relative to a wild-type IgG constant domain, wherein the modified IgG has an increased half-life compared to the half-life of an IgG having the wild-type IgG constant domain. For example, the IgG constant domain can contain one or more amino acid substitutions of amino acid residues at positions 251-257, 285-290, 308-314, 385-389, and 428-436, wherein the amino acid position numbering is according to the EU index as set forth in Kabat. In certain aspects the IgG constant domain can contain one or more of a substitution of the amino acid at Kabat position 252 with Tyrosine (Y), Phenylalanine (F), Tryptophan (W), or Threonine (T), a substitution of the amino acid at Kabat position 254 with Threonine (T), a substitution of the amino acid at Kabat position 256 with Serine (S), Arginine (R), Glutamine (Q), Glutamic acid (E), Aspartic acid (D), or Threonine (T), a substitution of the amino acid at Kabat position 257 with Leucine (L), a substitution of the amino acid at Kabat position 309 with Proline (P), a substitution of the amino acid at Kabat position 311 with Serine (S), a substitution of the amino acid at Kabat position 428 with Threonine (T), Leucine (L), Phenylalanine (F), or Serine (S), a substitution of the amino acid at Kabat position 433 with Arginine (R), Serine (S), Isoleucine (I), Proline (P), or Glutamine (Q), or a substitution of the amino acid at Kabat position 434 with Tryptophan (W), Methionine (M), Serine (S), Histidine (H), Phenylalanine (F), or Tyrosine. More specifically, the IgG constant domain can contain amino acid substitutions relative to a wild-type human IgG constant domain including as substitution of the amino acid at Kabat position 252 with Tyrosine (Y), a substitution of the amino acid at Kabat position 254 with Threonine (T), and a substitution of the amino acid at Kabat position 256 with Glutamic acid (E). In some embodiments, the binding molecule is of the IgG1 subtype, and optionally comprises the triple mutant YTE, as disclosed supra in the Definitions section.

An ADAM17 binding molecule provided herein can include a light chain constant region or fragment thereof. In certain aspects the light chain constant region is a kappa constant region or a lambda constant region, e.g., a human kappa constant region or a human lambda constant region.

In certain aspects, this disclosure provides ADAM17 binding molecules that can specifically bind to the same ADAM17 epitope as a binding molecule comprising the heavy chain variable region (VH) and light chain variable region (VL) of any one of clones "D5. Pl. A4," "D5. P2. A11," "D5. P2. B3," "D8. Pl. C1," and "D8. P2. C6." The term "epitope" refers to a target protein determinant capable of binding to a binding molecule of the invention. Epitopes usually consist of chemically active surface groupings of molecules such as amino acids or sugar side chains, and usually have specific three-dimensional structural characteristics, as well as specific charge characteristics. Conformational and non-conformational epitopes are distinguished in that the binding to the former but not the latter is lost in the presence of denaturing solvents. Such binding molecules can be identified based on their ability to cross-compete (e.g., to competitively inhibit the binding of, in a statistically significant manner) with binding molecules, such as "D5. Pl. A4," "D5. P2. A11," "D5. P2. B3," "D8. Pl. C1," and "D8. P2. C6," in standard ADAM17 binding or activity assays.

Accordingly, in one embodiment, the invention provides ADAM17 binding molecules that compete for binding to ADAM17 with another ADAM17 binding molecule of the invention, such as one of clones "D5. Pl. A4," "D5. P2. A11," "D5. P2. B3," "D8. Pl. C1," and "D8. P2. C6." The ability of a binding molecule to inhibit the binding of, e.g., "D5. Pl. A4," "D5. P2. A11," "D5. P2. B3," "D8. Pl. C1," or "D8. P2. C6," demonstrates that the test binding molecule can compete with "D5. Pl. A4," "D5. P2. A11," "D5. P2. B3," "D8. Pl. C1," or "D8. P2. C6" for binding to ADAM17, such a binding molecule can, according to non-limiting theory, bind to the same or a related (e.g., a structurally similar or spatially proximal) epitope on ADAM17 as the ADAM17 binding molecule with which it competes. In one embodiment, an anti-ADAM17 antibody or antigen-binding fragment thereof binds to the same epitope on ADAM17 as any of clones "D5. Pl. A4," "D5. P2. A11," "D5. P2. B3," "D8. Pl. C1," or "D8. P2. C6." The term "competes" indicates that a binding molecule competes unidirectionally for binding to ADAM17 with any one of clones "D5. Pl. A4," "D5. P2. A11," "D5. P2. B3," "D8. Pl. C1," or "D8. P2. C6." The term "cross-competes" indicates that a binding molecule competes bidirectionally for binding to ADAM17 with any one of clones "D5. Pl. A4," "D5. P2. A11," "D5. P2. B3," "D8. Pl. C1," or "D8. P2. C6."

ADAM17 binding molecules provided herein can have beneficial properties. For example, the binding molecule can inhibit, suppress, or block various ADAM17-mediated activities, e.g., proteolytic cleavage of cell surface EGFR/erb2/Her2 molecules, and the associated transactivation thereof, which can be measured by assays known in the art.

In certain aspects, the binding molecules provided herein can bind to ADAM17 with a binding affinity characterized by a dissociation constant ($K_D$) of about 100 pM to about 0.5 nM as measured by a Biacore™ assay or on a Kinetic Exclusion Assay (KinExA) 3000 platform or on an Octet® instrument.

In certain aspects, an anti-ADAM17 antibody or antigen-binding fragment thereof can specifically bind to ADAM17 e.g., human ADAM17, or an antigenic fragment thereof, with a dissociation constant or $K_D$ of less than $10^{-6}$ M, or of less than $10^{-7}$ M, or of less than $10^{-8}$ M, or of less than $10^{-9}$ M, or of less than $10^{-10}$ M, or of less than $10^{-11}$ M, of less than $10^{-12}$ M, of less than $10^{-13}$ M, of less than $10^{-14}$ M, or of less than $10^{-15}$ M as measured, e.g., by Biacore™ or KinExA® or Octet®.

In another embodiment, an ADAM17 binding molecule of the invention binds to ADAM17, or an antigenic fragment thereof, with a $K_{off}$ of less than $1\times10^3$ s$^{-1}$, or less than $2\times10^{-3}$ s$^{-1}$. In other embodiments, an ADAM17 binding molecule binds to ADAM17, or an antigenic fragment thereof, with a $K_{off}$ of less than $10^{-3}$ s$^{-1}$, less than $5\times10^{-3}$ s$^{-1}$, less than $10^{-4}$ s$^{-1}$, less than $5\times10^{-4}$ s$^{-1}$, less than $10^{-5}$ s$^{-1}$, less than $5\times10^{-5}$ s$^{-1}$, less than $10^{-6}$ s$^{-1}$, less than $5\times10^{-6}$ s$^{-1}$, less than less than $5\times10^{-7}$ s$^{-1}$, less than $10^{-8}$ s$^{-1}$, less than $5\times10^{-8}$ s$^{-1}$, less than $10^{-9}$ s$^{-1}$, less than $5\times10^{-9}$ s$^{-1}$, or less than $10^{-10}$ s$^{-1}$ as measured, e.g., by Biacore™ or KinExA® or Octet®.

In another embodiment, an ADAM17 binding molecule of the invention binds to ADAM17, or an antigenic fragment thereof, with an association rate constant or $K_{on}$ rate of at least $10^5$ M$^{-1}$ s$^{-1}$, at least $5\times10^5$ M$^{-1}$ s$^{-1}$ at least $10^6$ M$^{-1}$ s$^{-1}$ at least $5\times10^6$ M$^{-1}$ s$^{-1}$, at least $10^7$ M$^{-1}$ s$^{-1}$ at least $5\times10^7$ M$^{-1}$ s$^{-1}$, or at least $10^8$ M$^{-1}$ s$^{-1}$, or at least $10^9$ M$^{-1}$ s$^{-1}$ as measured, e.g., by Biacore™ or KinExA® or Octet®.

The disclosure further provides an ADAM17 binding molecule that is conjugated to a heterologous agent. In certain aspects, the agent can be an antimicrobial agent, a therapeutic agent, a prodrug, a peptide, a protein, an enzyme, a lipid, a biological response modifier, a pharmaceutical agent, a lymphokine, a heterologous antibody or fragment thereof, a detectable label, a polyethylene glycol (PEG), or a combination of two or more of any said agents.

In certain aspects, the disclosure provides a composition, e.g., a pharmaceutical composition, comprising an ADAM17 binding molecule of the invention, optionally further comprising one or more carriers, diluents, excipients, or other additives.

III. Preparation of ADAM17 Binding Molecules

Monoclonal anti-ADAM17 antibodies can be prepared using hybridoma methods, such as those described by Kohler and Milstein Nature 256:495 (1975). Using the hybridoma method, a mouse, hamster, or other appropriate host animal, is immunized to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol (PEG), to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. RIA or ELISA) can then be propagated either in in vitro culture using standard methods (Goding, *Monoclonal Antibodies: Principles and Practice*, Academic Press, 1986) or in vivo as ascites tumors in an animal. The monoclonal antibodies can then be purified from the culture medium or ascites fluid.

ADAM17 binding molecules can also be made using recombinant DNA methods, for example, as described in U.S. Pat. No. 4,816,567. In some instances, the polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains or antigen-binding fragments thereof are then cloned into suitable expression vectors, which when transfected into host cells such as *E. coli* cells, simian COS cells, Chinese hamster ovary (CHO) cells, or myeloma cells that do not otherwise produce immunoglobulin protein, binding molecules are generated by the host cells. Also, recombinant ADAM17 binding molecules can be isolated from phage display libraries expressing CDRs of the desired species, as described by McCafferty et al. (*Nature,* 348:552-554 (1990)); Clackson et al. (*Nature,* 352:624-628 (1991)); and Marks et al. (*J. Mol. Biol.,* 222:581-597 (1991)). Production and expression of nucleic acids comprising nucleotide sequences encoding ADAM17 binding molecules are discussed in more detail in the next section.

The polynucleotide(s) encoding a binding molecule can further be modified in a number of different manners using recombinant DNA technology to generate alternative binding molecules. In some embodiments, the constant domains of the light and heavy chains of, for example, a mouse monoclonal antibody can be substituted (1) for those regions of, for example, a human antibody to generate a chimeric antibody or (2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In certain embodiments, the ADAM17 binding molecule is a human antibody or antigen-binding fragment thereof. Human antibodies can be directly prepared using various techniques known in the art. Immortalized human B lymphocytes immunized in vitro or isolated from an immunized individual that produce an antibody directed against a target antigen can be generated (See, e.g., Cole et al., *Monoclonal Antibodies and Cancer Therapy*, Alan R. Liss, p. 77 (1985); Boemer et al., *J. Immunol.* 147 (1):86-95 (1991); and U.S. Pat. No. 5,750,373).

The ADAM17 binding molecule can be selected from a phage library, where the phage library expresses human antibodies, as described, for example, by Vaughan et al. (Nat. Biotechnol., 14:309-314 (1996)), Sheets et al. (*Proc. Nat'l. Acad. Sci. U.S.A.* 95:6157-6162 (1998)), Hoogenboom et al. (*J. Mol. Biol.* 227:381 (1991)), and Marks et al. (*J. Mol. Biol.* 222:581 (1991)). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and in Rothe et al., *J. Mol. Biol.* 375:1182-1200 (2007).

Affinity maturation strategies and chain shuffling strategies are known in the art and can be employed to generate high affinity human antibodies or antigen-binding fragments thereof. (See Marks et al., *Bio/Technology* 10:779-783 (1992)).

In some embodiments, an ADAM 17 binding molecule can be a humanized antibody or antigen-binding fragment thereof. Methods for engineering, humanizing, or resurfacing non-human or human antibodies can also be used and are well known in the art. A humanized, resurfaced, or similarly engineered antibody can have one or more amino acid residues from a source that is non-human, e.g., mouse, rat, rabbit, non-human primate, or other mammal. These non-human amino acid residues are replaced by residues that are often referred to as "import" residues, which are typically taken from an "import" variable, constant, or other domain of a known human sequence. Such imported sequences can be used to reduce immunogenicity or reduce, enhance, or modify binding, affinity, on-rate, off-rate, avidity, specificity, half-life, or any other suitable characteristic, as known in the art. In general, the CDR residues are directly and most substantially involved in influencing ADAM17 binding. Accordingly, part or all of the non-human or human CDR sequences are maintained while the non-human sequences of the variable and constant regions can be replaced with human or other amino acids. Humanization, resurfacing, or engineering of ADAM17 antibodies or antigen-binding fragments thereof can be performed using any known method, such as, but not limited to, those described in, Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,639,641; 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567; 7,557,189; 7,538,195; and 7,342,110; International Application Nos. PCT/US98/16280; PCT/US96/18978; PCT/US91/09630; PCT/US91/05939; PCT/US94/01234; PCT/GB89/01334; PCT/GB91/01134; PCT/GB92/01755; International Patent Application Publication Nos. WO90/14443; WO90/14424; WO90/14430; and European Patent Publication No. EP 229246.

Anti-ADAM17 humanized antibodies and antigen-binding fragments thereof can also be made in transgenic mice containing human immunoglobulin loci that are capable, upon immunization, of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain embodiments the ADAM17 binding molecule is anti-ADAM17 antibody fragment. Various techniques are known for the production of antibody fragments. Traditionally, these fragments are derived via proteolytic digestion of intact antibodies. See, e.g., Morimoto et al., J. Biochem. Biophys. Meth. 24:107-117 (1993); Brennan et al., Science, 229:81-83 (1985). In certain embodiments, anti-ADAM17 antibody fragments are produced recombinantly. Fab, Fv, and scFv antibody fragments can all be expressed in and secreted from E. coli or other host cells, thus allowing the production of large amounts of these fragments. Such anti-ADAM17 antibody fragments can also be isolated from the antibody phage libraries discussed above. Anti-ADAM17 antibody fragments can also be linear antibodies, as described in U.S. Pat. No. 5,641,870. Other techniques for the production of antibody fragments will be apparent to the skilled practitioner.

According to the present invention, techniques can be adapted for the production of single-chain antibodies specific to ADAM17 (see, e.g., U.S. Pat. No. 4,946,778). In addition, methods can be adapted for the construction of Fab expression libraries (see, e.g., Huse et al., Science 246:1275-1281 (1989)) to allow rapid and effective identification of monoclonal Fab fragments with the desired specificity for ADAM17. Antibody fragments can also be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

In some aspects, the ADAM17 binding molecules can be modified in order to reduce or eliminate effector function. This can be achieved, for example, by the triple mutation (TM) L234F/L235E/P331S in the Fc domain of IgG1. Other mutations that reduce effector function are known in the art. See, e.g., Armour et al., Eur. J. Immunol. 29:2613-2624, 1999; Shields et al., J. Biol. Chem. 276:6591-6604, 2001.

In certain aspects, an ADAM17 binding molecule can be modified to increase its serum half-life. This can be achieved, for example, by incorporation of a salvage receptor binding epitope into the binding molecule by mutation of the appropriate region, or by incorporating the epitope into a peptide tag that is then fused to the binding molecule at either end or in the middle (e.g., by DNA or peptide synthesis), or by YTE mutation. Other methods to increase the serum half-life of an antibody or antigen-binding fragment thereof, e.g., conjugation to a heterologous molecule such as PEG, are known in the art.

Heteroconjugate ADAM17 antibodies and antigen-binding fragments thereof are also within the scope of the present invention. Heteroconjugate antibodies are composed of two covalently joined antibodies. Such antibodies have, for example, been proposed to target immune cells to unwanted cells (see, e.g., U.S. Pat. No. 4,676,980). It is contemplated that heteroconjugate anti-ADAM17 antibodies and antigen-binding fragments thereof can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

An ADAM17 binding molecule can be modified to contain additional chemical moieties not normally part of the protein. Such moieties can improve the characteristics of the binding molecule, for example, solubility, biological half-life, or absorption. The moieties can also reduce or eliminate any undesirable side effects of the binding molecule. An overview of those moieties can be found in Remington's Pharmaceutical Sciences, 20th ed., Mack Publishing Co., Easton, PA (2000).

IV. Polynucleotides Encoding ADAM17 Binding Molecules, Preparation and Expression Thereof This disclosure provides certain polynucleotides comprising nucleic acid sequences that encode ADAM17 binding molecules. The polynucleotides of the invention can be in the form of RNA or in the form of DNA. DNA includes cDNA, genomic DNA, and synthetic DNA; and can be double-stranded or single-stranded, and, if single stranded, can be the coding strand or non-coding (anti-sense) strand.

In certain embodiments, the polynucleotide can be isolated. In certain embodiments, the polynucleotide can be substantially pure. In certain embodiments, the polynucleotide can be cDNA or are derived from cDNA. In certain embodiments, the polynucleotide can be recombinantly produced. In certain embodiments, the polynucleotide can comprise the coding sequence for a mature polypeptide, fused in the same reading frame to a polynucleotide which aids, for example, in expression and optionally, secretion, of a polypeptide from a host cell (e.g., a promoter or other regulatory sequence, a leader sequence that functions as a secretory sequence for controlling transport of a polypeptide from the cell). The polypeptide having a leader sequence is a pre-protein and can have the leader sequence cleaved by the host cell to form the mature form of the polypeptide. The polynucleotide can also encode an ADAM17 binding pro-protein which is the mature protein plus additional 5' amino acid residues.

The disclosure provides an isolated polynucleotide comprising a nucleic acid encoding an ADAM17 binding molecule comprising an amino acid sequence from a VH and/or VL domain having 85%, 90%, 95%, 96%, 97%, 98% or 99% similarity to an amino acid sequence set forth herein, and/or comprising 1, 2, 3, 4, 5 or more amino acid substitutions, e.g., conservative substitutions, relative to an amino acid sequence set forth herein, such as a sequence from any of ADAM17 clones "D5. Pl. A4," "D5. P2. A11," "D5. P2. B3," "D8. Pl. C1," and "D8. P2. C6."

In certain embodiments the polynucleotide that comprises the coding sequence for the ADAM17 binding molecule is fused in the same reading frame as a marker sequence that allows, for example, for purification of the encoded polypeptide. For example, the marker sequence can be a hexahistidine tag (SEQ ID NO: 53) supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used.

Polynucleotide variants are also provided. Polynucleotide variants can contain alterations in the coding regions, non-coding regions, or both. In some embodiments, polynucleotide variants contain alterations that produce silent substitutions, additions, or deletions, but do not alter the properties or activities of the encoded polypeptide. In some embodiments, polynucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*).

The invention includes vectors comprising the polynucleotides described above. Suitable vectors are described elsewhere herein, and are known to those of ordinary skill in the art. In some embodiments, a polynucleotide comprising a nucleic acid encoding a VH domain or portion thereof and the polynucleotide comprising a nucleic acid encoding a VL domain or portion thereof can reside in a single vector, or can be on separate vectors. Accordingly, the disclosure provides one or more vectors comprising the polynucleotides described above.

In certain aspects, the disclosure provides a composition, e.g., a pharmaceutical composition, comprising a polynucleotide or vector as described above, optionally further comprising one or more carriers, diluents, excipients, or other additives.

The disclosure further provides a host cell comprising a polynucleotide or vector of the invention, wherein the host cell can, in some instances, express a binding molecule that specifically binds to ADAM17. Such a host cell can be utilized in a method of making an ADAM17 binding molecule, where the method includes (a) culturing the host cell and (b) isolating the binding molecule from the host cell or from the culture medium, if the binding molecule is secreted by the host cell.

In some embodiments a nucleotide sequence encoding an ADAM17 binding molecule can be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a nucleotide oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed, e.g., by nucleotide sequencing, restriction mapping, and/or expression of a biologically active polypeptide in a suitable host. In order to obtain high expression levels of a transfected gene in a host, the gene can be operatively linked to or associated with transcriptional and translational expression control sequences that are functional in the chosen expression host.

In certain embodiments, recombinant expression vectors are used to amplify and express DNA encoding ADAM17 binding molecules. Recombinant expression vectors are replicable DNA constructs that have synthetic or cDNA-derived DNA fragments encoding a polypeptide chain of an ADAM17 binding molecule, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where a recombinant protein is expressed without a leader or transport sequence, the protein can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR 1, pBR322, pMB9 and their derivatives, wider host range plasmids, such as M13, and filamentous single-stranded DNA phages.

Suitable host cells for expression of an ADAM17 binding molecule include prokaryotes, yeast, insect, or higher eukaryotic cells under the control of appropriate promoters. Prokaryotes include gram negative or gram-positive organisms, for example *E. coli* or bacilli. Higher eukaryotic cells include established cell lines of mammalian origin as described below. Cell-free translation systems could also be employed. Additional information regarding methods of protein production, including antibody production, can be found in, e.g., U.S. Patent Publication No. 2008/0187954, U.S. Pat. Nos. 6,413,746 and 6,660,501, and International Patent Publication No. WO 04009823.

Various mammalian or insect cell culture systems can be advantageously employed to express recombinant ADAM17 binding molecules. Expression of recombinant proteins in mammalian cells can be performed because such proteins are generally correctly folded, appropriately modified, and completely functional. Examples of suitable mammalian host cell lines include 293 cells (e.g., HEK-293, HEK-293T, AD293), the COS-7 lines of monkey kidney cells described by Gluzman (Cell 23:175, (1981)), and other cell lines including, for example, L cells, C127, 3T3, Chinese hamster ovary (CHO), HeLa, and BHK cell lines. Mammalian expression vectors can comprise non-transcribed elements, such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. Baculovirus systems for production of heterologous proteins in insect cells are reviewed by Luckow and Summers (*BioTechnology* 6:47 (1988)).

ADAM17 binding molecules produced by a transformed host can be purified according to any suitable method. Such standard methods include chromatography (e.g., ion exchange, affinity, and sizing column chromatography), centrifugation, differential solubility, or by any other standard technique for protein purification. Affinity tags such as hexahistidine (SEQ ID NO: 53), maltose binding domain, influenza coat sequence, and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems that secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose, or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify an ADAM17 binding molecule. Some or all of the foregoing purification steps, in various combinations, can also be employed to provide a homogeneous recombinant protein.

A recombinant ADAM17 binding molecule produced in bacterial culture can be isolated, for example, by initial extraction from cell pellets, followed by one or more concentration, salting-out, aqueous ion exchange, or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005.

V. Use of ADAM17 Binding Molecules

The present invention provides various methods of using the ADAM17 binding molecules described herein. Such methods include, but are not limited to, use of the ADAM17 binding molecules described herein for: (a) inhibition of binding of ADAM17 to ADAM17 substrates (such as EGFR/erbB/Her ligands), (b) inhibition of ADAM17-dependent proteolytic cleavage of ADAM17 substrates (such as EGFR/erbB/Her ligands), (c) inhibition of activation (e.g. transactivation) of ADAM17 substrates (such as EGFR/erbB/HER ligands), (d) inhibition of signaling by ADAM17 substrates, and (e) inhibition of proliferation of tumor cells in vitro or in vivo, such as tumor cells whose proliferation is driven, at least in part, by ADAM17-dependent proteolytic cleavage of ADAM17 substrates (such as EGFR/erbB/HER ligands). Such tumor cells include, but are not limited to, breast, colon, glioma and lung cancer cells.

In some embodiments, the ADAM17 binding molecules provided herein are useful for the treatment of, and/or prevention of recurrence of, cancer. Examples of cancers that may be treated, or the recurrence of which may be prevented, using the ADAM17 binding molecules of the invention include breast, colon, glioma and lung cancers. For example, in one embodiment, the present invention provides a method of treatment, the method comprising administering to a subject in need thereof an ADAM17 binding molecule, or a composition comprising an ADAM17 binding molecule, such as, for example, a pharmaceutical composition. In some such embodiments, the subject has breast cancer, colon cancer, a glioma, or lung cancer.

Similarly, the ADAM17 binding molecules of the invention are also useful for inhibiting the proliferation of, or killing tumor cells. For example, in one embodiment, the present invention provides a method of inhibiting the proliferation of tumor cells, the method comprising contacting tumor cells with an ADAM17 binding molecule, or a composition comprising an ADAM17 binding molecule, such as, for example, a pharmaceutical composition. In some such embodiments the tumor cells are breast, colon, glioma, or lung tumor cells. In some embodiments the cells are in vitro. In some embodiments the cells are in vivo.

In other embodiments, the present in the present invention provides methods of inhibiting (a) ADAM17-dependent proteolytic cleavage of an ADAM17 substrate, and/or (b) binding of ADAM17 to an ADAM17 substrate, and/or (c) activation (e.g. transactivation) of and ADAM17 substrate, and/or (d) signaling by an ADAM17 substrate whose signaling activity is modulated by ADAM17-dependent proteolytic activity, such methods comprising contacting cells with an ADAM17 binding molecule, or a composition comprising an ADAM17 binding molecule. In some such embodiments the cells are tumor cells, such as, for example, breast, colon, glioma, or lung tumor cells. In some embodiments the cells are in vitro. In some embodiments the cells are in vivo.

In the case of in vivo therapeutic applications, clinical response to administration of an ADAM17 binding molecule can be assessed using standard screening techniques known in the art, such as magnetic resonance imaging (MRI), x-radiographic imaging, computed tomographic (CT) scan, flow cytometry or fluorescence-activated cell sorter (FACS) analysis, histology, gross pathology, and blood chemistry, including but not limited to changes detectable by ELISA, ELISPOT, RIA, chromatography, and the like. Further, the subject undergoing therapy with the ADAM17 binding molecule can experience improvement in the symptoms associated with the disease being treated.

Methods of preparing ADAM17 binding molecules for administration to a subject, and methods of administering an ADAM17 binding molecule to a subject, are well-known to those of ordinary skill in the art, or can be readily determined by those of ordinary skill in the art. For example, the route of administration of the ADAM17 binding molecule can be, for example, oral, parenteral, by inhalation, or topical. The term "parenteral" as used herein includes, e.g., intravenous, intraarterial, intraperitoneal, intramuscular, subcutaneous, rectal, and vaginal administration. Oral dosage forms include, e.g., capsules, tablets, aqueous suspensions, and solutions. Nasal aerosol or inhalation dosage forms can be prepared, for example, as solutions in saline, employing benzyl alcohol or other suitable preservatives, absorption promoters to enhance bioavailability, and/or other conventional solubilizing or dispersing agents.

Usually, a suitable pharmaceutical composition can comprise a buffer (e.g. acetate, phosphate or citrate buffer), optionally a surfactant (e.g. polysorbate), optionally a stabilizer agent (e.g. human albumin), etc. The form and character of the pharmaceutically acceptable carrier or diluent can be dictated by the amount of active ingredient with which it is to be combined, the route of administration and other well-known variables. A cocktail comprising one or more species of ADAM17 binding molecules, e.g., anti-ADAM17 antibodies, or antigen-binding fragments or variants thereof, can also be used. In other methods, ADAM17 binding molecules can be delivered directly to the site where its action is required, thereby increasing the exposure of the target cells (e.g. tumor cells) to the therapeutic agent. In one embodiment, the administration is directly into a tumor.

As discussed herein, ADAM17 binding molecules can be administered in a therapeutically effective amount for the in vivo treatment of certain cancers, such as breast cancer, colon cancer, lung cancer, and gliomas. In this regard, it will be appreciated that the disclosed binding molecules can be formulated to facilitate administration and promote stability of the ADAM17 binding molecules. Pharmaceutical compositions in accordance with the present invention can comprise a pharmaceutically acceptable, non-toxic, sterile carrier such as physiological saline, non-toxic buffers, preservatives and the like. For the purposes of the instant application, a "therapeutically effective amount" of an ADAM17 binding molecule means an amount sufficient to achieve a benefit, e.g., to ameliorate symptoms of a disease or condition (e.g. a cancer) or to inhibit proliferation of a cancer cell. Suitable formulations for use in the therapeutic methods disclosed herein are described in Remington's Pharmaceutical Sciences, 20th ed., Mack Publishing Co., Easton, PA (2000).

The composition can be administered as a single dose, multiple doses, or over an established period of time in an infusion. Dosage regimens also can be adjusted to provide the optimum desired response (e.g., a therapeutic or prophylactic response). The amount of an ADAM17 binding molecule that can be combined with carrier materials to produce a dosage form will vary depending upon many different factors, including means of administration, target site, physiological state of the patient (i.e., the severity of the disease, the history of the disease, and the age, height, weight, health, and physical condition of the individual undergoing therapy), whether treatment is prophylactic or therapeutic, other medications administered, and whether the subject is a human or an animal. Usually, the subject is a human, but non-human mammals, including transgenic mammals, can also be treated. The amount of an ADAM17 binding molecule to be administered is readily determined by one of ordinary skill in the art without undue experimentation, given this disclosure. Treatment dosages can be titrated using routine methods known to those of skill in the art to optimize safety and efficacy.

The ADAM17 binding molecules of the invention can be administered in combination with one or more additional active agents. For example, in the treatment or prevention of recurrence of cancer, the ADAM17 binding molecule can be administered in conjunction with a standard-of-care (SOC) agent. In some instances, the ADAM17 binding molecule is administered in combination with one or more chemotherapeutic agents or other therapeutic agents, including immunotherapeutic agents. Examples of other agents that can be co-administered with an ADAM17 binding molecule include, but are not limited to, afatinib, actinomycin, azacitidine, azathioprine, bevacizumab, bleomycin, bortezomib, carboplatin, capecitabine, cetuximab, cisplatin, chlorambucil, cyclophosphamide, cytarabine, daunorubicin, docetaxel, doxifluridine, doxorubicin, epirubicin, epothilone, erlotinib, etoposide, fluorouracil, gefitinib, gemcitabine, hydroxyurea, idarubicin, imatinib, irinotecan, mechlorethamine, mercaptopurine, methotrexate, mitoxantrone, olaparib, oxaliplatin, paclitaxel, panitumab, pazopanib, pemetrexed, poly(ADP-ribose) polymerase (PARP) inhibitors, tamoxifen, teniposide, tioguanine, topotecan, trastuzumab, tretinoin, valrubicin, vinblastine, vincristine, vindesine, vinorelbine, and vintafolide.

In embodiments in which more than one active agent is administered, the agents can be administered together (for example, in the same formulation and/or at the same time), or separately (for example, in different formulations and/or at different times). In some such embodiments, the agents are administered systemically. In some such embodiments, the agents are administered locally. In some such embodiments, one (or more) agent is administered systemically and one (or more) agent is administered locally. Where two such agents are used, it may be possible to use lower dosages or amounts of each agent, as compared to the dosages necessary when each agent is used alone.

This disclosure also provides for the use of an ADAM17 binding molecule as described herein to treat or prevent recurrence of cancer, such as breast cancer, colon cancer, lung cancer, or a glioma.

This disclosure also provides for the use of an ADAM17 binding molecule as described herein in the manufacture of a medicament for treating, or preventing recurrence of, a cancer, such as breast cancer, colon cancer, lung cancer, or a glioma.

VI. Assays and Diagnostics

The ADAM17 binding molecules of the invention can be also be used for a variety of different applications, including those that involve detecting ADAM17. Such methods typically involve assaying the expression level ADAM17, for example by qualitatively or quantitatively measuring or estimating the level of ADAM17 in a first biological sample either directly (e.g., by determining or estimating absolute protein level) or relatively (e.g., by comparison to a second biological sample). For example, the ADAM17 expression level in a first biological sample can be measured or estimated and compared to a that of a standard or control taken from a second biological sample. A "biological sample" is a sample obtained from an individual, cell line, tissue culture, or other source of cells potentially expressing ADAM17. Methods for obtaining tissue biopsies and body fluids from mammals are known in the art. The ADAM17 binding molecules of the invention can be used to assay ADAM17 protein levels in a biological sample using classical immunohistological methods known to those of skill in the art (e.g., see Jalkanen, et al., J. Cell. Biol. 101:976-985 (1985); Jalkanen et al., J. Cell Biol. 105:3087-3096 (1987)). Immunoassays that can be used include but are not limited to competitive and non-competitive assay systems using techniques such as Western blots, radioimmunoassays, ELISA (enzyme linked immunosorbent assay), ELISPOT, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and immunoelectron microscopy, to name some examples. Such assays are routine and well known in the art. Those skilled in the art will be able to determine operative and optimal assay conditions for each determination by employing routine experimentation.

Detection of ADAM17 can be facilitated by coupling the binding molecule to a detectable substance or label. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin. An example of a luminescent material is luminol. Examples of bioluminescent materials include luciferase, luciferin, and aequorin. Examples of suitable radioactive material include 125I, 131I, 35S, or 3H.

In situ detection can be accomplished by removing a histological specimen, for example a tumor sample, from a subject, and contacting the specimen with a labeled ADAM17 binding molecule, or with an ADAM17 antibody and a labeled secondary antibody. Through the use of such a procedure, it is possible to determine not only the presence of ADAM17, but also its distribution in the examined tissue. Using the present invention, those of ordinary skill will readily perceive that any of a wide variety of histological methods (such as staining procedures) can be modified in order to achieve such in situ detection.

VII. Kits Comprising ADAM17 Binding Molecules

This disclosure further provides kits that comprise an ADAM17 binding molecule, which can be used to perform the methods described herein. In certain embodiments, a kit comprises at least one purified ADAM17 binding molecule in one or more containers. In some embodiments, the kit contains one or more of the components necessary and/or sufficient to perform a detection assay, including controls, directions for performing assays, and any necessary software for analysis and presentation of results. One skilled in the art will readily recognize that the disclosed ADAM17 binding molecules can be readily incorporated into any of the established kit formats that are well known in the art.

Embodiments of the present disclosure can be further described and understood by reference to the following non-limiting "Examples," which describe in the preparation of certain exemplary ADAM17 binding molecules, some exemplary characterization of such molecules, and some exemplary methods for using such binding molecules. It will be apparent to those skilled in the art that many modifications to the specific description provided in the Examples can be practiced without undue experimentation and without departing from the scope of the present disclosure.

EXAMPLES

Example 1

Development and In Vitro Testing of ADAM17 Binding Molecules

ADAM17 is activated in many cancers and, in turn, activates oncogenic pathways, including those involving signaling by ErbB family members (including Her1 (also known as EGFR or ErbB1), Her2 (also referred to as Neu or ErbB2), Her3 (also referred to as ErbB3), and Her4), as well as those underlying resistance to targeted anti-EGFR therapies. While ADAM17 is a well-validated target, inhibitors against its active/catalytic site have failed clinical trials due to lack of specificity/efficacy and toxicity issues. The present invention provides a novel intervention strategy based on targeting the substrate-recognition domain of ADAM17—which is essential for ADAM17 activity. By targeting this domain of ADAM17 instead of the catalytic site, the adverse side effects associated with prior attempts to target ADAM17 for therapeutic applications may be avoided.

As an initial step, a large human phage-display Fab library (see reference 22) was screened to identify antibodies that bind to the ADAM17 substrate-recognition domain. (Throughout this patent disclosure, the terms "ADAM17 substrate recognition domain" and "ADAM17 substrate binding domain" may be used interchangeably).

Two highly specific anti-ADAM17 Fabs were identified—termed D5 and D8. The Fabs were selected by ELISA-based screening and their specificities for the ADAM17 substrate-binding domain were confirmed. Cross-reactivity with the substrate-binding domains of closely related ADAM's, such as ADAM10 and ADAM19, were evaluated and it was found that these two Fabs specifically recognized the ADAM17 substrate-binding domain.

Figure 1:
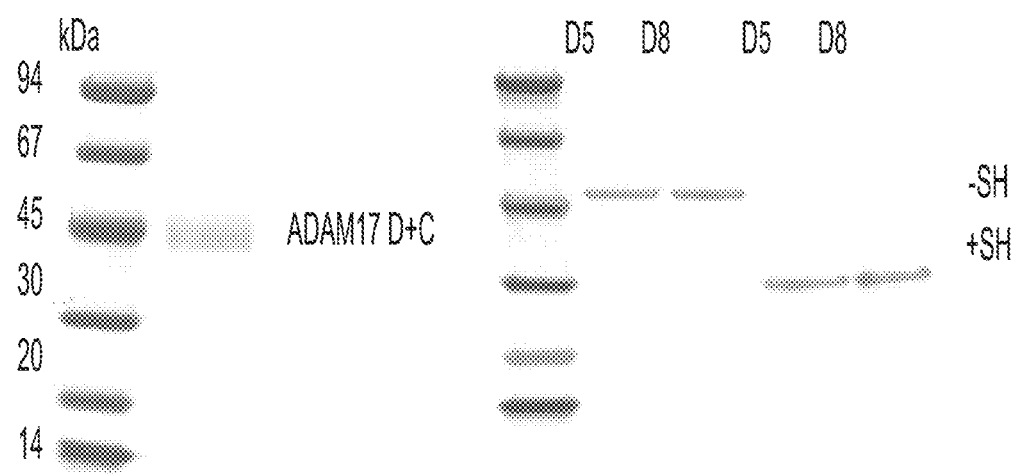
FIG. 1. Images of SDS-PAGE gels. The left panel shows a gel on which the expressed and purified ADAM17 D+C protein was run. The right panel shows a gel on which the D5 and D8 Fabs were run both in the absence and presence of beta-mercaptoethanol.

The D5 and D8 anti-ADAM17 Fabs were expressed and purified, as follows. *E. coli* HB2151 competent cells were transformed with D5 and D8 plasmid DNA. 2×YT medium containing 100 µg/ml of ampicillin and 0.2% glucose was inoculated with a single colony from the freshly transformed plate. The culture was grown at 37° C. till it reached an OD of 0.5 to 0.8 at 600 nm. The culture was then induced with 0.5 mM IPTG and incubated overnight at 30° C. After spinning down the bacteria, the pellet was resuspended with PBS and ruptured with polymixin B. The cellular debris was removed by centrifugation and the two six-histidine tagged Fab's ("six-histidine" disclosed as SEQ ID NO: 53) were purified using Ni-NTA resin. The proteins were eluted with 200 mM imidazole. Finally, the two Fabs were through a SD-200 column (gel-filtration chromatography) for another round of purification. FIG. 1 shows the SDS-PAGE profile of the expressed and purified ADAM17 D+C as well as Fabs D5 and D8 in absence and presence of beta-mercaptoethanol.

These two Fabs (D5 and D8) were reformatted to a human IgG1 format and tested for their effects on a triple-negative human breast cancer cell line referred to as MDA-MB-231. It was found that both mAbs significantly inhibited proliferation of the human breast cancer cell line via inhibition of ADAM17-controlled EGFR signaling. Assays were performed as follows: Briefly, MDA-MB-231 cells were grown on coverslips were fixed in 4% paraformaldehyde and stained with the anti-ADAM17 antibodies D5 and D8 at 5 µg/ml, followed by alexa568-labelled anti-human IgG secondary antibody (green). As a control cells were stained with the secondary antibody only. Nuclei were stained with Hoechst (blue) before imaging by confocal microscopy. FIG. 2 shows images of the D5 (FIG. 2B), D8 (FIG. 2C), and control (FIG. 2D) stained MDA-MB-231 cells respectively. Additionally, an ALAMARBLUE cell viability assay was performed for quantitation, and fluorescence was measured at 590 nm. FIG. 2A shows the results of this ALAMARBLUE cell viability assay in graph form.

Affinity-maturation libraries of D8 and D5 were constructed by targeted mutagenesis. After 3 rounds of selection the affinity matured clones were enriched and a panel of 17 affinity matured clones derived from D5 and D8 were selected based on sequencing results, and based on their $EC_{50}$ and $K_d$ values. Kinetic analysis of the affinity matured clones was performed using an Octet® Red96 device at 25° C. Antibodies were captured on anti-human Fab-CH1 (FAB2G) biosensors. Loaded biosensors were then dipped into a dilution of antigen at variable concentrations (500 nM start, 1:2 down, 7 points). Table A and Table B below show the results of this kinetic analysis for the affinity matured clones.

ALAMARBLUE assays were performed to assess the effects of the affinity-matured clones, as follows. Cells (e.g. breast/ovarian/colon/glioblastoma) were harvested in the log phase of growth (3 days of culture) and cell count was determined. The cell count was adjusted to $1 \times 10^4$ cells/ml. The cells were allowed to adhere and grow for 24 hours in 96-well cell culture plates. They were then exposed to test agents, (e.g. the ADAM17 MAb's described herein) and allowed to grow for additional 38 hours. To determine the effect of a test agent on cell growth, appropriate controls were included e.g. stimulated vs. unstimulated cells. ALAMARBLUE in an amount equal to 10% of the volume in the well was added aseptically. Cultures with ALAMARBLUE were incubated for 6 hrs and proliferation was measured spectrophotometrically by measuring absorbance at 570 and 600 nm. A blank of media only was included.

The percentage difference between treated and control cells was calculated as $((O2 \times A1)-(O1 \times A2) \times 100) \div ((O2 \times P1)-(O1 \times P2))$, where: O1 was the molar extinction coefficient (E) of oxidized ALAMARBLUE (Blue) at 570 nm, O2 was the E of oxidized ALAMARBLUE at 600 nm, A1 was the absorbance of test wells at 570 nm, A2 was the absorbance of test wells at 600 nm, P1 was the absorbance of positive growth control well (cells plus ALAMARBLUE but no test agent) at 570 nm and P2 was the absorbance of positive growth control well (cells plus ALAMARBLUE but no test agent.

Figure 3:
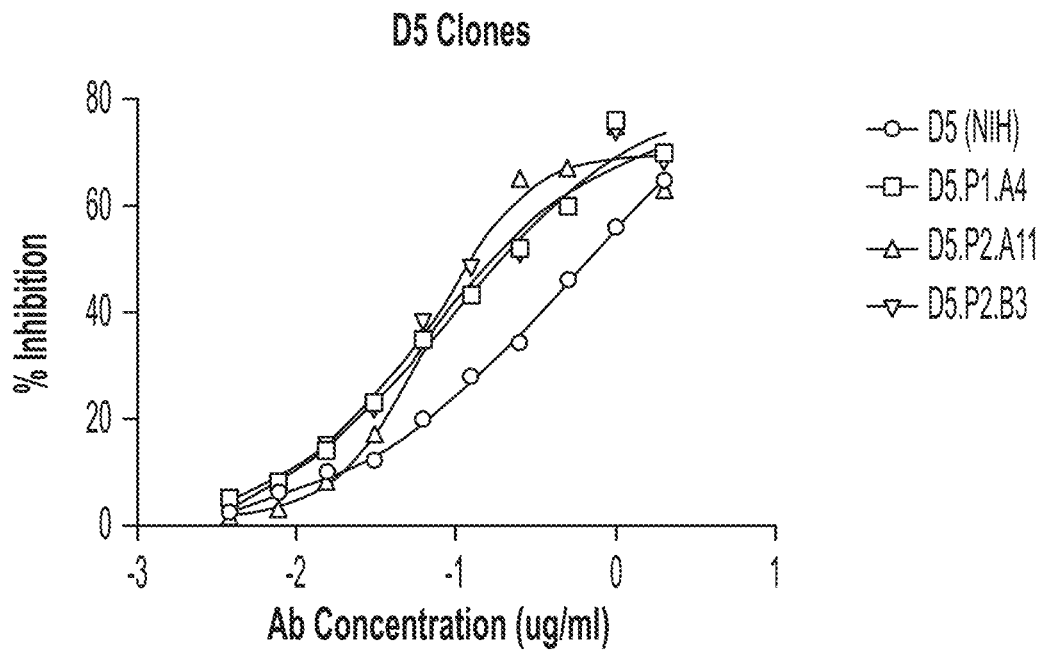
FIG. 3 shows the results of dose-response experiments performed to assess the effects of the parental D5 clone (referred to in the Figure as "D5 (NIH)") and the three most effective affinity-matured clones derived from D5 (namely "D5. P1. A4," "D5. P2. A11," and "D5. P2. B3") on proliferation of the MDA-MB-231 cell line—as quantified using an ALAMARBLUE cell viability assay. The figure provides dose response curves for each antibody—with % inhibition of proliferation plotted against antibody concentration.
Figure 4:
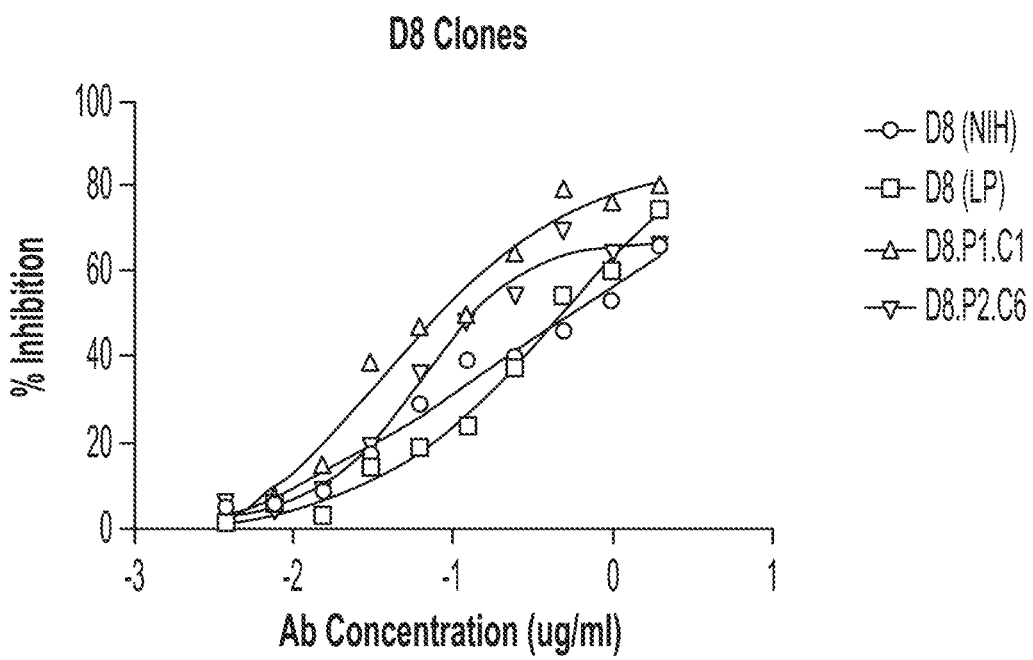
FIG. 4 shows the results of dose-response experiments performed to assess the effects of two separate batches of the parental D8 clone (referred to in the Figure as "D8 (NIH)" and "D8 (LP)"), and the two most effective affinity-matured clones derived from D8 (namely "D8. P1. C1," and "D8. P2. C6.") on proliferation of the MDA-MB-231 cell line—as quantified using an ALAMARBLUE cell viability assay. The figure provides dose response curves for each antibody—with % inhibition of proliferation plotted against antibody concentration.

Five of the affinity-matured clones were found to inhibit proliferation of the MDA-MB-231 triple negative breast cancer cell line with an $IC_{50}$ 5-fold to 10-fold lower than that of their respective parental antibodies—i.e. D5 or D8. as shown in FIG. 3 and FIG. 4.

FIG. 3 shows the results of dose-response experiments performed to assess the effects of the parental D5 clone and the three most effective affinity-matured clones on proliferation of the MDA-MB-231 cell line. An ALAMARBLUE

TABLE A

| Loading Sample ID | Sample ID | KD (M) | Kon(1/Ms) | Kdis(1/s) | Full X^2 | Full R^2 |
|---|---|---|---|---|---|---|
| D5 | ADAM17 | 4.3E−08 | 9.0E+04 | 3.8E−03 | 0.0027 | 0.9849 |
| D5.P1.A4 | ADAM17 | 5.3E−09 | 4.3E+05 | 2.3E−03 | 0.0078 | 0.9847 |
| D5.P1.E4 | ADAM17 | 8.8E−09 | 4.0E+05 | 3.6E−03 | 0.0061 | 0.9683 |
| D5.P1.E8 | ADAM17 | 2.9E−09 | 8.5E+05 | 2.5E−03 | 0.0052 | 0.9892 |
| D5.P1.G4 | ADAM17 | 7.7E−09 | 2.9E+05 | 2.2E−03 | 0.0106 | 0.9922 |
| D5.P2.B3 | ADAM17 | 4.9E−09 | 2.4E+05 | 1.2E−03 | 0.0038 | 0.9977 |

TABLE B

| Loading Sample ID | Sample ID | KD (M) | Kon(1/Ms) | Kdis(1/s) | Full X^2 | Full R^2 |
|---|---|---|---|---|---|---|
| D5.P1.B3 | ADAM17 | 4.7E−09 | 3.3E+05 | 1.6E−03 | 0.0098 | 0.9955 |
| D5.P1.G6 | ADAM17 | 6.1E−09 | 2.4E+05 | 1.4E−03 | 0.0058 | 0.9948 |
| D5.P1.A11 | ADAM17 | 3.9E−09 | 2.9E+05 | 1.1E−03 | 0.0074 | 0.9969 |
| D5.P1.H6 | ADAM17 | 5.8E−09 | 2.2E+05 | 1.3E−03 | 0.0082 | 0.9941 |
| D8 | ADAM17 | 4.0E−09 | 2.6E+05 | 1.1E−03 | 0.0056 | 0.9967 |
| D8.P1.C1 | ADAM17 | 3.1E−09 | 3.7E+05 | 1.1E−03 | 0.0135 | 0.9953 |
| D5.P1.C4 | ADAM17 | 3.3E−09 | 3.4E+05 | 1.1E−03 | 0.0136 | 0.9954 |
| D5.P1.C8 | ADAM17 | 2.5E−09 | 2.4E+05 | 6.1E−04 | 0.0039 | 0.9983 |
| D5.P1.D2 | ADAM17 | 4.0E−09 | 4.2E+05 | 1.7E−03 | 0.0216 | 0.9910 |
| D5.P1.H2 | ADAM17 | 2.9E−09 | 2.7E+05 | 8.0E−04 | 0.0065 | 0.9961 |
| D5.P1.A2 | ADAM17 | 2.3E−09 | 3.0E+05 | 7.1E−04 | 0.0058 | 0.9961 |
| D5.P2.C6 | ADAM17 | 3.3E−09 | 2.3E+05 | 7.5E−04 | 0.0039 | 0.9975 |
| D5.P2.H6 | ADAM17 | 2.1E−09 | 2.2E+05 | 4.7E−04 | 0.0030 | 0.9977 |

The affinity matured Fabs were reformatted to a human IgG1 format and tested in functional assays—in comparison to their respective parental clones.

cell viability assay was performed for quantitation. Proliferation assays were performed with various doses of the parental clone ("D5 (NIH)") as well as with three affinity matured clones ("D5.P1.A4," "D5.P2.A11," and "D5.P2.B3") expressed and purified from HEK293 cells. The three affinity matured clones were found to inhibit proliferation of the MDA-MB-231 cells with an $IC_{50}$ ten-fold lower than that of the parental D5 clone.

FIG. 4 shows the results of dose-response experiments performed to assess the effects of the parental D8 clone and the two most effective affinity-matured clones on proliferation of the MDA-MB-231 cell line. An ALAMARBLUE cell viability assay was performed for quantitation. Proliferation assays were performed with various doses of two separate batches of the parental D8 clone (referred to as "D8 (NIH)" and "D8 (LP)") as well as with two affinity matured clones ("D8.P1.C1," and "D8.P2.C6") expressed and purified from HEK293 cells. The two affinity matured clones were found to inhibit proliferation of the MDA-MB-231 cells with $IC_{50}$ values ten-fold lower and five-fold lower, respectively, than that of the parental D8 clones.

Figure 5:
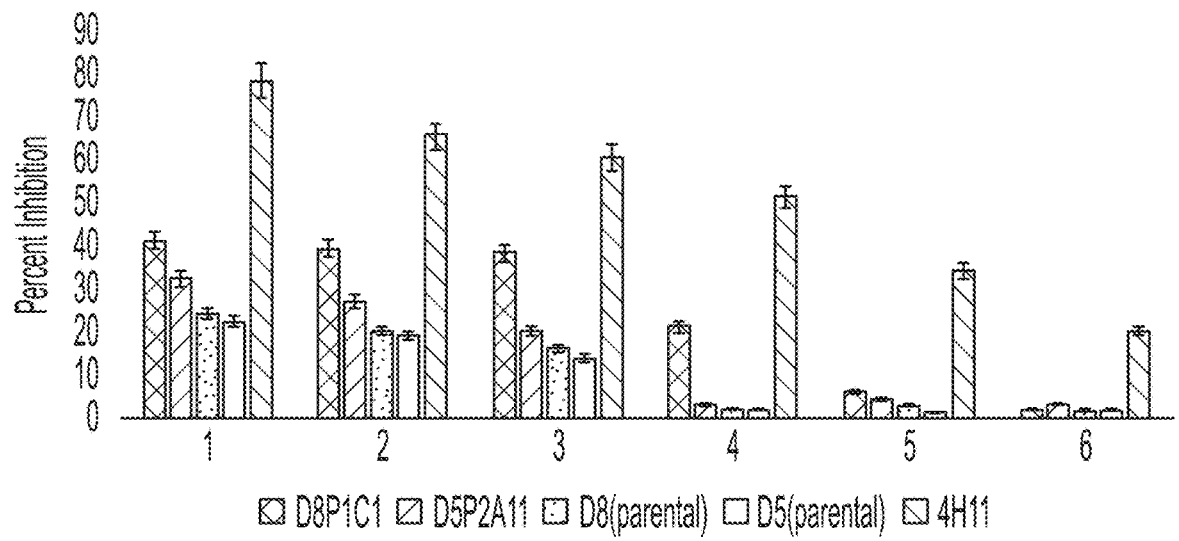
FIG. 5 shows the results of experiments performed to assess the effects of certain antibodies on the proliferation of the ovarian cancer cell line SKOV3 (transduced with MUC 16 ectodomain), as quantified using an ALAMARBLUE cell viability assay. The antibodies tested were the two parental ADAM17 mAbs referred to as D5 and D8, and the affinity matured derivatives of these parental antibodies referred to as D8P1C1 and D5P2A11. The mAb 4H11 anti-MUC16 mAb that recognizes the MUC16 ectodomain was used also. Percentage inhibition of proliferation is shown on the Y axis. Data sets 1-6 (as indicated on the X axis) represent results with various different concentrations of the antibodies, as follows: Set 1: 20 ug/ml; Set 2: 10 ug/ml; Set 3: 5 ug/ml; Set 4: 2.5 ug/ml; Set 5 1.25 ug/ml; Set 6: 0.625 ug/ml. ALA-MARBLUE assay was performed to assess cell viability. Briefly, the cells were grown in 96 well plates for 48 hrs and incubated with varying dilutions of the mAbs for another 36 hrs. Finally, ALAMARBLUE was added and absorbances were recorded at 570 and 600 nm.

FIG. 5 shows the results of experiments performed to assess the effects of certain antibodies on the proliferation of the ovarian cancer cell line SKOV3 (transduced with MUC 16 ectodomain), as quantified using an ALAMARBLUE cell viability assay. The antibodies tested were the two parental ADAM17 mAbs referred to as D5 and D8, and the affinity matured derivatives of these parental antibodies referred to as D8P1C1 and D5P2A11. The mAb 4H11 anti-MUC16 mAb that recognizes the MUC16 ectodomain was used also. Percentage inhibition of proliferation is shown on the Y axis. Data sets 1-6 (as indicated on the X axis) represent results with various different concentrations of the antibodies, as follows: Set 1: 20 ug/ml; Set 2: 10 ug/ml; Set 3: 5 ug/ml; Set 4: 2.5 ug/ml; Set 5 1.25 ug/ml; Set 6: 0.625 ug/ml. ALAMARBLUE assay was performed to assess cell viability. Briefly, the cells were grown in 96 well plates for 48 hrs and incubated with varying dilutions of the mAbs for another 36 hrs. Finally, ALAMARBLUE was added and absorbances were recorded at 570 and 600 nm.

Figure 6:
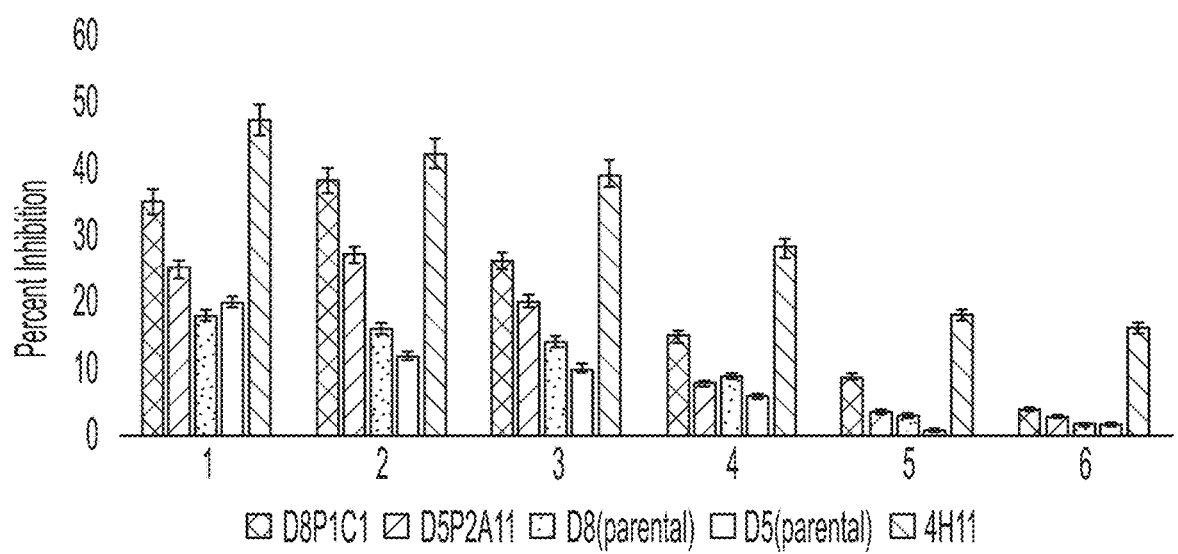
FIG. 6 shows the results of experiments performed to assess the effects of certain antibodies on the proliferation of the ovarian cancer cell line OVCAR3, as quantified using an ALAMARBLUE cell viability assay. The antibodies tested were the two parental ADAM17 mAbs referred to as D5 and D8, and the affinity matured derivatives of these parental antibodies referred to as D8P1C1 and D5P2A11. The mAb 4H11 anti-MUC16 mAb that recognizes the MUC16 ectodomain was used also. Percentage inhibition of proliferation is shown on the Y axis. Data sets 1-6 (as indicated on the X axis) represent results with various different concentrations of the antibodies, as follows: Set 1: 20 ug/ml; Set 2: 10 ug/ml; Set 3: 5 ug/ml; Set 4: 2.5 ug/ml; Set 5 1.25 ug/ml; Set 6: 0.625 ug/ml. ALAMARBLUE assay was performed to assess cell viability. Briefly, the cells were grown in 96 well plates for 48 hrs and incubated with varying dilutions of the mAbs for another 36 hrs. Finally, ALAMARBLUE was added and absorbances were recorded at 570 and 600 nm.

FIG. 6 shows the results of experiments performed to assess the effects of certain antibodies on the proliferation of the ovarian cancer cell line OVCAR3, as quantified using an ALAMARBLUE cell viability assay. The antibodies tested were the two parental ADAM17 mAbs referred to as D5 and D8, and the affinity matured derivatives of these parental antibodies referred to as D8P1C1 and D5P2A11. The mAb 4H11 anti-MUC16 mAb that recognizes the MUC16 ectodomain was used also. Percentage inhibition of proliferation is shown on the Y axis. Data sets 1-6 (as indicated on the X axis) represent results with various different concentrations of the antibodies, as follows: Set 1: 20 ug/ml; Set 2: 10 ug/ml; Set 3: 5 ug/ml; Set 4: 2.5 ug/ml; Set 5 1.25 ug/ml; Set 6: 0.625 ug/ml. ALAMARBLUE assay was performed to assess cell viability. Briefly, the cells were grown in 96 well plates for 48 hrs and incubated with varying dilutions of the mAbs for another 36 hrs. Finally, ALAMARBLUE was added and absorbances were recorded at 570 and 600 nm.

Figure 7A:
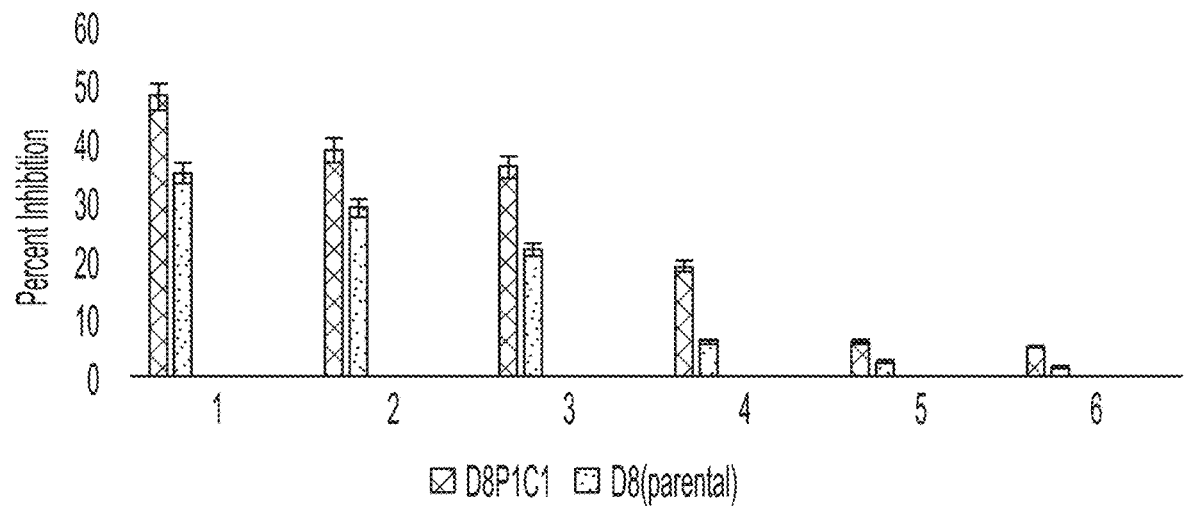
FIG. 7A-B. Proliferation inhibition of the ovarian cancer cell line SKOV3 by the anti-ADAM17 mAbs, D8 (FIG. 7A), D5 (FIG. 7B) and their affinity-matured versions D8P1C1 (FIG. 7A), D5P2A11 (FIG. 7B). Data sets 1-6 were generated using different concentrations of the specified mAbs, as follows: 1: 20 µg/ml; 2:10 µg/ml; 3: 5 µg/ml; 4: 2.5 µg/ml; 5: 1.25 µg/ml; 6: 0.625 µg/ml.
Figure 7B:
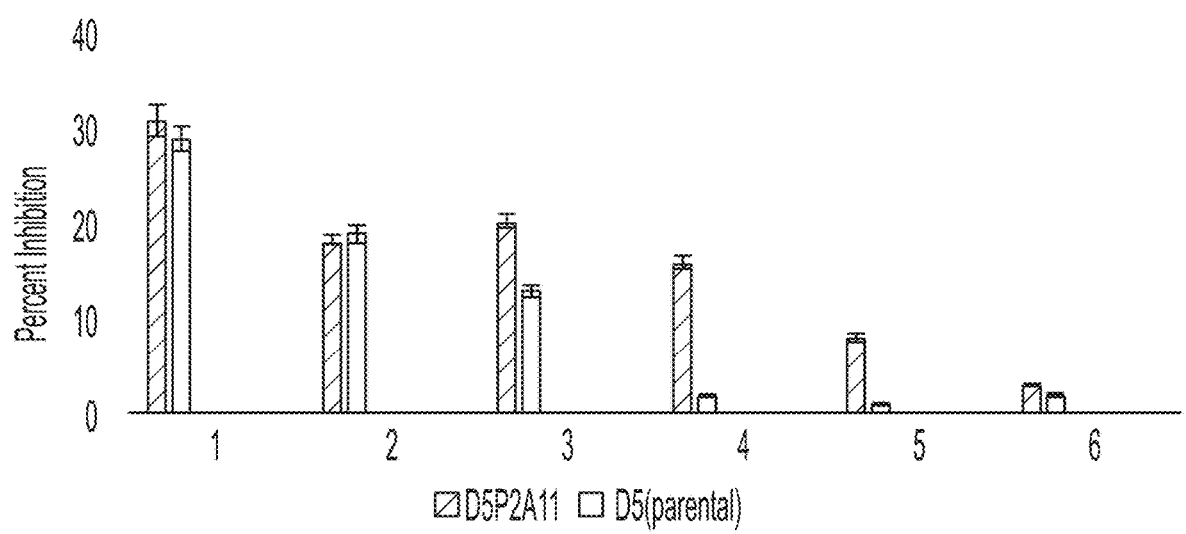
Figure 8A:
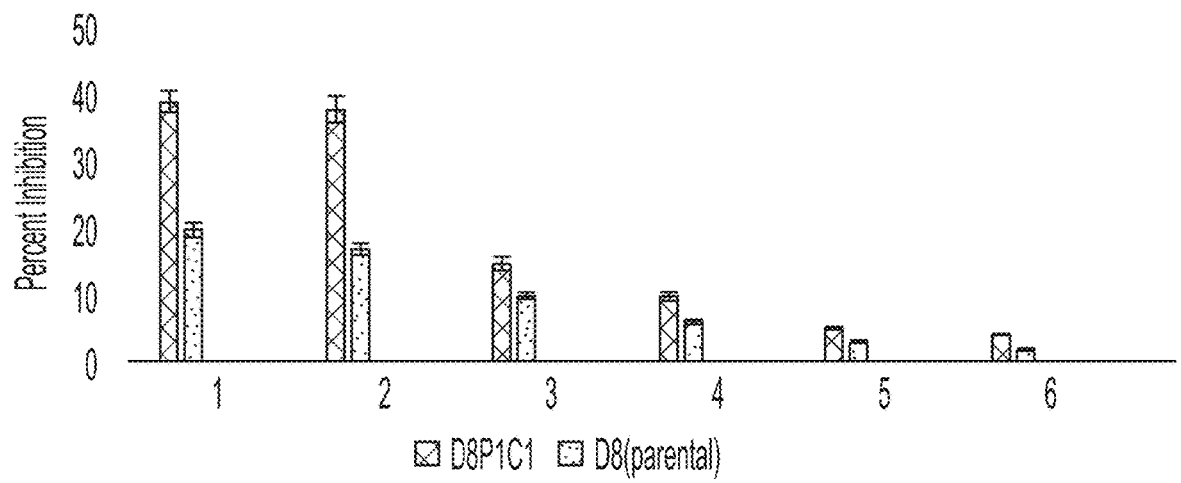
FIG. 8A-B. Proliferation inhibition of the ovarian cancer cell line CaoV3 by the anti-ADAM17 mAbs, D8 (FIG. 8A), D5 (FIG. 8B) and their affinity-matured versions D8P1C1 (FIG. 8A), D5P2A11 (FIG. 8B). Data sets 1-6 were generated using different concentrations of the specified mAbs, as follows: 1: 20 µg/ml; 2:10 µg/ml; 3: 5 µg/ml; 4: 2.5 µg/ml; 5: 1.25 µg/ml; 6: 0.625 µg/ml.
Figure 8B:
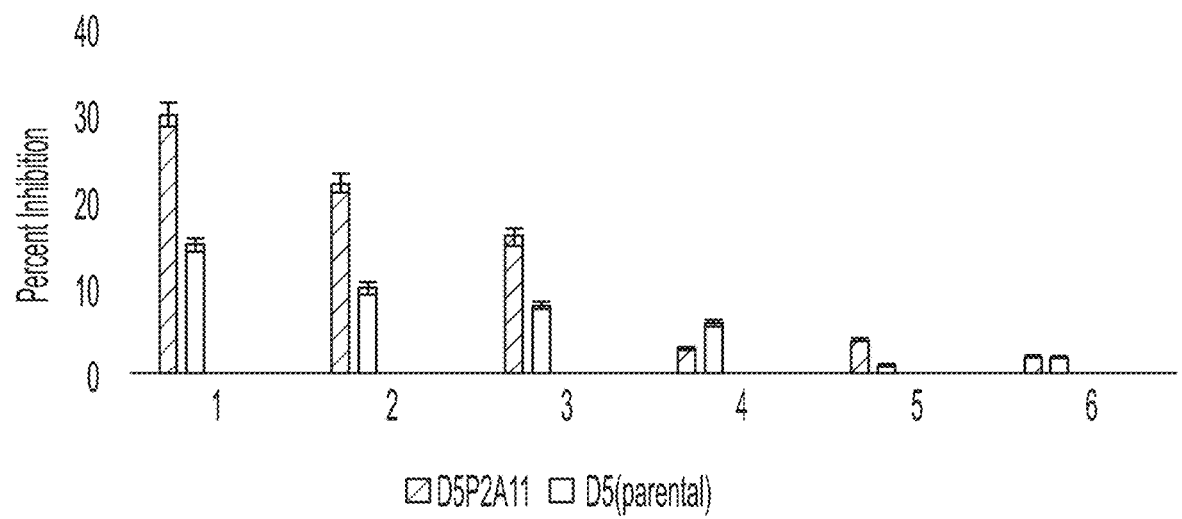
Figure 9A:
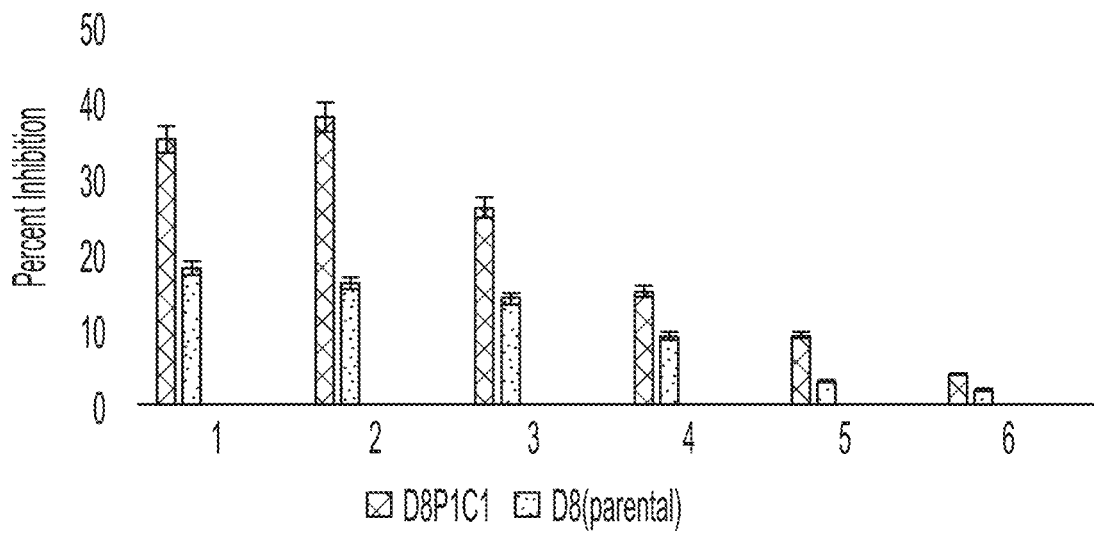
FIG. 9A-B. Proliferation inhibition of the ovarian cancer cell line OVCAR-3 by the anti-ADAM17 mAbs, D8 (FIG. 9A), D5 (FIG. 9B) and their affinity-matured versions D8P1C1 (FIG. 9A), D5P2A11 (FIG. 9B). Data sets 1-6 were generated using different concentrations of the specified mAbs, as follows: 1: 20 µg/ml; 2:10 µg/ml; 3: 5 µg/ml; 4: 2.5 µg/ml; 5: 1.25 µg/ml; 6: 0.625 µg/ml.
Figure 9B:
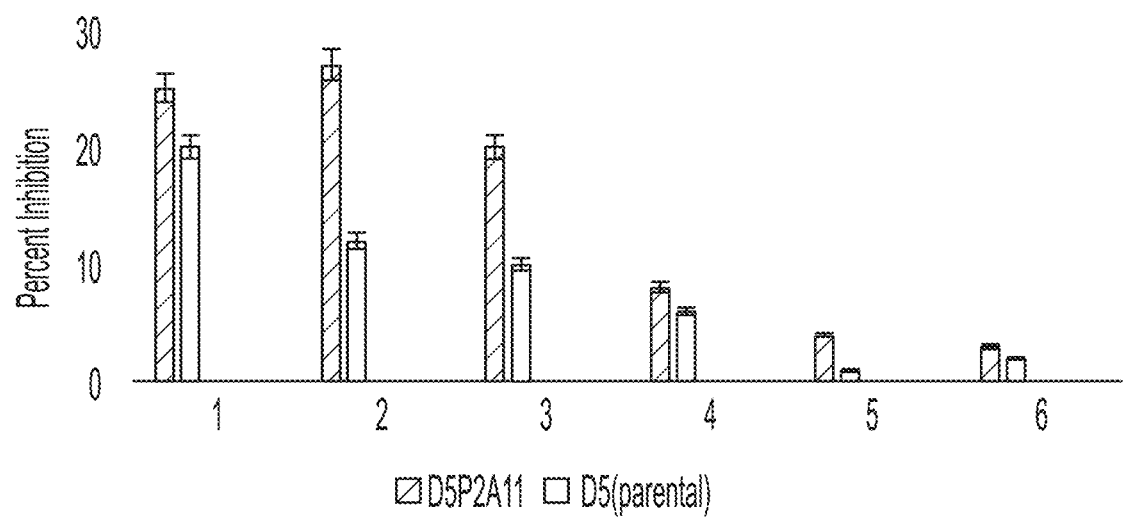
Figure 10A:
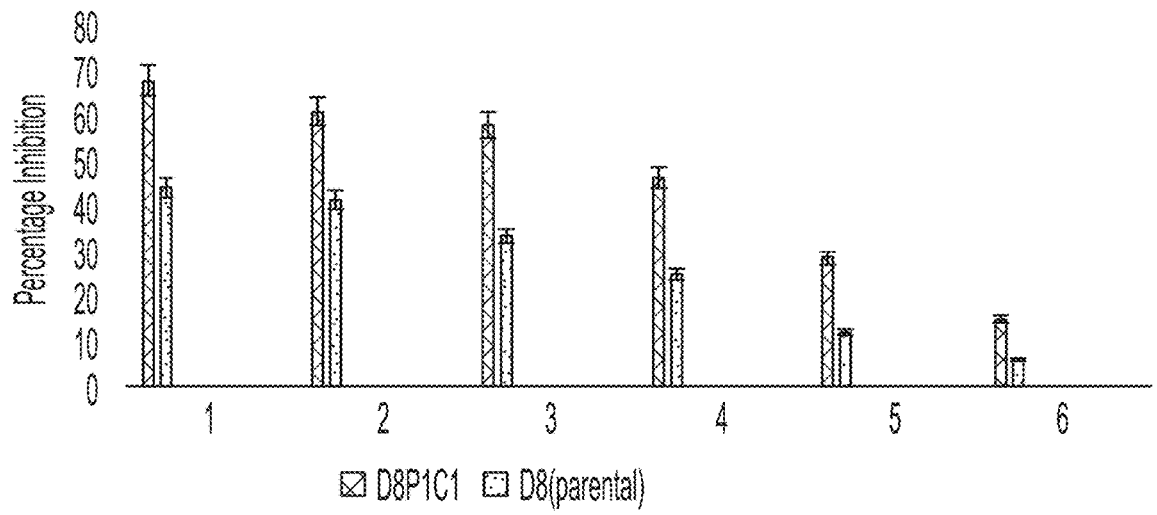
FIG. 10A-B. Proliferation inhibition of the breast cancer cell line SKBR-3 by the anti-ADAM17 mAbs, D8 (FIG. 10A), D5 (FIG. 10B) and their affinity-matured versions D8P1C1 (FIG. 10A), D5P2A11 (FIG. 10B). Data sets 1-6 were generated using different concentrations of the specified mAbs, as follows: 1: 20 µg/ml; 2:10 µg/ml; 3: 5 µg/ml; 4: 2.5 µg/ml; 5: 1.25 µg/ml; 6: 0.625 µg/ml.
Figure 10B:
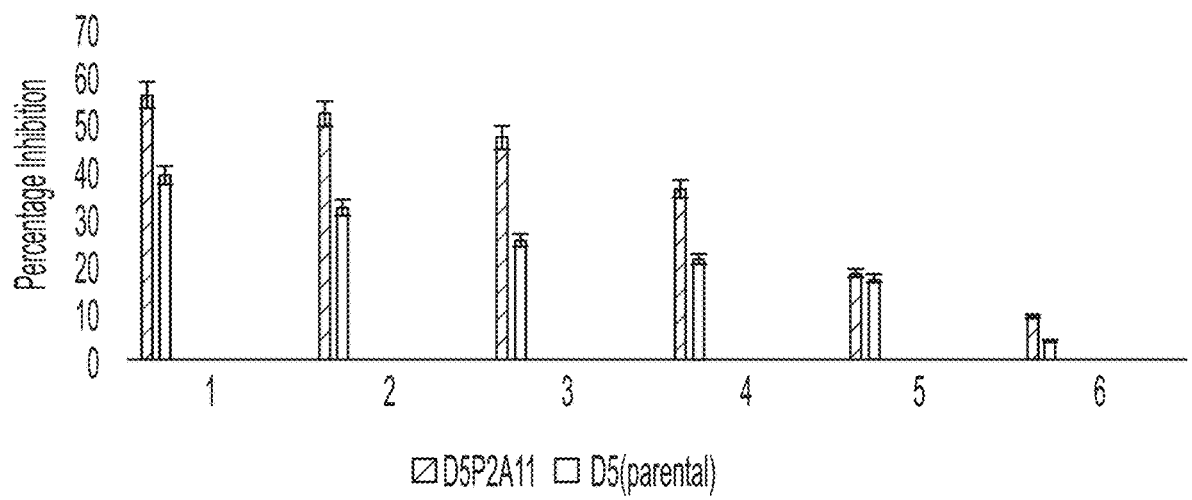
Figure 11A:
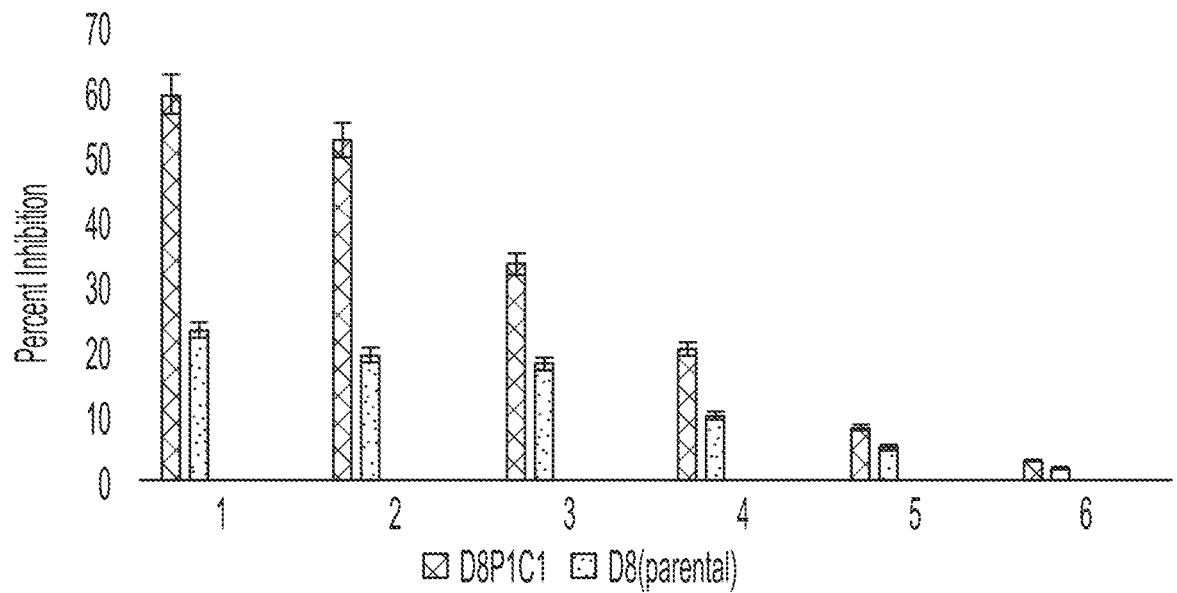
FIG. 11A-B. Proliferation inhibition of the breast cancer cell line MCF-7 by the anti-ADAM17 mAbs, D8 (FIG. 11A), D5 (FIG. 11B) and their affinity-matured versions D8P1C1 (FIG. 11A), D5P2A11 (FIG. 11B). Data sets 1-6 were generated using different concentrations of the specified mAbs, as follows: 1: 20 µg/ml; 2:10 µg/ml; 3: 5 µg/ml; 4: 2.5 µg/ml; 5: 1.25 µg/ml; 6: 0.625 µg/ml.
Figure 11B:
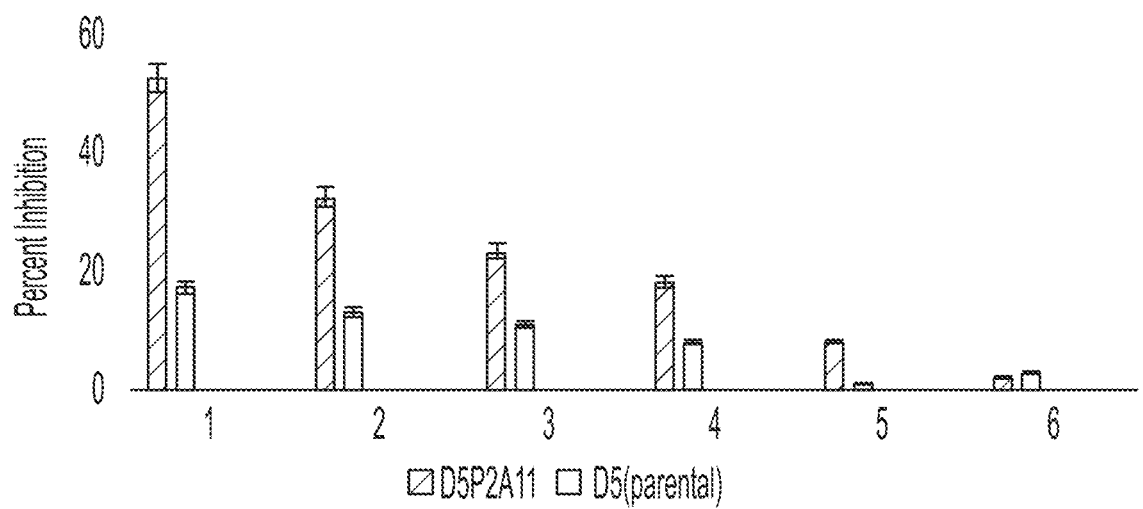
Figure 12A:
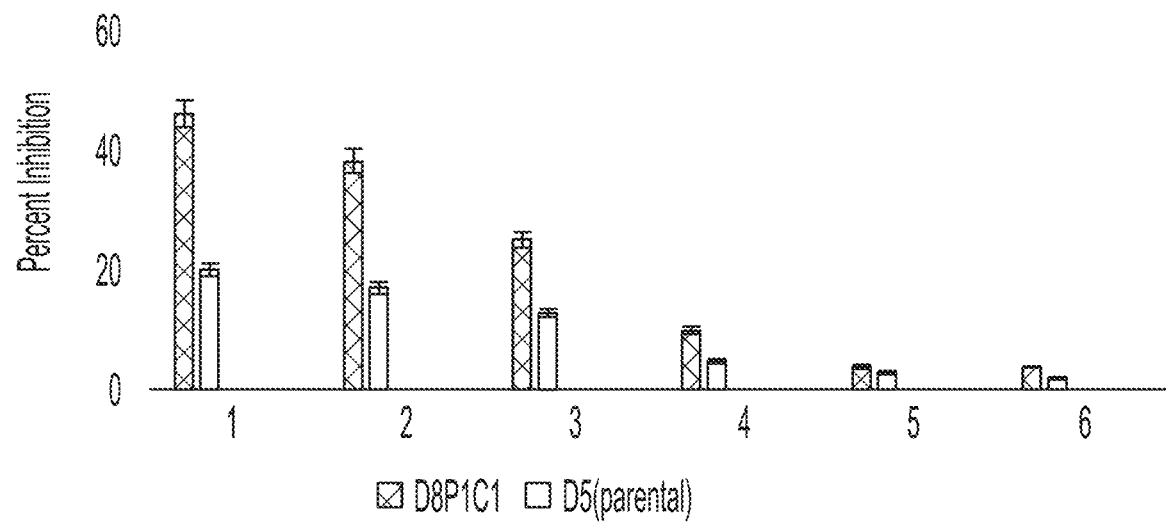
FIG. 12A-B. Proliferation inhibition of the colon cancer cell line LIM1215 by the anti-ADAM17 mAbs, D8 (FIG. 12A), D5 (FIG. 12B) and their affinity-matured versions D8P1C1 (FIG. 12A), D5P2A11 (FIG. 12B). Data sets 1-6 were generated using different concentrations of the specified mAbs, as follows: 1: 20 µg/ml; 2:10 µg/ml; 3: 5 µg/ml; 4: 2.5 µg/ml; 5: 1.25 µg/ml; 6: 0.625 µg/ml.
Figure 12B:
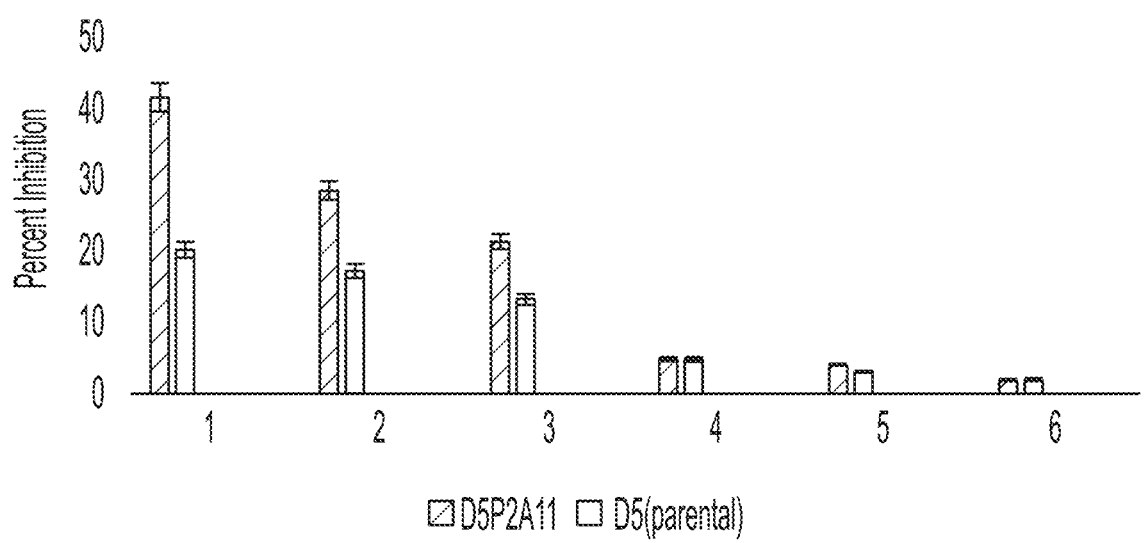

Further experiments were performed to evaluate the viability of three ovarian [SKOV-3 (FIG. 7A, B), Caov3 (FIG. 8A, B), OVCAR3 (FIG. 9A, B)], two breast [SKBR-3 (FIG. 10A, B), MCF-7 (FIG. 11A, B)], one colon [LIM1215, (FIG. 12A, B)], and one glioblastoma [U87 MG, (FIG. 13A, B)], cell lines using ALAMARBLUE assays similar to those performed for MDA-MB-231 (FIG. 3 and FIG. 4). We evaluated how the parental anti-ADAM17 mAbs D8, D5 and their affinity-matured versions D8P1C1, D5P2A11, affect the viability of these cancer cell lines. These cell lines are known to overexpress EGFR/HER2 (the signaling of which depends on ADAM17 activity). The ALAMARBLUE assay data demonstrated that: (1) the affinity-matured version D8P1C1 was the most potent in inhibiting proliferation of these cell lines; (2) the mAbs were more effective in inhibiting EGFR/IER2-dependent breast cancer lines as compared to ovarian/colon/glioblastoma. This could be attributed, in part, to other pathways mediating proliferation of the cancer lines, such as the MUC16 pathway in case of ovarian cancer. FRET-based enzymatic cleavage assays were performed using a peptide (substrate for ADAM17) sequence derived from TNF-alpha. The peptide substrate contains a highly fluorescent 7-methoxycoumarin group that is efficiently quenched by resonance energy transfer to the 2,4-dinitrophenyl group. ADAM17 cleaves the amide bond between the fluorescent and quencher group causing an increase in fluorescence (R&D Systems, Cat Number ES003). Our goal was to determine the effects of the two anti-ADAM17 mAbs on ADAM17-mediated substrate cleavage. We incubated the enzymatically active ADAM17 ectodomain with the D8P1C1 and D5P2A11 at a 1:1 molar ratio. The assay was performed in 20 mM Tris pH 8.8, 2 uM zinc chloride and 50 uM substrate (FIG. 14). For comparison, we included another commercially available anti-ADAM17 mAb MEDI3622 (MedImmune) that binds to a hairpin loop in the protease domain of ADAM17. The results indicated that the affinity-matured anti-ADAM17 mAb D8P1C1 was the most effective in inhibiting substrate cleavage. Since the mAb binds the substrate-binding module of ADAM17, it can be speculated that upon binding it blocks the access of the substrate.

For each of the 5 "lead" molecules described above (i.e. D5.P1.A4, D5.P2.A11, D5.P2.B3, D8.P1.C1, and D8.P2.C6), various amino acid sequences are provided in Tables 1 and 2—which are provided above in the "Detailed Description" section of this patent disclosure. The sequences provided include full light and heavy chain sequences of the IgG1 formatted clones (Table 1), variable domain sequences (Table 1—location of variable domains with full sequences are shown), and CDR sequences (Tables 1 and 2).

Example 2

In Vivo Bio-Distribution Studies of ADAM17 Binding Molecules

In order to understand relationships between ADAM17 binding molecule dosing and tumor delivery, and to estimate therapeutic efficacy and therapeutic index, pharmacokinetic profiles of the affinity matured ADAM17 binding molecules described herein are performed. Positron Emission Tomography (PET) is a well-established and widely used molecular imaging modality both in pre-clinical and clinical setting. PET offers the ability to quantitatively measure biological and receptor-based processes using a variety of radiolabeled probes (23, 24). To assess pharmacokinetic behavior of the affinity matured ADAM17 binding molecules described herein, the molecules are radiolabeled with zirconium using well-established protocols (25). Zirconium-89 may be used as the PET isotope even though it requires DFO conjugation, as opposed to using, for example, iodine-124—which can be attached to the binding molecules directly without the need for any modification, because iodine-124 labeled antibodies are prone to deiodination, which can lead to underestimation of the amount of antibody at the tumor, and also because DFO conjugation has no measurable impact on the pharmacokinetics of the antibodies. Therefore, zirconium-89 PET labeled binding molecules are used to provide an accurate estimation of the concentration of the binding molecules at the tumor site, and elsewhere (e.g. in other organs) (25). The radiochemical stability of the zirconium-89 labeled binding molecules is assessed by radio thin layer chromatography. Purification is performed using a PD10 desalting column and eluting the products with PBS. PET imaging and quantification is performed as follows. MDA-MB-231 tumors are established in SCID mice by subcutaneous (s.c.) administration of $7\times10^6$ MDA-MB-231 cells in 200 µl PBS/30% growth factor reduced Matrigel (BD) in the right dorsal mouse flank. When tumor volumes reach 250-500 mm$^3$ (for example measured by calipers, volume=[length×width2]/2), mice are used for imaging experiments. Cohorts of mice (n=10 mice per cohort) are treated with 89Zr-labeled binding molecules (~150 µCi/100-300 µg of binding molecule) administered via the tail vein. Images are acquired between 1-120 hours post tracer administration at multiple timepoints (for example, up to 10 timepoints) to generate an in vivo pharmacokinetic profile. Two-dimensional regions of interest (ROI) and time-activity curves (TAC) are generated to calculate the average±SD % ID/g for analysis. ID is injected dose.

To further validate the PET imaging data, acute ex vivo bio-distribution studies are performed in MDA-MB-231 xenograft bearing SCID mice. Cohorts of mice (n=5) are treated with the 89Zr-labeled binding molecules (~150 µCi/ 100-300 µg of binding molecule) and mice are euthanized by $CO_2$ (g) asphyxiation at 4, 24, 48, 72, 96 and 120 h time points. 16 tissues (including the tumor tissue) are removed, rinsed in water, dried in air for 5 min, weighed and counted on a gamma-counter for accumulation of radioactivity. The amount of radioactivity administered to each animal is measured by measuring the radioactivity in the syringe before and after injection using a dose calibrator. The counts from these gamma-counter measurements are converted to activity using a standard calibration curve derived from counting known samples. Count data is background- and decay-corrected and the tissue uptake, measured in units of percentage injected dose per gram (% ID/g), for each sample is calculated by normalization to the total amount of activity injected. The mass of each organ is determined and then each sample is counted using an automatic gamma counter. Counts are converted into activity concentration (% ID/g), after decay and background correction by normalization to the total activity injected into the respective animal.

The above in vivo mouse experiments can be performed using engineered chimeras of the 5 lead ADAM17 binding molecules comprising a murine constant region and/or murine framework regions, if desired.

Example 3

In Vivo Pre-Clinical Testing of ADAM17 Binding Molecules in a Breast Cancer Model Since the mAb D8P1C1 was the most effective in inhibiting the proliferation of the breast cancer cell line MDA-MB-231, its efficacy was evaluated in a preclinical setting using a xenograft assay (human tumor implanted into mice). For these studies 6-8 week old athymic nude mice (n=5) were used. 10 million cells were implanted per mouse (subcutaneous) and each mouse was injected with D8P1C1 (referred to as D8 in FIG. 15) intraperitoneally, at dose of 15 mg/kg, biweekly for 4 weeks. PBS was used as a vehicle control. The mean tumor volume of the control and treated groups was measured. Percent tumor growth inhibition was calculated to be 76.8 percent (FIG. 15). This in vivo preclinical data is thus in excellent agreement with the in vitro cell viability data.

Example 4

In Vivo Pre-Clinical Testing of ADAM17 Binding Molecules, Alone and in Combination with Other Active Agents The ADAM17 binding molecules described herein are tested in three different mouse xenograft models—(a) a breast cancer model, (b) a colon cancer model, and (c) a glioma model. Effective synergistic co-treatment of breast cancer xenografts with an ErbB kinase and a broad-spectrum ADAM inhibitor (INCB3619) has been demonstrated.

Anti-tumor effects of the five lead ADAM17 binding molecules described herein (i.e. D5.P1.A4, D5.P2.A11, D5.P2.B3, D8.P1.C1, and D8.P2.C6) are assessed in mice bearing EGFR-dependent MDA-MB-231 xenografts. The anti-tumor effects of these binding molecules are evaluated alone, as well as in combination with other known therapeutics, including, but not limited to, the chemotherapeutic agent paclitaxel. Athymic nu/nu mice are used as the host for the MDA-MB-231 xenografts (female, ages 6-10 weeks). Around 30 animals are used per model (10 animals/group; 2 antibody treatment groups, and one vehicle only control group).

The anti-tumor effects of the anti-ADAM17 binding molecules are also evaluated in mice bearing EGFR-dependent LIM1215 xenografts, and mice bearing anti-EGFR resistant HCT116 colon tumor xenografts. The effect of the ADAM17 binding molecules is evaluated alone and in combination with Cetuximab. These studies demonstrate the extent to which inhibition of ADAM17 with the binding molecules of the invention can overcome anti-EGFR resistance.

In addition, xenograft models of EGFR over-expressing glioblastoma are evaluated for single (i.e. ADAM17 binding molecules alone) and anti-EGFR combination treatment. The glioma lines U87 and U251 are used.

For each of the in vivo preclinical models described above, tumor-bearing mice are treated i.p. twice weekly with the ADAM17 binding molecules (or a control) either alone or in combination with other approved therapeutic agents, and the effects of the administered agents on growth characteristics, viability/number of targeted cells, and the architecture and integrity of the tumor microenvironment, are evaluated. Tumors are analyzed during treatment and post treatment by immunohistochemistry (IHC), flow cytometry, and Western blotting to assess proliferation, (Ki67)/apoptosis (TUNEL, Anexin), and the effects on the tumor stroma (tenascin, CD90) and microvasculature (CD31, CD105, NG2, cadherin). Tumor regression is assessed.

The above in vivo mouse experiments can be performed using engineered chimeras of the 5 lead ADAM17 binding molecules comprising a murine constant region and/or murine framework regions, if desired.

Example 5

Formulation & Buffer Optimization

Affinity matured clones D5.P2.A11 & D8.P1.C1 were chimerized by replacing the human IgG1 Fc region with a murine IgG2a sequence. Chimerized variants were expressed in CHO cells, purified by Protein A column and buffer exchanged into one of 5 buffer formulations: 100 mM HEPES, 100 mM NaCl, 50 mM NaOAc, pH 6.0 (herein denoted B0), 10 mM Histidine, 100 mM NaCl, pH 5.5 (herein denoted B1), 10 mM Histidine, 100 mM NaCl, pH 6.5 (herein denoted B2), 10 mM citrate, 100 mM NaCl, pH 5.0 (herein denoted B3), and 10 mM citrate, 100 mM NaCl, pH 6.0 (herein denoted B4). D5 and D8 variants were then subjected to either 3 freeze/thaw cycles or heat stress at 40°

C. and evaluated at 7, 14 and 30 days for % monomeric content by SEC-HPLC. The results are shown in Table 4. Finally, selected formulations were evaluated for inhibition of proliferation of MDA-MB-231 cells using the same methodology as was used to generate the data presented in FIG. 4. The results of these experiments are shown in FIG. 16. Based on this data, clone D5.P2.A11 was formulated in buffer formulation B2 and clone D8.P1.C1 was formulated in buffer B1.

TABLE 4

|  |  | T0 | T7 | T14 | T30 | F/T |
|---|---|---|---|---|---|---|
| D5.P2.A11 | B0 | 100 | 78.14 | 75.56 | 76.18 | 100 |
| hFab-mFc | B1 | 100 | 85.56 | 75.27 | 78.66 | 100 |
| (PP15542) | B2 | 100 | 81.93 | 84.22 | 84.17 | 100 |
|  | B3 | 100 | 87.7 | 73.15 | 77.66 | 100 |
|  | B4 | 100 | 82.74 | 78.52 | 79.85 | 100 |

|  |  | T0 | T7 | T14 | T30 | F/T |
|---|---|---|---|---|---|---|
| D8.P1.C1 | B0 | 95.45 | 79.2 | 73.68 | 79.9 | 94.6 |
| hFab-mFc | B1 | 95.32 | 75.22 | 77.99 | 80.54 | 96.14 |
| (PP15543) | B2 | 95.4 | 79.87 | 75.33 | 76.7 | 97.01 |
|  | B3 | 97.24 | 77.6 | 76.96 | 76.16 | 96.4 |
|  | B4 | 96.72 | 74.03 | 75.33 | 78.92 | 98.57 |

REFERENCE LIST

1. Janes P W, Saha N, Barton W A, Kolev M V, Wimmer-Kleikamp S H, Nievergall E, Blobel C P, Himanen J P, Lackmann M, Nikolov D B. Adam meets Eph: an ADAM substrate recognition module acts as a molecular switch for ephrin cleavage in trans. Cell. 2005 Oct. 21; 123(2): 291-304.
2. Atapattu L, Saha N, Llerena C, Vail M E, Scott A M, Nikolov D B, Lackmann M, Janes P W. Antibodies binding the ADAM10 substrate recognition domain inhibit Eph function. J Cell Sci. 2012 Dec. 15; 125(Pt 24): 6084-93.
3. Atapattu L, Saha N, Chheang C, Eissman M F, Xu K, Vail M E, Hii L, Llerena C, Liu Z, Horvay K, Abud H E, Kusebauch U, Moritz R L, Ding B S, Cao Z, Rafii S, Ernst M, Scott A M, Nikolov D B, Lackmann M, Janes P W. 2016. An activated form of ADAM10 is tumor selective and regulates cancer stem-like cells and tumor growth. J Exp Med. August 22; 213(9): 1741-57. PMCID: PMC 4995075
4. U.S. Pat. No. 7,960,513, Monoclonal antibodies raised recognizing the ADAM substrate recognition site and blocking substrate access to this site. Lackmann, M., Janes, P W., Nikolov, D B., Saha, N., 2011 Jun. 11, granted. U.S. National Stage entry of PCT/AU2005/001917 (WO2006063415): Regulation of metalloprotease cleavage of cell surface proteins. Lackmann, M., Janes, P W., Nikolov, D B., Saha, N. 2006 Jun. 22, granted.
5. Seals D F, Courtneidge S A. The ADAMs family of metalloproteases: multidomain proteins with multiple functions. Genes Dev. 2003 Jan. 1; 17(1): 7-30. Review.
6. Wolfsberg T G, White J M. ADAM metalloproteinases. In: Barrett A J, Rawlings N D, Woessner J F, eds. Handbook of Proteolytic Enzymes. Second Edition. London: Academic Press, 2004:709-14
7. White J M. ADAMs: modulators of cell-cell and cell-matrix interactions. Curr Opin Cell Biol. 2003 October; 15(5): 598-606. Review.
8. Reddy P, Slack J L, Davis R, Cerretti D P, Kozlosky C J, Blanton R A, Shows D, Peschon J J, Black R A. Functional analysis of the domain structure of tumor necrosis factor-alpha converting enzyme. J Biol Chem. 2000 May 12; 275(19): 14608-14.
9. Smith K M, Gaultier A, Cousin H, Alfandari D, White J M, DeSimone D W. The cysteine-rich domain regulates ADAM protease function in vivo. J Cell Biol. 2002 Dec. 9; 159(5): 893-902.
10. Yarden Y, Sliwkowski M X. Untangling the ErbB signalling network. Nat Rev Mol Cell Biol. 2001 February; 2(2): 127-37.
11. Harris R C, Chung E, Coffey R J. EGF receptor ligands. Exp Cell Res. 2003 Mar. 10; 284(1): 2-13. Review.
12. Zhou B B, Peyton M, He B, Liu C, Girard L, Caudler E, Lo Y, Baribaud F, Mikami I, Reguart N, Yang G, Li Y, Yao W, Vaddi K, Gazdar A F, Friedman S M, Jablons D M, Newton R C, Fridman J S, Minna J D, Scherle P A. Targeting ADAM-mediated ligand cleavage to inhibit HER3 and EGFR pathways in nonsmall cell lung cancer. Cancer Cell. 2006 July; 10(1): 39-50.
13. Murphy G. The ADAMs: signaling scissors in the tumor microenvironment. Nat Rev Cancer. 2008 December; 8(12): 929-41
14. Blobel C P, Carpenter G, Freeman M. The role of protease activity in ErbB biology. Exp Cell Res. 2009 Feb. 15; 315(4): 671-82.
15. Yoo J, Perez C E, Nie W, Sinnett-Smith J, Rozengurt E. TNF-alpha and LPA promote synergistic expression of COX-2 in human colonic myofibroblasts: role of LPA-mediated transactivation of upregulated EGFR. BMC Gastroenterol. 2013 May 20; 13(1): 90.
16. McGowan P M, Mullooly M, Caiazza F, Sukor S, Madden S F, Maguire A A, Pierce A, McDermott E W, Crown J, O'Donovan N, Duffy M J. ADAM-17: a novel therapeutic target for triple negative breast cancer. Ann Oncol. 2013, February 24 (2): 362-369
17. Rio C, Buxbaum J D, Peschon J J, Corfas G. Tumor necrosis factor-alphaconverting enzyme is required for cleavage of erbB4/HER4.J Biol Chem. 2000 Apr. 7; 275(14): 10379-87.
18. Wang S E, Xiang B, Guix M, Olivares M G, Parker J, Chung C H, Pandiella A, Arteaga C L. Transforming growth factor beta engages TACE and ErbB3 to activate phosphatidylinositol-3 kinase/Akt in ErbB2-overexpressing breast cancer and desensitizes cells to trastuzumab. Mol Cell Biol. 2008 September; 28(18): 5605-20.
19. Drag M, Salvesen G S. Emerging principles in protease-based drug discovery. Nat Rev Drug Discov 2010; 9:690-701; PMID: 20811381
20. Turk B. Targeting proteases: successes, failures and future prospects. Nat Rev Drug Dis 2006; 5:785-99; PMID: 16955069
21. Shirshendu DasGupta, Prashant R. Murumkar, Rajani Giridhar, Mange Ram Yadav. Current perspective of TACE inhibitors: A review Bioorganic & Medicinal Chemistry 17 (2009) 444-459.
22. Zhongyu Zhu and Dimiter S. Dimitrov. Construction of a Large Naïve Human Phage-Displayed Fab Library Through One-Step Cloning Methods Mol Bio. 2009. 525: 129-xv.
23. Lee S G, Gangangari K, Kalidindi T M, Punzalan B, Larson S M, Pillarsetty N V. 2016. Copper-64 labeled liposomes for imaging bone marrow. Nucl Med Biol. December; 43 (12): 781-787.
24. Zanzonico P, Carrasquillo J A, Pandit-Taskar N, O'Donoghue J A, Humm J L, Smith-Jones P, Ruan S, Divgi C, et al. 2015. PET-based compartmental modeling of (124) I-A33 antibody: quantitative characterization of patient-specific tumor targeting in colorectal cancer. Eur J Nucl Med Mol Imaging. October; 42 (11): 1700-6.
25. Vosjan M J, Perk L R, Visser G W, Budde M, Jurek P, Kiefer G E, van Dongen G A. 2010. Conjugation and radiolabeling of monoclonal antibodies with zirconium-89 for PET imaging using the bifunctional chelate p-iso-thiocyanatobenzyl-desferrioxamine. Nat. Protocol. April; 5(4): 739-43.
26. Himanen J P, Saha, N, Nikolov D B. 2007. Cell-cell signaling via Eph receptors and ephrins. Curr Opin Cell Biol. October 19 (5): 534-42. PMCID: PMC 3327877
28. PCT application PCT/AU2015/050036, filed as U.S. application Ser. No. 15/116,487, claiming priority to U.S. provisional patent application No. 61/935,552.

The invention claimed is:

1. An isolated ADAM17 binding molecule comprising one of:
- (a) (i) a heavy chain variable region comprising: a CDR H1 domain comprising SEQ ID NO. 17, a CDR H2 domain comprising SEQ ID NO. 18, and a CDR H3 domain comprising SEQ ID NO. 19, and
  - (ii) a light chain variable region comprising: a CDR L1 domain comprising SEQ ID NO. 20, a CDR L2 domain comprising SEQ ID NO. 21, a CDR L3 domain comprising SEQ ID NO. 22; or
- (b) (i) a heavy chain variable region comprising: a CDR H1 domain comprising SEQ ID NO. 23, a CDR H2 domain comprising SEQ ID NO. 24, and a CDR H3 domain comprising SEQ ID NO. 25, and
  - (ii) a light chain variable region comprising: a CDR L1 domain comprising SEQ ID NO. 26, a CDR L2 domain comprising SEQ ID NO. 27, a CDR L3 domain comprising SEQ ID NO. 28; or
- (c) (i) a heavy chain variable region comprising: a CDR H1 domain comprising SEQ ID NO. 29, a CDR H2 domain comprising SEQ ID NO. 30, and a CDR H3 domain comprising SEQ ID NO. 31, and
  - (ii) a light chain variable region comprising: a CDR L1 domain comprising SEQ ID NO. 32, a CDR L2 domain comprising SEQ ID NO. 33, a CDR L3 domain comprising SEQ ID NO. 34; or
- (d) (i) a heavy chain variable region comprising: a CDR H1 domain comprising SEQ ID NO. 41, a CDR H2 domain comprising SEQ ID NO. 42, and a CDR H3 domain comprising SEQ ID NO. 43, and
  - (ii) a light chain variable region comprising: a CDR L1 domain comprising SEQ ID NO. 44, a CDR L2 domain comprising SEQ ID NO. 45, a CDR L3 domain comprising SEQ ID NO. 46; or
(e) (i) a heavy chain variable region comprising: a CDR H1 domain comprising SEQ ID NO. 47, a CDR H2 domain comprising SEQ ID NO. 48, and a CDR H3 domain comprising SEQ ID NO. 49, and
(ii) a light chain variable region comprising: a CDR LI domain comprising SEQ ID NO. 50, a CDR L2 domain comprising SEQ ID NO. 51, a CDR L3 domain comprising SEQ ID NO. 52.

2. An isolated ADAM17 binding molecule according to claim 1, comprising one of:
(a) (i) a heavy chain variable region comprising amino acids 25-139 of SEQ ID NO. 1, and
(ii) a light chain variable region comprising amino acids 21-136 of SEQ ID NO. 2; or
(b) (i) a heavy chain variable region comprising amino acids 25-139 of SEQ ID NO. 3, and
(ii) a light chain variable region comprising amino acids 21-136 of SEQ ID NO. 4; or
(c) (i) a heavy chain variable region comprising amino acids 25-139 of SEQ ID NO. 5, and
(ii) a light chain variable region comprising amino acids 21-136 of SEQ ID NO. 6; or
(d) (i) a heavy chain variable region comprising amino acids 25-139 of SEQ ID NO. 7, and
(ii) a light chain variable region comprising amino acids 21-136 of SEQ ID NO. 8; or
(e) (i) a heavy chain variable region comprising amino acids 25-139 of SEQ ID NO. 9, and
(ii) a light chain variable region comprising amino acids 21-136 of SEQ ID NO. 10.

3. An isolated ADAM17 binding molecule according to claim 1, comprising one of:
(a) (i) a heavy chain comprising SEQ ID NO. 1 and
(ii) a light chain comprising SEQ ID NO. 2: or
(b) (i) a heavy chain comprising SEQ ID NO. 3 and
(ii) a light chain comprising SEQ ID NO. 4; or
(c) (i) a heavy chain comprising SEQ ID NO. 5 and
(ii) a light chain comprising SEQ ID NO. 6; or
(d) (i) a heavy chain comprising SEQ ID NO. 7 and
(ii) a light chain variable region comprising SEQ ID NO. 8; or
(e) (i) a heavy chain comprising SEQ ID NO. 9 and
(ii) a light chain comprising SEQ ID NO. 10.

4. An ADAM17 binding molecule according to claim 1, wherein the binding molecule is an antibody.

5. An ADAM17 binding molecule according to claim 4, wherein the antibody is a fully human antibody, a chimeric antibody, a monoclonal antibody, a polyclonal antibody, a bi-specific antibody, or a multi-specific antibody.

6. An ADAM 17 binding molecule according to claim 1, wherein the binding molecule is a Fv, a Fab, a F(ab')2, a Fab', a dsFv fragment, a single chain Fv (scFV), an sc(Fv)2, a disulfide-linked (dsFv), a diabody, a triabody, a tetrabody, a minibody, or a single chain antibody.

7. A composition comprising an ADAM17 binding molecule according to claim 1.

8. An isolated nucleic acid molecule comprising a nucleotide sequence encoding an ADAM17 binding molecule according to claim 1.

9. A vector comprising a nucleic acid molecule according to claim 8.

10. A host cell comprising a nucleic acid molecule according to claim 8.

11. A method for detecting ADAM17 in a sample, the method comprising (a) contacting a sample with an ADAM17 binding molecule according to claim 1, and (b) detecting binding of the ADAM17 binding molecule to ADAM17, thereby detecting ADAM17 in the sample.

12. A method for inhibiting the proliferation of, or killing, tumor cells, the method comprising delivering to tumor cells an effective amount of an ADAM17 binding molecule comprising:
(A) (i) a heavy chain variable region comprising: a CDR HI domain comprising SEQ ID NO. 23, a CDR H2 domain comprising SEQ ID NO. 24, and a CDR H3 domain comprising SEQ ID NO. 25, and
(ii) a light chain variable region comprising: a CDR LI domain comprising SEQ ID NO. 26, a CDR L2 domain comprising SEQ ID NO. 27, a CDR L3 domain comprising SEQ ID NO: 28; or
(B) (i) a heavy chain variable region comprising: a CDR H1 domain comprising SEQ ID NO. 41, a CDR H2 domain comprising SEQ ID NO. 42, and a CDR H3 domain comprising SEQ ID NO. 43, and
(ii) a light chain variable region comprising: a CDR LI domain comprising SEQ ID NO. 44, a CDR L2 domain comprising SEQ ID NO. 45, a CDR L3 domain comprising SEQ ID NO. 46.

13. The method of claim 12, wherein the tumor cells are selected from the group consisting of breast cancer cells, colon cancer cells, lung cancer cells, non-small cell lung cancer cells, brain cancer cells, glioma cells, glioblastoma cells, neuroblastoma cells, stomach cancer cells, pancreatic cancer cells, ovarian cancer cells, prostate cancer cells, and kidney cancer cells.

14. The method of claim 12, wherein the tumor cells are triple-negative breast cancer cells.

15. The method of claim 12, wherein the tumor cells are in vitro.

16. The method of claim 12, wherein the tumor cells are in vivo.

17. A method of inhibiting a biological activity in cells or in a tissue, wherein the biological activity is selected from the group consisting of: (a) binding of ADAM17 to an ADAM17 substrate, (b) proteolytic cleavage of an ADAM17 substrate by ADAM17, (c) activation of an ADAM17 substrate, and (d), signaling by an ADAM17 substrate, wherein the method comprises delivering an effective amount of an ADAM17 binding molecule comprising:
(A) (i) a heavy chain variable region comprising: a CDR H1 domain comprising SEQ ID NO. 23, a CDR H2 domain comprising SEQ ID NO. 24, and a CDR H3 domain comprising SEQ ID NO. 25, and
(ii) a light chain variable region comprising: a CDR LI domain comprising SEQ ID NO. 26, a CDR L2 domain comprising SEQ ID NO. 27, a CDR L3 domain comprising SEQ ID NO: 28; or
(B) (i) a heavy chain variable region comprising: a CDR H1 domain comprising SEQ ID NO. 41, a CDR H2 domain comprising SEQ ID NO. 42, and a CDR H3 domain comprising SEQ ID NO. 43, and
(ii) a light chain variable region comprising: a CDR LI domain comprising SEQ ID NO. 44, a CDR L2 domain comprising SEQ ID NO. 45, a CDR L3 domain comprising SEQ ID NO. 46,
to cells or a tissue that expresses or contains ADAM17, thereby inhibiting the biological activity in the cells or tissue.

18. A method of treating cancer in a subject, the method comprising administering to a subject having cancer an effective amount of an ADAM17 binding molecule comprising:
- (A) (i) a heavy chain variable region comprising: a CDR HI domain comprising SEQ ID NO. 23, a CDR H2 domain comprising SEQ ID NO. 24, and a CDR H3 domain comprising SEQ ID NO. 25, and
  - (ii) a light chain variable region comprising: a CDR LI domain comprising SEQ ID NO. 26, a CDR L2 domain comprising SEQ ID NO. 27, a CDR L3 domain comprising SEQ ID NO: 28; or
- (B) (i) a heavy chain variable region comprising: a CDR H1 domain comprising SEQ ID NO. 41, a CDR H2 domain comprising SEQ ID NO. 42, and a CDR H3 domain comprising SEQ ID NO. 43, and
  - (ii) a light chain variable region comprising: a CDR LI domain comprising SEQ ID NO. 44, a CDR L2 domain comprising SEQ ID NO. 45, a CDR L3 domain comprising SEQ ID NO. 46.

19. The method of claim 18, wherein the cancer is triple-negative breast cancer.

20. A method of determining whether a subject with a tumor is a candidate for treatment with an ADAM17 binding molecule, the method comprising:
- (a) contacting a tumor sample from a subject, or cells therefrom, with an ADAM17 binding molecule comprising:
  - (A) (i) a heavy chain variable region comprising: a CDR H1 domain comprising SEQ ID NO. 23, a CDR H2 domain comprising SEQ ID NO. 24, and a CDR H3 domain comprising SEQ ID NO. 25, and
    - (ii) a light chain variable region comprising: a CDR LI domain comprising SEQ ID NO. 26, a CDR L2 domain comprising SEQ ID NO. 27, a CDR L3 domain comprising SEQ; or
  - (B) (i) a heavy chain variable region comprising: a CDR HI domain comprising SEQ ID NO. 41, a CDR H2 domain comprising SEQ ID NO. 42, and a CDR H3 domain comprising SEQ ID NO. 43, and
    - (ii) a light chain variable region comprising: a CDR LI domain comprising SEQ ID NO. 44, a CDR L2 domain comprising SEQ ID NO. 45, a CDR L3 domain comprising SEQ ID NO. 46, and
- (b) performing an assay to determine whether the ADAM17 binding molecule binds to ADAM17 in the sample, whereby if the ADAM17 binding molecule binds to ADAM17 in the sample the subject is a candidate for treatment with an ADAM17 binding molecule.

* * * * *